US 6,680,178 B2

(12) United States Patent  
Harris et al.

(10) Patent No.: US 6,680,178 B2
(45) Date of Patent: Jan. 20, 2004

(54) PROFILING OF PROTEASE SPECIFICITY USING COMBINATORIAL FLUOROGENIC SUBSTRATE LIBRARIES

(75) Inventors: Jennifer L. Harris, San Diego, CA (US); Bradley J. Backes, San Diego, CA (US); Jonathan A. Ellman, Oakland, CA (US); Charles S. Craik, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 169 days.

(21) Appl. No.: 09/866,132

(22) Filed: May 25, 2001

(65) Prior Publication Data

US 2002/0022243 A1 Feb. 21, 2002

Related U.S. Application Data

(60) Provisional application No. 60/209,274, filed on Jun. 2, 2000.

(51) Int. Cl.[7] .................. C12Q 1/37; C12Q 1/00; A61K 38/00
(52) U.S. Cl. .................. 435/23; 435/24; 435/34; 435/4; 530/324; 530/350; 530/334; 530/345; 525/50; 525/54.1; 549/288; 702/22; 702/30
(58) Field of Search .................. 435/24, 23, 34, 435/4; 530/300, 324, 350, 334, 345; 525/50, 54.1; 549/288; 702/22, 30

(56) References Cited

U.S. PATENT DOCUMENTS

| 4,335,204 | A | 6/1982 | Claeson et al. ............. 435/23 |
| 4,448,715 | A | 5/1984 | Ryan et al. ............. 530/328 |
| 4,557,862 | A | 12/1985 | Mangel et al. ............. 435/23 |
| 4,568,636 | A | 2/1986 | Svendsen ............. 435/23 |
| 4,640,893 | A | 2/1987 | Mangel et al. ............. 435/23 |
| 4,897,444 | A | * 1/1990 | Brynes et al. ............. 525/54.1 |

(List continued on next page.)

FOREIGN PATENT DOCUMENTS

| GB | 2324509 A | 10/1998 |
| GB | 2324529 A | * 10/1998 |

OTHER PUBLICATIONS

Sawada et al; "Molecular Reproduction and Development", vol. 45, p 240–243, (1996).*

(List continued on next page.)

*Primary Examiner*—Louise N. Leary
(74) *Attorney, Agent, or Firm*—Townsend and Townsend and Crew LLP

(57) ABSTRACT

A method is presented for the preparation and use of fluorogenic peptide substrates that allows for the configuration of general substrate libraries to rapidly identify the primary and extended specificity of enzymes, such as proteases. The substrates contain a fluorogenic-leaving group, such as 7-amino-4-carbamoylmethyl-coumarin (ACC). Substrates incorporating the ACC leaving group show comparable kinetic profiles as those with the traditionally used 7-amino-4-methyl-coumarin (AMC) leaving group. The bifunctional nature of ACC allows for the efficient production of single substrates and substrate libraries using solid-phase synthesis techniques. The approximately 3-fold increased quantum yield of ACC over AMC permits reduction in enzyme and substrate concentrations. As a consequence, a greater number of substrates can be tolerated in a single assay, thus enabling an increase in the diversity space of the library. Soluble positional protease substrate libraries of 137,180 and 6,859 members, possessing amino acid diversity at the P4-P3-P2-P1 and P4-P3-P2 positions, respectively, were constructed. Employing this screening method the substrate specificities of a diverse array of proteases were profiled, including the serine proteases thrombin, plasmin, factor Xa, uPA, tPA, granzyme B, trypsin, chymotrypsin, human neutrophil elastase, and the cysteine proteases papain and cruzain. The resulting profiles create a pharmacophoric portrayal of the proteases allowing for the design of selective substrates and potent inhibitors.

112 Claims, 13 Drawing Sheets

U.S. PATENT DOCUMENTS

| | | | |
|---|---|---|---|
| 5,079,144 A | | 1/1992 | Carr et al. ..................... 435/32 |
| 5,089,634 A | * | 2/1992 | Powers et al. ............... 549/285 |
| 5,342,970 A | | 8/1994 | Chalom et al. ............. 549/288 |
| 5,872,207 A | * | 2/1999 | Morgan et al. ............. 530/300 |
| 6,037,137 A | | 3/2000 | Komoriya et al. ............ 435/23 |

OTHER PUBLICATIONS

Del Nery et al; "Biochem. J."; V. 323, p 427–433, (1997).*

Morita et al; "J. Biochem."; V. 82; p 1495–1498 (1977).*

Del Nery, et al., "Characterization of the Substrate Specificity of the Major Cysteine Protease Cruzipain) from *Trypanosoma cruzi* Using a Portion–Mixing Combinatorial Library and Fluorogenic Peptides", *Biochemical Journal*, 323:427–433 (1997).

Sawada, et al., "Substrate Specificity of Ascidian Sperm Trypsin–Like Proteases, Spermosin and Acrosin," *Molecular Reproduction and Development*, 45:240–243 (1996).

Adamczyk, et al. "Resin–Supported Labeling Reagents" *Bioorganic & Medicinal Chemistry LEtters* (1999) vol. 9, pp. 217–220.

Backes, et al. "An Alkanesulfonamide 'Safety–Catch' Linker for Solid–Phase Synthesis" *Journal of Organic Chemistry* (1999) vol. 64, pp. 2322–2330.

Backes, et al. "Synthesis of Positional–scanning Libraries of Fluorogenic Peptide Substates to Define the Extended Substrate Specificity of Plasmin and Thrombin" *Nature Biotechnology* (2000) vol. 18, pp. 187–193.

Harris, et al. "Rapid and General Profiling of Protease Specificity by Using Combinatorial Fluorogenic Substrate Libraries" *Proceedings of the National Academy of Sciences* (2000) vol. 97(14) pp. 7754–7759.

Lee, D. et al. "A Substrate Cominatorial Array for Caspases" *Bioorganic and Medicinal Chemistry Letters* (1999) vol. 9, pp. 1667–1672.

Morita, et al. "New Fluorogenic Substrates for α–Thrombin, Factor Xa, Kallikreins, and Urokinase" *Journal of Biochemistry* (1977) vol. 82(5), pp. 1495–1498.

Rano, et al. "A Combinatorial Approach for Determining Protease Specificities: Application to Interleukin–1β Converting Enzyme (ICE)" *Chemistry and Biology* (1997) vol. 4, 149–155.

Zimmerman, et al. "Sensitive Assay for Trypsin, Elastase, and Chymotrypsin Using New Fluorogenic Substrates" *Analytical Biochemistry* (1977) vol. 78, pp. 47–51.

* cited by examiner

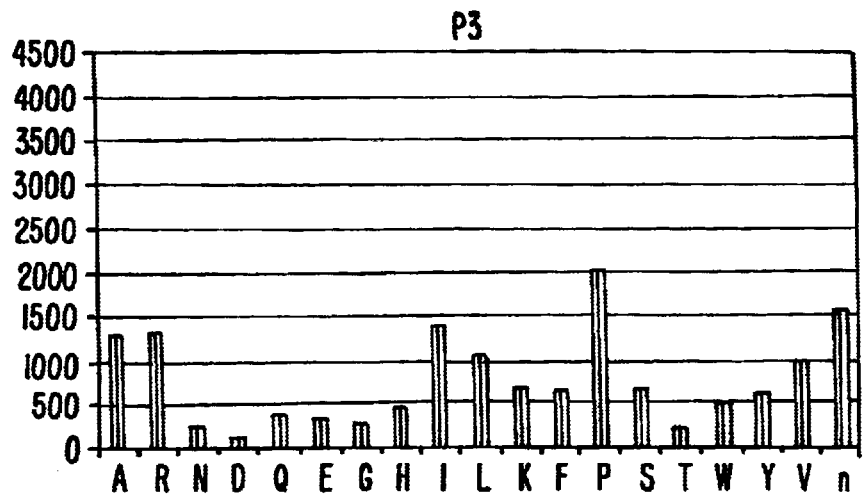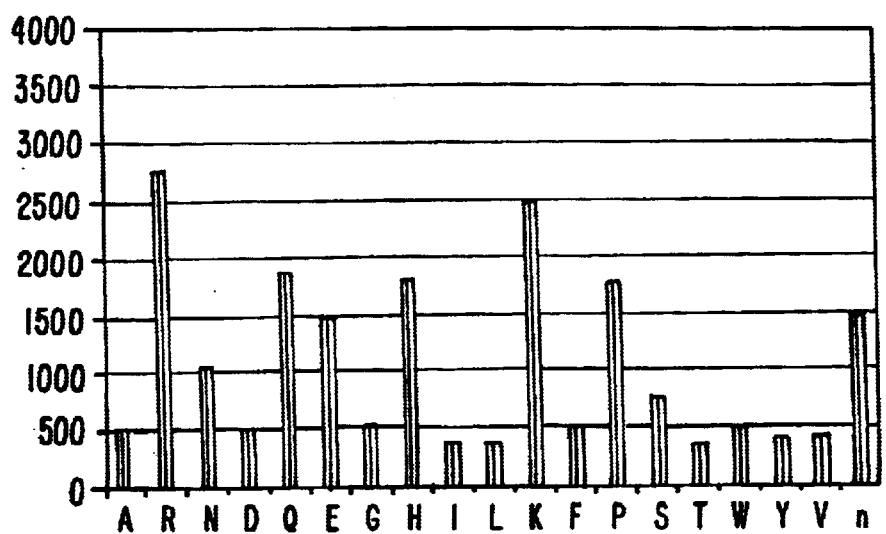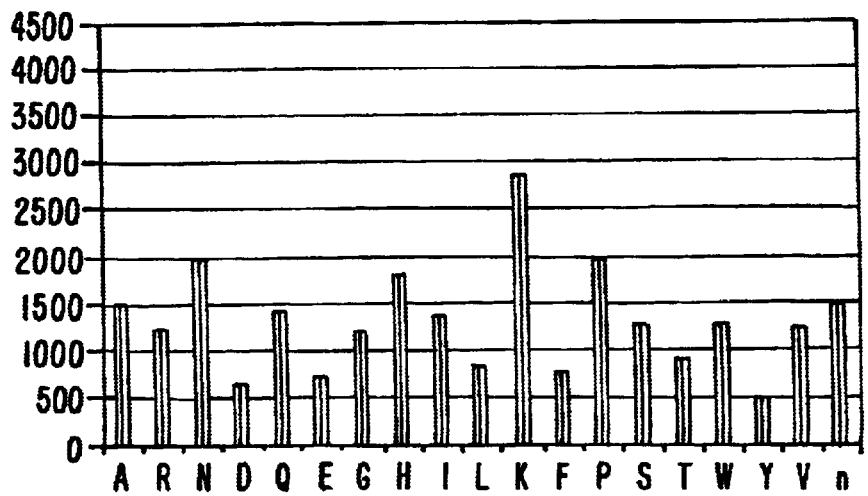
FIG. 3D.

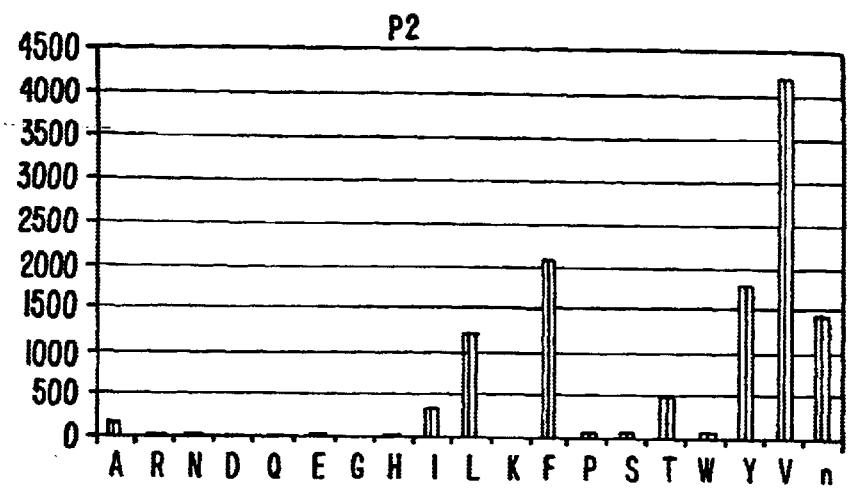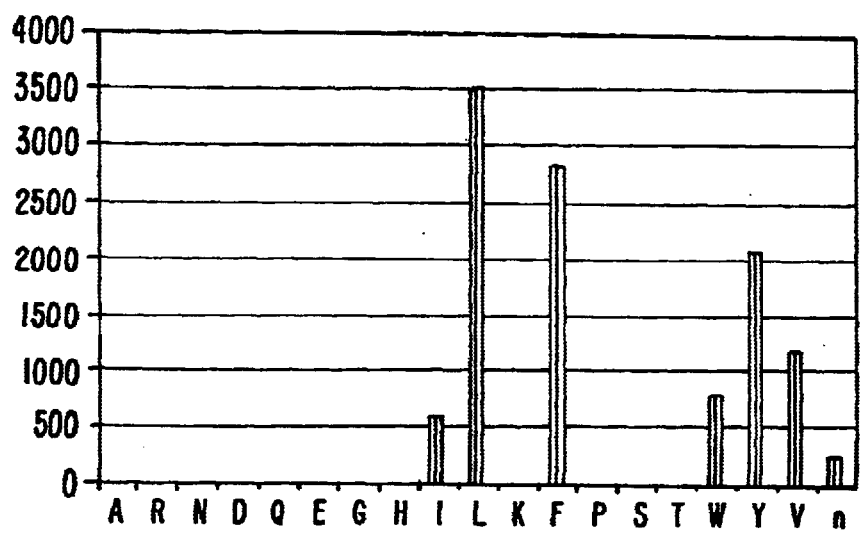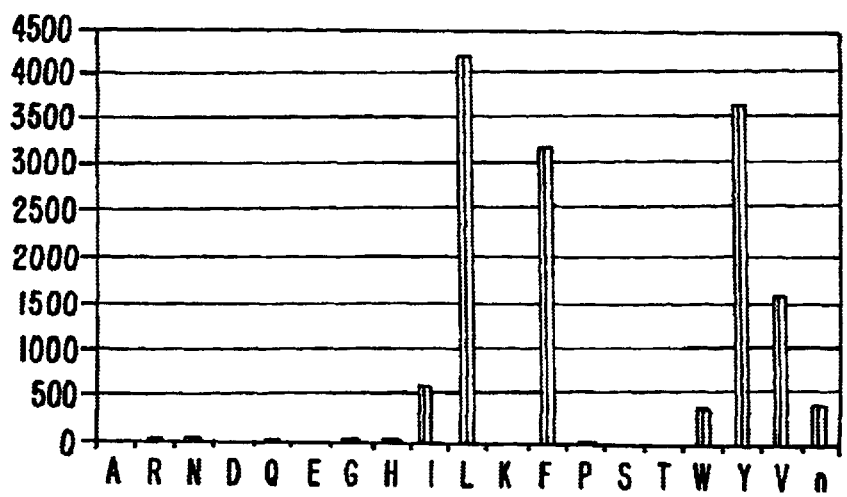
FIG. 3E

FIG. 7.

PROFILING OF PROTEASE SPECIFICITY USING COMBINATORIAL FLUOROGENIC SUBSTRATE LIBRARIES

CROSS REFERENCE TO RELATED APPLICATIONS

The present application claims priority to U.S. Provisional Patent Application Ser. No. 60/209,274, filed on Jun. 2, 2000, the disclosure of which is incorporated herein in its entirety for all purposes.

STATEMENT AS TO RIGHTS TO INVENTIONS MADE UNDER FEDERALLY SPONSORED RESEARCH AND DEVELOPMENT

This work was supported in part by National Institute of Health Grants CA72006, AI35707, GM54051, and National Institute of Health Biotechnology Grant Fellowship, and National Science Foundation Grant MCB9604379. The Government may have certain rights in this invention.

BACKGROUND OF THE INVENTION

The ability of an enzyme to discriminate among many potential substrates is an important factor in maintaining the fidelity of most biological functions. While substrate selection can be regulated on many levels in a biological context, such as spatial and temporal localization of enzyme and substrate, concentrations of enzyme and substrate, and requirement of cofactors, the substrate specificity at the enzyme active site is the overriding principle that determines the turnover of a substrate. Characterization of the substrate specificity of an enzyme clearly provides invaluable information for the dissection of complex biological pathways. Definition of substrate specificity also provides the basis for the design of selective substrates and inhibitors to study enzyme activity.

Of the genomes that have been completely sequenced, 2% of the gene products encode proteases (Barrett, A. J., et al., (1998) *Handbook of Proteolytic Enzymes* (Academic Press, London)). This family of enzymes is crucial to every aspect of life and death of an organism. With the identification of new proteases, there is a need for the development of rapid and general methods to determine protease substrate specificity. While several biological methods, such as peptides displayed on filamentous phage (Matthews, D. J., et al. (1993) *Science* 260:1113–7; Ding, L., et al., (1995) *Proceedings of the National Academy of Sciences of the United States of America* 92:7627–31), and chemical methods, such as support-bound combinatorial libraries (Lam, K. S., et al., (1998) *Methods in Molecular Biology*, 87:1–6), have been developed to identify proteolytic substrate specificity, few offer the ability to rapidly and continuously monitor proteolytic activity against complex mixtures of substrates in solution.

The use of 7-amino-4-methyl coumarin (AMC) fluorogenic peptide substrates is a well-established method for the determination of protease specificity (Zimmerman, M., et al., (1977) *Analytical Biochemistry* 78:47–51). Specific cleavage of the anilide bond liberates the fluorogenic AMC leaving group allowing for the simple determination of cleavage rates for individual substrates. More recently, arrays (Lee, D., et al., (1999) *Bioorganic and Medicinal Chemistry Letters* 9:1667–72) and positional-scanning libraries (Rano, T. A., et aL, (1997) *Chemistry and Biology* 4:149–55) of AMC peptide substrate libraries have been employed to rapidly profile the N-terminal specificity of proteases by sampling a wide range of substrates in a single experiment. Each of these published efforts was designed for profiling caspases, cysteine proteases that require an Asp residue at the P1-position for substrate turnover. This requirement allows for the convenient attachment of the P1-Asp to the solid-support through the carboxylic acid side-chain. Since most proteases do not require P1-Asp/Glu for activity, libraries generated by these methods have limited applicability. Naturally, fluorogenic substrates that contain P1-amino acids that do not possess adequate side-chain functionality for attachment to a solid support in a straightforward manner (Gly, Leu, Val, Ile, Ala, Pro, Phe) will not be amenable to similar synthetic strategies.

Recently Fmoc-based synthesis methods to displace support-bound peptides with nucleophiles in a final cleavage step to produce C-terminal modified peptides have been developed (Backes et al., (1999) *Journal of Organic Chemistry* 64:2322–2330). The preparation of fluorogenic peptide substrates with any residue at the P1-position is possible by the preparation of AMC-amino acid derivatives, which are then used as nucleophiles to produce the AMC-peptide substrates (Backes et al. (2000) *Nature Biotechnology* 18(2): 187–193).

Support bound fluorogenic materials are also known in the art. For example, Adamczyk et al., *Bioorg. Med. Chem. Lett.*, 9:217–220 (1999), have disclosed resin-supported fluorophores prepared from a new N-hydroxysuccinimidyl resin. The resin-bound active esters were used to prepare conjugates with haptens, such as estriol, thyroxine, phenytoin, etc. As the fluorophore is transferred from the resin to the free hapten, the resin-bound fluorophores of Adamczyk et al. do not constitute an appropriate starting point for the solid-phase synthesis of a peptide, nor is the use of the resin-bound fluorophore for derivatization of pre-formed peptides disclosed.

While the art provides a selection of methods that are useful for labeling materials with fluorophores, a method for the solid-phase synthesis of fluorogenic peptides, which begins with a resin-bound fluorophore, and materials that allow the method to be practiced, would represent a significant advance in the art. Such a method has great utility and provides a general strategy for the preparation of fluorogenic peptide substrate libraries. An innovative method would meet the following objectives: (1) the solid-phase synthesis method should enable direct incorporation of at least all 20 proteinogenic amino acids at every position, including the P1-position; (2) the method should be compatible with art-recognized solid-phase peptide synthesis protocols and instrumentation; and (3) the method should be flexible enough to enable the rapid synthesis of any single substrate, substrate array, and positional scanning library. Quite surprisingly, the present invention provides such a method.

SUMMARY OF THE INVENTION

The present invention provides, for the first time, a highly efficient method for the preparation of fluorogenic compound libraries, particularly peptide substrate libraries based upon a new bifunctional fluorogenic-leaving group. The leaving group of the invention is exemplified by 7-amino-4-carbamoylmethyl-coumarin (ACC). In an illustrative embodiment, using Fmoc-synthesis protocols, all 20 proteinogenic amino acids can be directly coupled to the support bound ACC-leaving group to provide general sets of substrates for analyzing protease substrate specificity. The versatility of the solid-phase synthesis strategy allows for substrate-arrays (Lee, D., et al., (1999) *Bioorganic and*

Medicinal Chemistry Letters 9:1667–72) and positional scanning libraries (Rano, T. A., et aL, (1997) Chemistry and Biology 4:149–55) of any configuration to be rapidly prepared. The substrate specificity of numerous representative serine and cysteine proteases were profiled to show the utility and generality of libraries generated by the ACC method.

Thus, in a first aspect, the present invention provides a material having the structure:

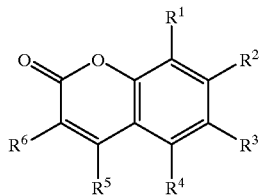

(I)

wherein: $R^1$, $R^2$, $R^3$, $R^4$, $R^5$ and $R^6$ are members independently selected from the group consisting of H, halogen, —$NO_2$, —CN, —$C(O)_mR^7$, —$C(O)NR^8R^9$, —$S(O)_tR^{10}$, —$SO_2NR^{11}R^{12}$, —$OR^{13}$, substituted or unsubstituted alkyl, —$R^{14}$—SS, and —$NHR^{15}$ with the proviso that at least one of $R^1$, $R^2$, $R^3$, $R^4$, $R^5$ and $R^6$ is —$R^{14}$—SS and at least one of $R^1$, $R^2$, $R^3$, $R^4$, $R^5$ and $R^6$ is —$NHR^{15}$. $R^7$, $R^8$, $R^9$, $R^{10}$, $R^{11}$, $R^{12}$ and $R^{13}$ are members independently selected from the group consisting of H, substituted or unsubstituted alkyl and substituted or unsubstituted aryl. $R^{14}$ is a linking group adjoining the fluorogenic moiety and the solid support. $R^{15}$ is a member selected from the group consisting of amine protecting groups, —C(O)-AA and —C(O)—P. P is a peptide sequence. AA is an amino acid residue. The subscript m is a member selected from the group consisting of the integers 1 and 2. The subscript t is a member selected from the group consisting of the integers from 0 to 2; and SS is a solid support.

In a second aspect, the present invention provides a fluorogenic peptide comprising a fluorogenic moiety covalently bound to a peptide sequence. The peptide includes the structure:

R—P (VII)

wherein, P is a peptide sequence having a structure that is substantially identical to that set forth in Formula II. R is a fluorogenic moiety having a structure substantially similar to the fluorogenic moiety of Formula I. The fluorogenic group substituents, $R^1$, $R^2$, $R^3$, $R^4$, $R^5$ and $R^6$, are members independently selected from the group consisting of H, halogen, —$NO_2$, —CN, —$C(O)_mR^7$, —$C(O)NR^8R^9$, —$S(O)_tR^{10}$, —$SO_2NR^{11}R^{12}$, —$OR^{13}$, substituted or unsubstituted alkyl, —NHC(O)—P, and —$R^{20}$—Y. At least one of $R^1$, $R^2$, $R^3$, $R^4$, $R^5$ and $R^6$ is —$R^{20}$—Y and at least one of $R^1$, $R^2$, $R^3$, $R^4$, $R^5$ and $R^6$ is —NHC(O)—P. $R^7$, $R^8$, $R^9$, $R^{10}$, $R^{11}$, $R^{12}$ and $R^{13}$ are members independently selected from the group consisting of H, substituted or unsubstituted alkyl and substituted or unsubstituted aryl. $R^{20}$ is either present or absent, and when present, is a member selected from the group consisting of substituted or unsubstituted alkyl and substituted or unsubstituted heteroalkyl; when $R^{20}$ is absent, Y is attached directly to the fluorogenic moiety. Y is an organic functional group or methyl, and is preferably a member selected from the group consisting of —$COOR^{17}R^{21}$, $CONR^{17}R^{21}$, —$C(O)R^{17}$, —$OR^{17}$, —$SR^{17}$, —$NR^{17}R^{21}$, —$C(O)NR^{17}R^{21}$, and —$C(O)SR^{17}$. $R^{17}$ and $R^{21}$ are members independently selected from H, substituted or unsubstituted alkyl and substituted or unsubstituted aryl. The subscript m is a member selected from the group consisting of the integers 1 and 2; and t is a member selected from the group consisting of the integers from 0 to 2.

In a further aspect, the present invention provides a library of fluorogenic peptides having a structure according to Formula VII. The library includes at least a first peptide having a first peptide sequence covalently attached to a first fluorogenic moiety and a second peptide having a second peptide sequence covalently attached to a second fluorogenic moiety. For each of each of the peptides of the library, P is independently selected from peptide sequences, preferably having the structure:

—$C(O)$-$AA^1$-$AA^2$-$(AAi)_{J-2}$) (II).

Each of $AA^1$ through $AA^i$ is an amino acid residue which is a member independently selected from the group consisting of natural amino acid residues, unnatural amino acid residues and modified amino acid residues. Each J is independently selected and denotes the number of amino acid residues forming the first peptide sequence and the second peptide sequence and is a member selected from the group consisting of the numbers from 1 to 10. J can have the same value for each of the peptide sequences in a particular library, or it can have a different value for two or more of the peptides of the library. Each i is independently selected and denotes the position of the amino acid residue relative to $AA^1$ and when J is greater than 2, i is a member selected from the group consisting of the numbers from 3 to 10.

For each of the peptides of the library, R is independently selected from fluorogenic moieties having a structure according to Formula I. Thus, the fluorogenic group(s) can be the same for each of the peptides of a particular library or the structure of R can vary in a selected manner for two or more peptides of the library.

For each of the library peptides having a structure according to Formula I, the substituents of the fluorogenic group, $R^1$, $R^2$, $R^3$, $R^4$, $R^5$, and $R^6$ are independently selected from the group consisting of H, halogen, —$NO_2$, —CN, —$C(O)_mR^7$, —$C(O)NR^8R^9$, —$S(O)_tR^{10}$, —$SO_2NR^{11}R^{12}$, —$OR^{13}$, substituted or unsubstituted alkyl, —NH—C(O)-P, $R^{20}$—Y, and —$R^4$—SS. For each library peptide, at least one of $R^1$, $R^2$, $R^3$, $R^4$, $R^5$, and $R^6$ is a member independently selected from —$R^{14}$—SS and —$R^{14}$—Y and at least one of $R^1$, $R^2$, $R^3$, $R^4$, $R^5$, and $R^6$ is —NH—C(O)—P. $R^7$, $R^8$, $R^9$, $R^{10}$, $R^{11}$, $R^{12}$ and $R^{13}$ for each library peptide are members independently selected from the group consisting of H, substituted or unsubstituted alkyl and substituted or unsubstituted aryl. $R^{14}$ is a linking group adjoining the fluorogenic moiety and the solid support. $R^{20}$ is either present or absent, and when present, is a member selected from the group consisting of substituted or unsubstituted alkyl, and substituted or unsubstituted heteroalkyl; when $R^{20}$ is absent, Y is attached directly to the fluorogenic moiety. The subscript m is a member selected from the group consisting of the integers from 1 to 2. The subscript t is a member selected from the group consisting of the integers from 0 to 2. Y is an organic functional group or methyl, and is preferably a member selected from the group consisting of —$COOR^{17}$, $CONR^{17}R^{21}$, —$C(O)R^{17}$, —$OR^{17}$, —$SR^{17}$, $NR^{17}R^{21}$, —$C(O)NR^{17}R^{21}$, and —$C(O)SR^{17}$. For each library peptide, $R^{17}$ and $R^{21}$ are members independently selected from the group consisting of H and substituted or unsubstituted alkyl. SS is a solid support.

Other objects and advantages of the present invention will be apparent from the Detailed Description, which follows.

Figure 1:
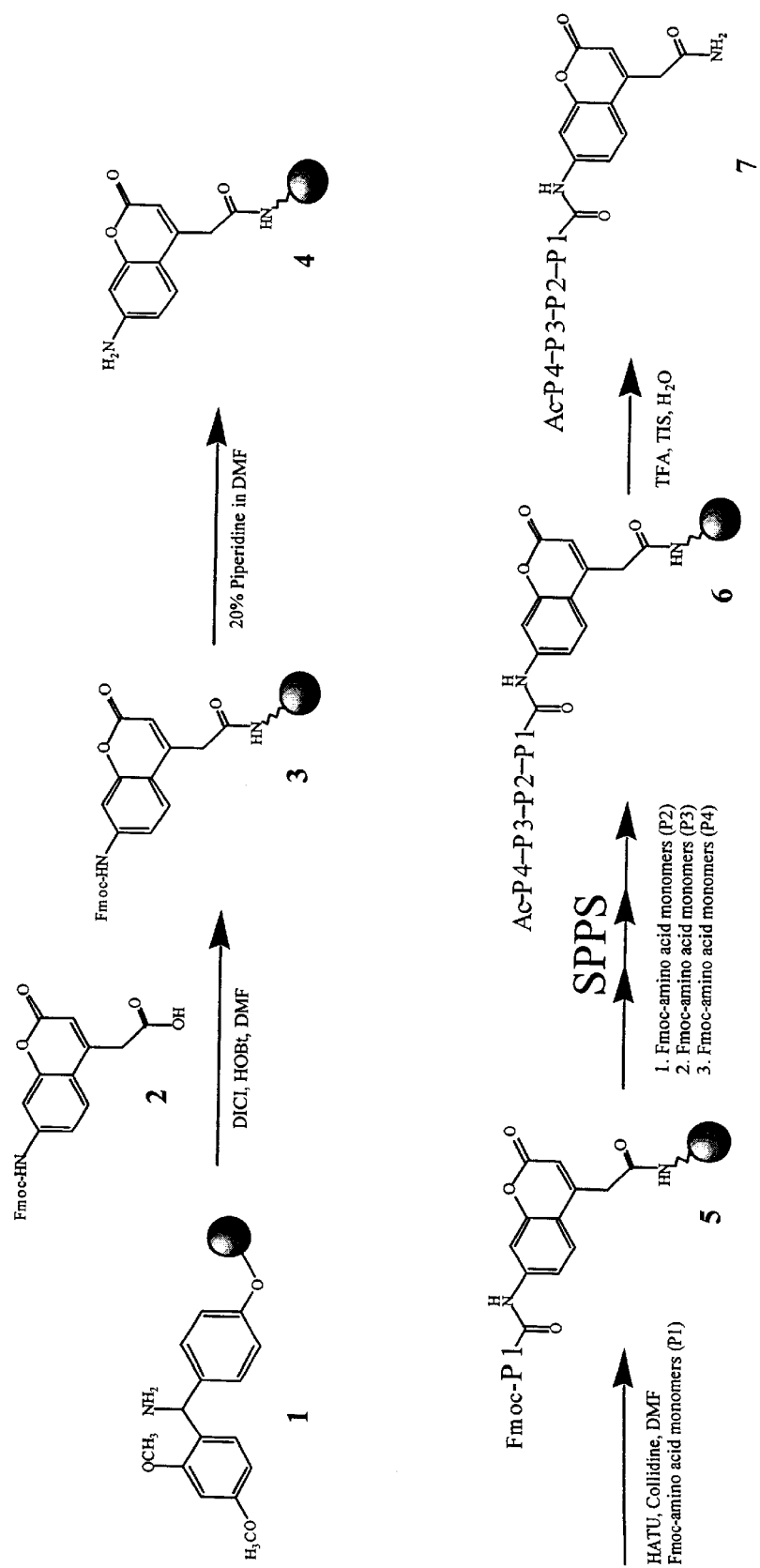
FIG. 1 Synthesis of 7-amino-4-carbamoylmethyl-coumarin substrates. (SPPS represents Solid-Phase Peptide Synthesis using standard Fmoc protocols).

A. Chymotrypsin; B. Trypsin; C. Thrombin; D. Plasmin; E. Granzyme B; F. Human Neutrophil Elastase; G. Papain; and H. Cruzain.

FIG. 3 Profiles of serine and cysteine proteases against P1-fixed ACC PS-SCL. The Y-axis is the pM of fluorophore released per second. The X-axis provides the spatial address of the amino acid as represented by the one letter code (with "n" representing norleucine).

A. Lys, Plasmin; B. Arg, Thrombin; C. Arg, uPA; D. Arg, tPA; E. Arg, Factor Xa; F. Arg, Papain; G. Arg, Cruzain; H. Leu, Cruzain.

FIG. 4 Coomassie-stained gel of βI and βII tryptase expression products. A. Recombinant βI tryptase, non-, single-, double-, and hyper-glycosylation forms are observed. B. Recombinant βII tryptase, non-, and single-glycosylation forms are observed. C. Native β-tryptase. D. Molecular mass standards.

FIG. 5 Results from the P1-Diverse positional scanning library where the y-axis represents the rate of substrate cleavage (fluorophore release) over time and the x-axis represents the P1-amino acid. The P2, P3 and P4 positions contain an equimolar mixture of 19 amino acids (Cys and Met excluded, Nle included) for a total of 6,859 substrates/well.

FIG. 6 Results from the P1-Lys (A) and the P1-Arg (B) libraries where the y-axis represents the rate of substrate cleavage (fluorophore release) over time and the x-axis represents the positioned P2-, P3- or P4-amino acid. The two positions in the substrate that are not held constant contain an equimolar mixture of 19 amino acids (Cys and Met excluded, Nle included) for a total of 361 substrates/well.

Figure 7:
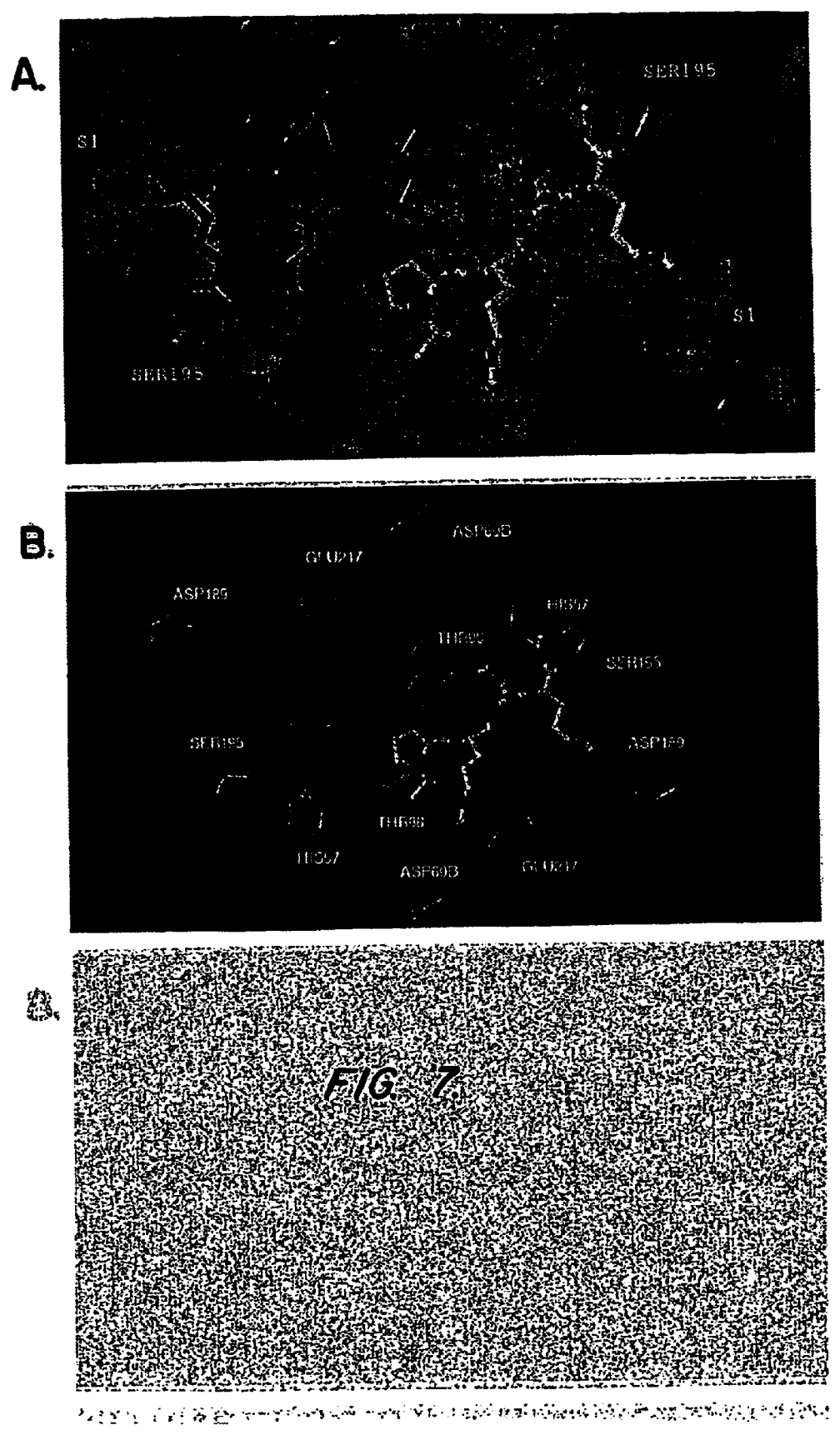

FIG. 7 Structural model of Ac-Pro-Arg-Asn-Lys-Nme substrate interaction with tryptase. Two protomers are shown in green and orange. Two docked substrates are shown in magenta and white. Solvent-accessible surface of enzyme shown in (A). Figures prepared using Sybyl.

DETAILED DESCRIPTION OF THE INVENTION AND THE PREFERRED EMBODIMENTS

Abbreviations and Definitions

All technical and scientific terms used herein generally have the same meaning as commonly understood by one of ordinary skill in the art to which this invention belongs. The present definitions and abbreviations are generally offered to supplement the art-recognized meanings. Generally, the nomenclature used herein and the laboratory procedures organic chemistry, enzyme chemistry and peptide synthesis described below are those well known and commonly employed in the art. Generally, enzymatic reactions and purification steps are performed according to the manufacturer's specifications. Standard techniques, or modifications thereof, are used for chemical syntheses and chemical analyses.

"AMC," as used herein refers to, 7-amino-4-methyl-coumarin.

"ACC," as used herein refers to, 7-amino-4-carbamoylmethyl-coumarin.

"RFU," as used herein refers to, relative fluorescence units.

"n" and "Nle," as used herein refer to, norleucine.

"PS—SCL," as used herein refers to, positional scanning-synthetic combinatorial library;

"MUGB," as used herein refers to, 4-methylumbelliferyl p-guanidinobenzoate.

"Tris," as used herein refers to, tris-(hydroxymethyl)-amino-methane.

"DIC," as used herein refers to, diisopropylcarbodiimide.

"HOBt," as used herein refers to, 1-hydroxybenzotriazole.

"TFA," as used herein refers to, trifluoroacetic acid.

"Fmoc," as used herein refers to, 9-fluorenylmethoxycarbonyl.

"pbf," as used herein refers to, 2,2,4,6,7-pentamethyldihydrobenzofuran-5-sulfonyl.

"trt," as used herein refers to, trityl.

"Boc," as used herein refers to, tert butoxycarbonyl.

"DMF," as used herein refers to, N,N-dimethylformamide.

"NMP," as used herein refers to, N-methylpyrrolidine.

"TIS," as used herein refers to, triisopropylsilane.

"pbf," as used herein refers to, 2,2,4,6,7-pentamethyldihydrobenzofuran-5-sulfonyl.

"trt," as used herein refers to, trityl.

"HATU," as used herein refers to, O-(7-azabenzotriazol-1-yl)-1,1,3,3-tetramethyluronium hexafluorophosphate.

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multi-valent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene."

The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

"Substituted alkyl" refers to alkyl as just described including one or more substituents such as, for example, lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) 0, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$H_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a diazo, methylene or ethylene moiety. The linking group may also be a carbonyl such as in cyclohexyl phenyl ketone. The term "substituted aryl" encompasses "substituted arylalkyl."

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to —NRR', wherein R and R' are independently H, alkyl, aryl or substituted analogues thereof. "Amino" encompasses "alkylamino" denoting secondary and tertiary amines and "acylamino" describing the group RC(O)NR'.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "linking group" refers to a group that links a fluorogenic moiety to a solid support. Linking groups of diverse structures are useful in practicing the present invention. Exemplary linking groups include, but are not limited to, organic functional groups (e.g., —C(O)—, —NR—, —C(O)S—, —C(O)NR—, etc.); substituted or unsubstituted alkyl, substituted or unsubstituted heteroalkyl and substituted or unsubstituted aryl groups each of which are, in addition to other optional substituents, homo- or hetero-disubstituted with organic functional groups, that adjoin the linker arm to the fluorophore and to the solid support. The linking groups of the invention can include a group that is cleaved by, for example, light, heat, reduction, oxidation, hydrolysis or enzymatic action (e.g., nitrophenyl, disulfide, ester, etc.). Alternatively, the linking group is substantially stable under a range of conditions. By providing for the use of linkers with a wide range of physicochemical characteristic, the invention allows selected properties of the material of the invention and its conjugates to be manipulated. Properties that are amenable to manipulation include, for example, hydrophobicity, hydrophilicity, surface-activity and the distance from the solid support of the species bound to the solid support via the linking group.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L -isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Fluorogen," as used herein, refers broadly to a class of compounds capable of being modified enzymatically or otherwise to give a derivative fluorophore, which has a modified or an increased fluorescence.

"Solid support," as used herein refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. A solid support can also be a substrate, for example, a chip, wafer or well, onto which an individual, or more than one compound, of the invention is bound.

"Organic functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Methods to prepare each of these functional groups are well-known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Introduction

The present invention provides a new fluorogenic leaving group that is attached to a solid support (e.g., acid-labile Rink linker) to provide a solid support useful for solid-phase synthesis of diverse monomeric, oligomeric and polymeric materials. Also provided are compounds to which the fluorogenic leaving group is attached libraries of such compounds and methods of using these compounds and libraries.

The invention alleviates many of the difficulties associated with art-recognized methods of forming fluorogenic compounds. For example, using the solid support of the invention, fluorogenic peptides having substantially any amino acid residue at the carboxy-terminus ("P1") are easily prepared. The ability to prepare peptide libraries having complete diversity at P1 using solid-phase techniques eliminates the well known shortcomings of solution synthesis techniques, speeding both synthesis and purification.

Solid Supports

Synthesis on solid supports, "solid-phase synthesis," is of recognized utility in the synthesis of small molecules, oligomeric compounds and polymers. A diverse array of solid supports bearing useful probes, labels and reactive groups are known in the art (see, for example, Burgess, ed., SOLID-PHASE ORGANIC SYNTHESIS, John Wiley and Sons, 2000; and Chan and White, eds., FMOC SOLID PHASE PEPTIDE SYNTHESIS: A PRACTICAL APPROACH (The Practical Approach Series), Oxford University Press, 2000. Solid supports include substantially any oligomeric or polymeric material upon which a selected synthesis can be performed, and the materials and methods of the present invention are not limited by the identity of the material serving as the solid support.

Thus, in a first aspect, the present invention provides a material having the structure:

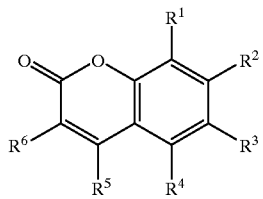

(I)

wherein: $R^1$, $R^2$, $R^3$, $R^4$, $R^5$ and $R^6$ are members independently selected from the group consisting of H, halogen, $-NO_2$, $-CN$, $-C(O)_mR^7$, $-C(O)NR^8R^9$, $-S(O)_tR^{10}$, $-SO_2NR^{11}R^{12}$, $-OR$, substituted or unsubstituted alkyl, $-R^4-SS$, and $-NHR^{15}$ with the proviso that at least one of $R^1$, $R^2$, $R^3$, $R^4$, $R^5$ and $R^6$ is $-R^4-SS$ and at least one of $R^1$, $R^2$, $R^3$, $R^4$, $R^5$ and $R^6$ is $-NHR^{15}$. $R^7$, $R^8$, $R^9$, $R^{10}$, $R^{11}$, $R^{12}$ and $R^{13}$ are members independently selected from the group consisting of H, substituted or unsubstituted alkyl and substituted or unsubstituted aryl. $R^{14}$ is a linking group adjoining the fluorogenic moiety and the solid support. $R^{15}$ is a member selected from the group consisting of arnine protecting groups, $-C(O)-AA$ and $-C(O)-P$. P is a peptide sequence. AA is an amino acid residue. The subscript m is a member selected from the group consisting of the integers 1 and 2. The subscript t is a member selected from the group consisting of the integers from 0 to 2; and SS is a solid support.

In a presently preferred embodiment, the linking group, $R^{14}$, is an organic functional group adjoining the fluorogenic moiety and the solid support. In another preferred embodiment, $R^{14}$ is member selected from the group consisting of substituted or unsubstituted alkyl, substituted or unsubstituted heteroalkyl and substituted or unsubstituted aryl groups, which are homo- or hetero-disubstituted with functional groups adjoining the linker to both the fluorogenic moiety and the solid support. Linkers useful for forming conjugates between solid supports and other species are well known in the art (see, for example, James, *Tetrahedron* 55: 4855–4946 (1999)).

In a preferred embodiment, the invention provides a material according to Formula I, in which P is a peptide sequence comprising the structure:

(II)

wherein, $AA^1$-$AA^2$-$(AA^i)_{j-2}$ is a peptide sequence. Each of $AA^1$ through $AA^i$ is an amino acid residue which is a member independently selected from the group of natural amino acid residues, unnatural amino acid residues and modified amino acid residues. The subscript J denotes the number of amino acid residues forming the peptide sequence and is a member selected from the group consisting of the numbers from 2 to 10, such that J-2 is the number of amino acid residues in the peptide sequence exclusive of $AA^1$-$AA^2$. The superscript i denotes the position of an amino acid residue relevant to $AA^1$. When J is greater than 2, i is a member selected from the group consisting of the numbers from 3 to 10.

In another preferred embodiment, the invention provides a material according to Formula I, in which $R^{15}$ has the structure:

(III)

In Formula III, AA is an amino acid residue selected from the group consisting of natural amino acids, unnatural amino acids and modified amino acids.

In a still further preferred embodiment, the invention provides a material according to Formula I, which has the structure:

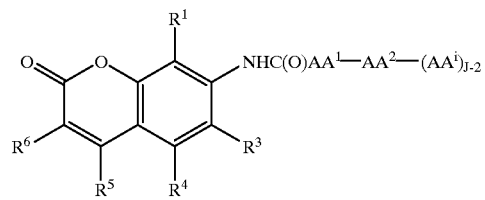

(IV)

in which, the substituents $R^1$, $R^3$, $R^4$, $R^5$ and $R^6$ have substantially the same identities as set forth herein above in conjunction with the materials according to Formula I. The compounds according to this embodiment can comprise the single peptide sequence displayed in Formula IV, or one or more additional peptide sequences, which are the same as or different than the peptide sequence of Formula IV. Moreover, the materials of the invention can comprise an amino acid as displayed in Formula III in addition to one or more peptide sequences.

In another preferred embodiment, the material of the invention has the structure:

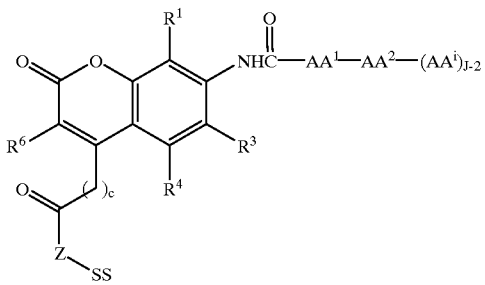

(V)

wherein, the substituents $R^1$, $R^3$, $R^4$ and $R^6$ are substantially identical to those substituents set forth in conjunction with the material of the invention according to Formula IV. Z is a linking selected from —O—, —$NR^{16}$— and —S—. $R^{16}$ is preferably a member selected from H and substituted or unsubstituted alkyl. The subscript c represents an integer, which is preferably selected from 0 to 6.

In another preferred embodiment, the invention provides a material having the structure:

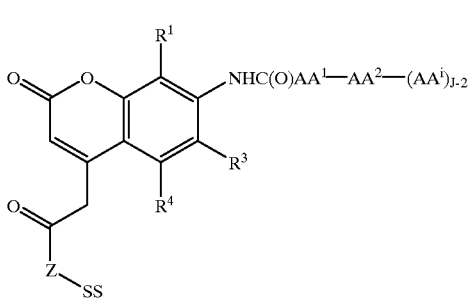

(VI)

in which the identities of the substituents $R^1$, $R^3$, and $R^4$ and the identity of the linking group Z are substantially as described hereinabove.

The fluorogenic materials of the invention are also of use as solid supports for the synthesis of individual compounds other than peptides and libraries consisting of an array of individual compounds other than peptides. Exemplary compounds that can be synthesized using the solid support of the invention include, but are not limited to, small molecules and oligomers (e.g., nucleic acids, lipids, saccharides, etc.). Thus, the present invention provides libraries of fluorogenic compounds other than peptides.

Fluorogenic Compounds

Fluorogenic compounds are of use as probes for an array of applications, including structural elucidation of materials, substrate specificity of enzymes, hybridization of nucleic acids, substrate transformation, digestion or degradation of biomolecules, such as peptides, nucleic acids, saccharides and the like. As discussed above, the present invention provides a solid support, which allows for the conjugation of a fluorogenic moiety to compounds of different types, which are synthesized on the solid support of the invention.

Thus, in a second aspect, the present invention provides a fluorogenic peptide comprising a fluorogenic moiety covalently bound to a peptide sequence. The peptide includes the structure:

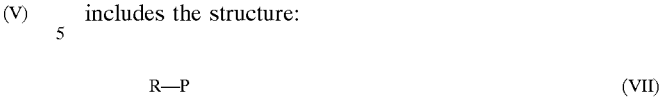

wherein, P is a peptide sequence having a structure that is substantially identical to that set forth in Formula II. R is a fluorogenic moiety having a structure substantially similar to the fluorogenic moiety of Formula I.

In the present aspect of the invention, the fluorogenic group substituents, $R^1$, $R^2$, $R^3$, $R^4$, $R^5$ and $R^6$, are members independently selected from the group consisting of H, halogen, —$NO_2$, —CN, —$C(O)_m R^7$, —$C(O)NR^8 R^9$, —$S(O)_t R^{10}$, —$SO_2 NR^{11} R^{12}$, —$OR^{13}$, substituted or unsubstituted alkyl, —NHC(O)—P, and —$R^{20}$—Y. At least one of $R^1$, $R^2$, $R^3$, $R^4$, $R^5$ and $R^6$ is —$R^{20}$—Y and at least one of $R^1$, $R^2$, $R^3$, $R^4$, $R^5$ and $R^6$ is —NHC(O)—P. $R^7$, $R^8$, $R^9$, $R^{10}$, $R^{11}$, $R^{12}$ and $R^{13}$ are members independently selected from the group consisting of H, substituted or unsubstituted alkyl and substituted or unsubstituted aryl. $R^{20}$ is either present or absent, and when present, is a member selected from the group consisting of substituted or unsubstituted alkyl and substituted or unsubstituted heteroalkyl; when $R^{20}$ is absent, Y is attached directly to the fluorogenic moiety. Y is an organic functional group or methyl, and is preferably a member selected from the group consisting of —$COOR^{17} R^{21}$, $CONR^{17} R^{21}$, —$C(O)R^{17}$, —$OR^{17}$, —$SR^{17}$, —$NR^{17} R^{21}$, and —$C(O)SR^{17}$. $R^{17}$ and $R^{21}$ are members independently selected from H, substituted or unsubstituted alkyl and substituted or unsubstituted aryl. The subscript m is a member selected from the group consisting of the integers 1 and 2; and t is a member selected from the group consisting of the integers from 0 to 2.

In a further preferred embodiment, the present invention provides a fluorogenic peptide having a structure substantially identical to that set forth in Formula IV. The identities of the fluorogenic group substituents, $R^1$, $R^3$, $R^4$, $R^5$ and $R^6$, are substantially identical to those set forth for the peptides of the invention according to Formula VII.

In another preferred embodiment, the invention provides a peptide having the structure:

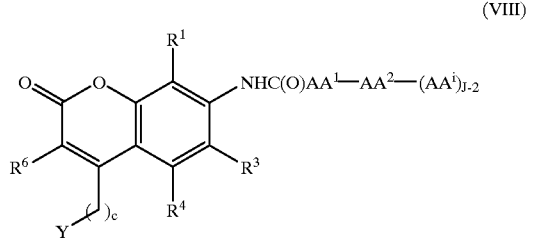

(VIII)

wherein, c is a member selected from the group consisting of the integers from 0 to 6.

In yet a further preferred embodiment, the invention provides a fluorogenic peptide having the structure:

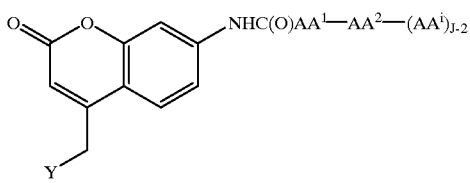
(IX)

in which Y is substantially as described above.

The fluorogenic peptides of the invention preferably have a peptide sequence that includes at least one peptide bond cleavable by an enzyme, preferably a protease. Cleaving the peptide bond preferably releases the fluorogenic moiety from the peptide sequence, thereby producing a fluorescent moiety and a peptide moiety. The peptide bond, which undergoes enzymatic cleavage can be located at any site within the peptide sequence, but is preferably located at a peptide bond formed between an amine of the fluorogenic moiety and a carboxylic acid moiety of the peptide carboxy terminus.

The present invention also provides the ability to introduce an additional element of diversity in the positional scanning combinatorial libraries through the preparation of a peptide library consisting of a plurality of wells (preselected amino acids, can be omitted or included) addressing a fixed P1 amino acid. In an illustrative embodiment having 20 wells, a tetrapeptide is prepared in which the P2-P3-P4 positions in the library consist of an equimolar mixture of 19 amino acids (cysteine is omitted and norleucine is substituted for methionine) for a total of 6,858 substrates per well and 137,180 substrates per library. The present invention provides a further advantage in that, if members of the library are sparingly soluble under a particular set of conditions, to avoid insolubility of the substrates as well as to maintain $k_{cat}/K_m$ conditions, the concentration for each individual substrate per well can be decreased to approximately 0.01 µM. The increased fluorescence of the ACC fluorophore of the invention, relative to the AMC fluorophore, provides for the use of lower concentrations of substrate than in art-recognized methods.

Compound Libraries

The synthesis and screening of chemical libraries to identify compounds having useful biological and material properties is now a common practice. Illustrative of the many different types of libraries that have been prepared are libraries including collections of oligonucleotides, oligopeptides, and small or large molecular weight organic or inorganic molecules. See, Moran et al., PCT Publication WO 97/35198, published Sep. 25, 1997; Baindur et al., PCT Publication WO 96/40732, published December 19, 1996; Gallop et al., J. Med. Chem. 37:1233–51 (1994).

Thus, in a further aspect, the present invention provides a library of fluorogenic compounds. In a presently preferred embodiment, there is provided a library of fluorogenic peptides having a structure according to Formula VII.

R—P  (VII)

The library includes at least a first peptide having a first peptide sequence covalently attached to a first fluorogenic moiety and a second peptide having a second peptide sequence covalently attached to a second fluorogenic moiety. For each of each of the peptides of the library, P is independently selected from peptide sequences preferably having the structure:

—C(O)-AA$^1$-AA$^2$-(AA$^i$)$_{J-2}$  (II).

Each of AA$^1$ through AA$^2$ is an amino acid residue which is a member independently selected from the group consisting of natural amino acid residues, unnatural amino acid residues and modified amino acid residues. Each J is independently selected and denotes the number of amino acid residues forming the first peptide sequence and the second peptide sequence and is a member selected from the group consisting of the numbers from 1 to 10. J can have the same value for each of the peptide sequences in a particular library, or it can have a different value for two or more of the peptides of the library. Each i is independently selected and denotes the position of the amino acid residue relative to AA$^1$ and when J is greater than 2, i is a member selected from the group consisting of the numbers from 3 to 10.

For each of the peptides of the library, R is independently selected from fluorogenic moieties having a structure according to Formula I. Thus, the fluorogenic group(s) can be the same for each of the members of a particular library or the structure of R can vary in a selected manner for two or more members of the library.

For each of the library peptides having a structure according to Formula I, the substituents of the fluorogenic group, R$^1$, R$^2$, R$^3$, R$^4$, R$^5$, and R$^6$ are independently selected from the group consisting of H, halogen, —NO$_2$, —CN, —C(O)$_m$R$^7$, —C(O)NR$^8$R$^9$, —S(O)$_t$R$^{10}$, —SO$_2$NR$^{11}$R$^{12}$, —OR$^{13}$, substituted or unsubstituted alkyl, —NH—C(O)—P, R$^{20}$—Y, and —R$^{14}$—SS. For each library peptide, at least one of R$^1$, R$^2$, R$^3$, R$^4$, R$^5$, and R$^6$ is a member independently selected from —R$^{14}$—SS and —R$^{20}$—Y and at least one of R$^1$, R$^2$, R$^3$, R$^4$, R$^5$, and R$^6$ is —NH—C(O)—P. R$^7$, R$^8$, R$^9$, R$^{10}$, R$^{11}$, R$^{12}$ and R$^{13}$ for each library peptide are members independently selected from the group consisting of H, substituted or unsubstituted alkyl and substituted or unsubstituted aryl. R$^{14}$ is a linking group adjoining the fluorogenic moiety and the solid support. R$^{20}$ is either present or absent, and when present, is a member selected from the group consisting of substituted or unsubstituted alkyl, and substituted or unsubstituted heteroalkyl; when R$^{20}$ is absent, Y is attached directly to the fluorogenic moiety. The subscript m is a member selected from the group consisting of the integers from 1 to 2. The subscript t is a member selected from the group consisting of the integers from 0 to 2. Y is an organic functional group or methyl and is preferably a member selected from the group consisting of —COOR$^{17}$, CONR$^{17}$R$^{21}$, —C(O)R$^{17}$, —OR$^{17}$, —SR$^{17}$, —C(O)SR$^{17}$ and NR$^{17}$R$^{21}$. For each library peptide, R$^{17}$ and R$^{21}$ are members independently selected from the group consisting of H and substituted or unsubstituted alkyl. SS is a solid support.

In other preferred embodiments, the invention provides a library of fluorogenic peptides wherein, each of the peptides of the library has an independently selected structure according to Formula IV. In this embodiment the substituents on the fluorogenic group, R$^1$, R$^3$, R$^4$, R$^5$ and R$^6$, are independently selected for each of the library peptides and they are substantially similar to those set forth hereinabove in conjunction with the description of the library peptides that include a structure according to Formula I. For those library peptides having a structure according to Formula IV, the value of c is independently selected for each of the library peptides and it is a member selected from the group consisting of the integers from 0 to 6.

In a further preferred embodiment, the invention provides a library of peptides having structures independently selected from peptides according to Formula VIII, and more preferably Formula IX.

As discussed above, each of the peptide sequences and peptide lengths of the peptides of a particular library are independently selected. Thus, in a preferred embodiment, each of peptides of the library is characterized by a peptide sequence that is different than the peptide sequence of each of the other peptides. The difference resides in peptide sequence, peptide length or both. Thus, a preferred library of the invention is one wherein, an amino acid residue selected from at least one member of $AA^1, AA^2 \ldots AA^i$ of the first peptide is a different amino acid residue than an amino acid residue at a corresponding position relative to $AA^1$ of the second peptide.

The peptide libraries of the invention are broadly characterized by the presence of peptides of diverse structure within the library. In an exemplary embodiment, the diversity in the peptides of the library is provided by peptide sequences that have different amino acid residues at $AA^1$. Those of skill in the art will appreciate that the focus of the present discussion on diversity at $AA^1$ is for clarity of illustration and is not intended to exclude those peptide sequences having diversity at positions other than $AA^1$ or those peptide sequences having diversity at positions in addition to $R^1$.

Thus, in a preferred embodiment, the library is characterized by having at least six peptides having different peptide sequences wherein, $AA^1$ is a different amino acid residue in each of the different peptide sequences. In another preferred embodiment, the library includes at least twelve peptides, and more preferably twenty peptides having different peptide sequences, in which $AA^1$ is a different amino acid residue in each of the different peptide sequences.

The amino acid residue at $AA^1$ can be any amino acid residue selected from the group consisting of natural amino acids, unnatural amino acids and modified amino acids. In a preferred embodiment, $AA^1$ is a member selected from the group consisting of Lys, Arg, Leu and combinations thereof.

The peptides of the library can have a peptide sequence of substantially any useful length for a selected purpose. Presently preferred peptide sequences are those in which J is a member selected from the numbers from 4 to 8.

Many processes have been devised for the synthesis of libraries of peptides and peptide analogs, which are applicable to practicing the present invention (see, for example, Gordon and Kerwin, COMBINATORIAL CHEMISTRY AND MOLECULAR DIVERSITY IN DRUG DISCOVERY, Wiley-Liss, New York, 1998).

Libraries of peptides and certain types of peptide mimetics, called "peptoids", have been assembled and screened for a desirable biological activity by a range of methodologies (see, Gordon et al., *J. Med Chem.*, 37: 1385–1401 (1994). For example, the method of Geysen, (*Bioorg. Med. Chem. Letters*, 3: 397–404 (1993); *Proc. Natl. Acad Sci. USA*, 81: 3998 (1984)) employs a modification of Merrifield peptide synthesis, wherein the C-terminal amino acid residues of the peptides to be synthesized are linked to solid-support particles shaped as polyethylene pins; these pins are treated individually or collectively in sequence to introduce additional amino-acid residues forming the desired peptides. The peptides are then screened for activity without removing them from the pins. The solid support of the invention can be similarly formed and used as a solid support for the synthesis of peptide libraries or other libraries.

Houghton, *Proc. Natl. Acad. Sci. USA*, 82: 5131 (1985); Eichler et al., *Biochemistry*, 32: 11035–11041 (1993); and U.S. Pat. No. 4,631,211) utilize individual polyethylene bags ("tea bags") containing C-terminal amino acids bound to a solid support. These are mixed and coupled with the requisite amino acids using solid phase synthesis techniques. The peptides produced are then recovered and tested individually.

Fodor et al., *Science*, 251: 767 (1991), describe light-directed, spatially addressable parallel-peptide synthesis on a silicon wafer to generate large arrays of addressable peptides that can be directly tested for binding to biological targets. The solid support of the invention can be utilized in a similar manner.

In another combinatorial approach, equally applicable to the present invention, Huebner et al. (U.S. Pat. No. 5,182,366) discloses functionalized polystyrene beads divided into portions, each of which is acylated with a desired amino acid; the bead portions are mixed together, then divided into portions each of which is re-subjected to acylation with a second amino acid producing dipeptides. By using this synthetic scheme, exponentially increasing numbers of peptides are produced in uniform amounts, which are then separately screened for a biological activity of interest.

Presently preferred uses for the peptide libraries of the invention include their use in probing the reactivity and substrate specificity of enzymes, and in particular proteases. Thus, preferred libraries are those in which at least one peptide sequence of the library is cleavable by a protease into a fluorescent moiety and the peptide sequence, or a fragment of the peptide sequence.

The present invention provides techniques for preparing and probing peptide libraries having a wide range of sizes. Thus, in a preferred embodiment, the library includes at least 10 peptides, wherein each of the peptide sequences is a different peptide sequence. More preferably, the library includes at least 100 peptides, wherein each of the peptide sequences is a different peptide sequence, more preferably at least 1,000 peptides, still more preferably, at least 10,000 peptides, more preferably, at least 100,000 peptides, and even still more preferably, at least 1,000,000 peptides.

In another preferred embodiment, the library of the invention is provided with a means by which a library member (e.g., peptide sequence) can be resolved from the other library members. Many such means for deconvoluting a library of compounds are known in the art, including, for example, the use of tags, positional libraries, and ordered arrays. Thus, in a preferred embodiment, the library of the invention has a first member located at a first region of a substrate and a second member located at a second region of a substrate.

Libraries in a positional or an ordered array motif are presently preferred. Such libraries permit the identification of peptides, or other compounds, that are associated with zones of activity located during screening the library. Specifically, the library can be ordered so that the position of the peptide on the array corresponds to the identity of the peptide. Thus, once an assay has been carried out, and the position on the array determined for an active peptide, the identity of that peptide can be easily ascertained.

In another preferred embodiment, the present invention provides a library in a microarray format comprising n compounds distributed over n regions of a substrate. Preferably, each of the n compounds is a different compound. In a still further preferred embodiment, the n compounds are patterned on the substrate in a manner that allows the identity of the compound at each of the n locations to be ascertained. The microarray is patterned from essentially any type of fluorogenic molecule of the invention, including, but not limited to, small organic molecules, peptides, nucleic acids, carbohydrates, antibodies, enzymes, and the like.

A variety of methods are currently available for making arrays of biological molecules, such as arrays of antibodies, nucleic acid molecules, peptides or proteins. The following discussion utilizes a DNA microarray as an exemplary microarray. This use of DNA is intended to be illustrative and not limiting. One of skill in the art will appreciate that the following discussion is substantially applicable to forming microarrays of other fluorogenic compounds of the invention as well.

One method for making ordered arrays of compounds on a porous membrane is a "dot blot" approach. In this method, a vacuum manifold transfers a plurality, e.g., 96, aqueous samples of a compound from 3 millimeter diameter wells to a porous membrane. A common variant of this procedure is a "slot-blot" method in which the wells have highly-elongated oval shapes.

The compound is immobilized on the porous membrane by, for example, baking the membrane or exposing it to UV radiation. This is a manual procedure practical for making one array at a time and usually limited to 96 samples per array.

A more efficient technique employed for making ordered arrays of compounds uses an array of pins dipped into the wells, e.g., the 96 wells of a microtitre plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39–81 (1990).

An alternate method of creating ordered arrays of compounds is described by Pirrung et al. U.S. Pat. No. 5,143,854, issued 1992), and also by Fodor et al., (*Science,* 251: 767–773 (1991)) for preparing arrays of nucleic acid sequences. The method involves synthesizing different compounds at different discrete regions of a substrate. A related method has been described by Southern et al. (*Genomics,* 13: 1008–1017 (1992)).

Khrapko, et al., *DNA Sequence,* 1: 375–388 (1991) describes a method of making a compound matrix by spotting DNA onto a thin layer of polyacrylamide. The spotting is done manually with a micropipette.

When the library is associated with a substrate, the substrate can also be patterned using techniques such as photolithography (Kleinfield et al., *J. Neurosci.* 8:4098–120 (1998)), photoetching, chemical etching and microcontact printing (Kumar et al., Langmuir 10:1498–511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y.; Whitesides, G., *J. Am. Chem. Soc.* 117:3274–75 (1995). Similarly, using photolithography, patterns with features as small as 1 µm have been produced. See, Hickman et al., *J. Vac. Sci. Technol.* 12:607–16 (1994).

The pattern can be printed directly onto the substrate or, alternatively, a "lift off" technique can be utilized. In the lift off technique, a patterned resist is laid onto the substrate, a compound is laid down in those areas not covered by the resist and the resist is subsequently removed. Resists appropriate for use with the substrates of the present invention are known to those of skill in the art. See, for example, Kleinfield et al., *J. Neurosci.* 8:4098–120 (1998). Following removal of the photoresist, a second compound, having a structure different from the first compound can be bonded to the substrate on those areas initially covered by the resist. Using this technique, substrates with patterns having regions of different chemical characteristics can be produced. Thus, for example, a pattern having an array of adjacent wells can be created by varying the hydrophobicity/hydrophilicity, charge and other chemical characteristics of the pattern constituents. In one embodiment, hydrophilic compounds can be confined to individual wells by patterning walls using hydrophobic materials. Similar substrate configurations are accessible through microprinting a layer with the desired characteristics directly onto the substrate. See, Mrkish, M.; Whitesides, G. M., *Ann. Rev. Biophys. Biomol. Struct.* 25:55–78 (1996).

Sequence Specificity Database

As high-resolution, high-sensitivity enzyme sequence specificity and datasets become available to the art, significant progress in the areas of diagnostics, therapeutics, drug development, biosensor development, and other related areas is possible. For example, disease markers can be identified and utilized for better confirmation of a disease condition or stage (see, U.S. Pat. Nos. 5,672,480; 5,599,677; 5,939,533; and 5,710,007). Subcellular toxicological information can be generated to better direct drug structure and activity correlation (see, Anderson, L., "Pharmaceutical Proteomics: Targets, Mechanism, and Function," paper presented at the IBC Proteomics conference, Coronado, Calif. (June 11–12, 1998)). Subcellular toxicological information can also be utilized in a biological sensor device to predict the likely toxicological effect of chemical exposures and likely tolerable exposure thresholds (see, U.S. Pat. No. 5,811,231). Similar advantages accrue from datasets relevant to other biomolecules and bioactive agents (e.g., nucleic acids, saccharides, lipids, drugs, and the like).

Thus, in another preferred embodiment, the present invention provides a database that includes at least one set of peptide sequence specificity data for an enzyme, preferably a protease. The data contained in the database is acquired using a method of the invention and/or a fluorogenic species of the invention either singly or in a library format. The database can be in substantially any form in which data can be maintained and transmitted, but is preferably an electronic database. The electronic database of the invention can be maintained on any electronic device allowing for the storage of and access to the database, such as a personal computer, but is preferably distributed on a wide area network, such as the World Wide Web.

The focus of the present section on databases including peptide sequence specificity data is for clarity of illustration only. It will be apparent to those of skill in the art that similar databases can be assembled for any of the fluorogenic compounds or libraries of compounds of the invention.

The compositions and methods described herein for identifying and/or quantitating the relative and/or absolute abundance of a variety of molecular and macromolecular species from a biological sample provide an abundance of information, which can be correlated with pathological conditions, predisposition to disease, drug testing, therapeutic monitoring, gene-disease causal linkages, identification of correlates of immunity and physiological status, among others. As the large amounts of raw data generated by these methods are poorly suited for manual review and analysis without prior data processing using high-speed computers, several methods for indexing and retrieving biomolecular information have been proposed. For example, U.S. Pat.

Nos. 6,023,659 and 5,966,712 disclose a relational database system for storing biomolecular sequence information in a manner that allows sequences to be catalogued and searched according to one or more protein function hierarchies. U.S. Pat. No. 5,953,727 discloses a relational database having sequence records containing information in a format that allows a collection of partial-length DNA sequences to be catalogued and searched according to association with one or more sequencing projects for obtaining full-length sequences from the collection of partial length sequences. U.S. Pat. No. 5,706,498 discloses a gene database retrieval system for making a retrieval of a gene sequence similar to a sequence data item in a gene database based on the degree of similarity between a key sequence and a target sequence. U.S. Pat. No. 5,538,897 discloses a method using mass spectroscopy fragmentation patterns of peptides to identify amino acid sequences in computer databases by comparison of predicted mass spectra with experimentally-derived mass spectra using a closeness-of-fit measure. U.S. Pat. No. 5,926,818 discloses a multi-dimensional database comprising a functionality for multi-dimensional data analysis described as on-line analytical processing (OLAP), which entails the consolidation of projected and actual data according to more than one consolidation path or dimension. U.S. Pat. No. 5,295,261 reports a hybrid database structure in which the fields of each database record are divided into two classes, navigational and informational data, with navigational fields stored in a hierarchical topological map which can be viewed as a tree structure or as the merger of two or more such tree structures.

The present invention provides a method for producing a computer database comprising a computer and software for storing in computer-retrievable form a collection of enzyme peptide sequence specificity records cross-tabulated, for example, with data specifying the source of the protein-containing sample from which each sequence specificity record was obtained.

In a preferred embodiment, at least one of the sources of protein-containing sample is from a tissue sample known to be free of pathological disorders. In a variation, at least one of the sources is a known pathological tissue specimen, for example, a neoplastic lesion or a tissue specimen containing an infectious agent such as a virus, or the like. In another variation, the sequence specificity records cross-tabulate one or more of the following parameters for each protein species in a sample: (1) a unique identification code, which can comprise a peptide sequence specificity and/or characteristic separation coordinate (e.g., electrophoretic coordinates); (2) sample source; (3) absolute and/or relative quantity of the protein species present in the sample; (4) presence or absence of amine- or carboxy-terminal post-translational modifications; and (5) original amino acid sequence, electrophoresis and/or mass spectral data, and the like, used to identify the proteins.

The invention also provides for the storage and retrieval of a collection of peptide sequence specificities in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays. Typically, the peptide sequence specificity records are stored as a bit pattern in an array of magnetic domains on a magnetizable medium or as an array of charge states or transistor gate states, such as an array of cells in a DRAM device (e.g., each cell comprised of a transistor and a charge storage area, which may be on the transistor). In one embodiment, the invention provides such storage devices, and computer systems built therewith, comprising a bit pattern encoding a protein expression fingerprint record comprising unique identifiers for at least 10 protein species cross-tabulated with sample source.

The invention preferably provides a method for identifying related peptide sequences, comprising performing a computerized comparison between a peptide sequence specificity stored in or retrieved from a computer storage device or database and at least one other sequence; such comparison can comprise a sequence analysis or comparison algorithm or computer program embodiment thereof (e.g., FASTA, TFASTA, GAP, BESTFIT) and/or the comparison may be of the relative amount of a peptide sequence in a pool of sequences determined from a polypeptide sample of a specimen. The invention provides a computer system comprising a storage device having a bit pattern encoding a database having at least 100 protein expression fingerprint records obtained by the methods of the invention, and a program for sequence alignment and comparison to predetermined genetic or protein sequences.

The invention also preferably provides a magnetic disk, such as an IBM-compatible (DOS, Windows, Windows95/ 98/2000, Windows NT, OS/2) or other format (e.g., Linux, SunOS, Solaris, AIX, SCO Unix, VMS, MV, Macintosh, etc.) floppy diskette or hard (fixed, Winchester) disk drive, comprising a bit pattern encoding a protein expression fingerprint record; often the disk will comprise at least one other bit pattern encoding a polynucleotide and/or polypeptide sequence other than a peptide sequence record of the invention, typically in a file format suitable for retrieval and processing in a computerized sequence analysis, comparison, or relative quantitation method.

The invention also provides a network, comprising a plurality of computing devices linked via a data link, such as an Ethernet cable (coax or 10BaseT), telephone line, ISDN line, wireless network, optical fiber, or other suitable signal tranmission medium, whereby at least one network device (e.g., computer, disk array, etc.) comprises a pattern of magnetic domains (e.g., magnetic disk) and/or charge domains (e.g., an array of DRAM cells) composing a bit pattern encoding a protein expression fingerprint record of the invention.

The invention also provides a method for transmitting a peptide sequence specificity record of the invention that includes generating an electronic signal on an electronic communications device, such as a modem, ISDN terminal adapter, DSL, cable modem, ATM switch, or the like, wherein the signal includes (in native or encrypted format) a bit pattern encoding a peptide sequence specificity record or a database comprising a plurality of peptide sequence specificity records obtained by the method of the invention.

In a preferred embodiment, the invention provides a computer system for comparing a query polypeptide sequence or query peptide sequence specificity to a database containing an array of data structures, such as a peptide sequence specificity record obtained by the method of the invention, and ranking database sequences based on the degree of sequence identity and gap weight to the query sequence. A central processor is initialized to load and execute the computer program for alignment and/or comparison of the amino acid sequences. A query sequence including at least 2 amino acids or 6 nucleotides encoding 2 amino acids is entered into the central processor via an I/O device. Execution of the computer program results in the central processor retrieving the sequence data from the data file, which comprises a binary description of a peptide sequence specificity record or portion thereof containing polypeptide sequence data for the record.

The sequence data or record and the computer program can be transferred to secondary memory, which is typically random access memory (e.g., DRAM, SRAM, SGRAM, or SDRAM). Sequences are ranked according to the degree of sequence identity to the query sequence and results are output via an I/O device. For example, a central processor can be a conventional computer (e.g., Intel Pentium, PowerPC, Alpha, PA-8000, SPARC, MIPS 4400, MIPS 10000, VAX, etc.); a program can be a commercial or public domain molecular biology software package (e.g., UWGCG Sequence Analysis Software, Darwin); a data file can be an optical or magnetic disk, a data server, a memory device (e.g., DRAM, SRAM, SGRAM, SDRAM, EPROM, bubble memory, flash memory, etc.); an I/O device can be a terminal comprising a video display and a keyboard, a modem, an ISDN terminal adapter, an Ethernet port, a punched card reader, a magnetic strip reader, or other suitable I/O device.

In another preferred embodiment, the invention provides a computer program for comparing query polypeptide sequence(s) or query polynucleotide sequence(s) to a peptide sequence specificity database obtained by a method of the invention and ranking database sequences based on the degree of similarity of protein species expressed and relative and/or absolute abundance in a sample. The initial step is input of a query peptide sequence, or peptide sequence specificity record obtained by a method of the invention, input via an I/O device. A data file is accessed in to retrieve a collection of peptide sequence specificity records for comparison to the query. Individually or collectively sequences or other cross-tabulated information of the peptide sequence specificity collection are optimally matched to the query sequence(s), such as by the algorithm of Needleman and Wunsch or the algorithm of Smith and Waterman or another suitable algorithm obtainable by those skilled in the art.

Once aligned or matched, the percentage of sequence similarity can be computed for each aligned or matched sequence to generate a similarity value for each sequence or peptide sequence specificity record collection as compared to the query sequence(s). Sequences are generally ranked in order of greatest sequence identity or weighted match to the query sequence, and the relative ranking of the sequence to the best matches in the collection of records is thus generated. A determination is made; if more sequences records exist in the data file, the additional sequences or a subset thereof are retrieved and the process is iterated. If no additional sequences exist in the data file, the rank ordered sequences are output via an I/O device, thereby displaying the relative ranking of sequences among the sequences of the data file optimally matched and compared to the query sequence(s).

The invention also preferably provides the use of a computer system, such as that described above, which comprises: (1) a computer; (2) a stored bit pattern encoding a collection of peptide sequence specificity records obtained by the methods of the invention, which may be stored in the computer; (3) a comparison sequence, such as a query sequence; and (4) a program for alignment and comparison, typically with rank-ordering of comparison results on the basis of computed similarity values.

In a preferred embodiment, neural network pattern matching/recognition software is trained to identify and match peptide sequence specificity records based on back-propagation using empirical data input by a user. The computer system and methods described herein permit the identification of the relative relationship of a query peptide sequence specificity to a collection of peptide sequence specificities; preferably peptide sequence specificities (query and database) are obtained by the methods of the invention.

The invention also provides a computer system including a database containing a plurality of peptide sequence specificity records in the form of tree-based or otherwise hierarchical navigational fields cross-tabulated to informational data such as one or more or the following: medical records, patient medical history, medical diagnostic test results of a patient, patient name, patient sex, patient age, patient genetic profile, patient diagnosis-related group code, patient therapy, time of day, vital signs of a patient, drug assay results of a patient, medical information of patient's blood relatives, and other similar medical, biological, and physiological information of a patient from which the sample(s) used to generate the peptide sequence specificity record was obtained.

In a preferred embodiment, a computer system comprising a database having a hybrid data structure with the navigational field(s) comprising a peptide sequence specificity obtained by a method of the invention is employed to link to informational fields of the same or a related record which comprise medical information as described herein; the data structure can conform to the general description in U.S. Pat. No. 5,295,261, which is incorporated herein by reference.

The invention also preferably provides a computer system, including a computer and a program employing a neural network trained to extract database records having a predicted or predetermined peptide sequence specificity match that is pathognomonic for a predetermined disease or medical condition, predisposition to disease, or physiological state. In an illustrative embodiment, a blood or cellular sample from a patient is analyzed according to a method of the invention to provide a predetermined peptide sequence specificity that is entered as a database query into a trained neural network that has been previously trained on a plurality of predetermined database records to establish correlative neural relationships between peptide sequence specificity (navigation fields) and medical data (information field(s)), so that the query identifies the medical condition(s) most highly correlated in the trained neural network with a peptide sequence specificity. The method can alternatively, or in addition, employ a predetermined peptide sequence specificity record obtained from serum, blood, or other cellular sample to query a database of sequence specificity profile records using a trained neural network which links the query metabolite profile record to the database records linked to the medical condition(s) most highly correlated in the trained neural network with the patient's peptide sequence specificity.

The invention also preferably provides a computer system, including a computer and a program employing a database comprising records having a field or plurality of fields including, for example, a peptide sequence specificity data set obtained from a serum, blood, or other cellular sample of a patient and analyzed according to a method of the present invention, and further having one or a plurality of fields containing data obtained from a patient relating to symptoms, medical status, medical history, or other differential diagnosis information, which can be entered via a connection to the Internet or other TCP/IP or related networking system.

Kits

The present invention also provides for kits for the detection of a selected species (e.g., enzyme, nucleic acid, etc.) or activity (e.g., enzymatic, hybridization, etc.) in samples. The kits comprise one or more containers containing the fluorogenic compounds ("indicators") of the present invention. The fluorogenic compounds may be provided in solution or bound to a solid support. Thus, the kits may contain indicator solutions or indicator "dipsticks", blotters, culture media, and the like. The kits may also contain indicator cartridges (where the fluorogenic compound is bound to a solid support) for use in automated protease activity detectors.

The kits additionally may include an instruction manual that teaches a method of the invention and describes the use of the components of the kit. In addition, the kits may also include other reagents, buffers, various concentrations of enzyme inhibitors, stock enzymes (for generation of standard curves, etc), culture media, disposable cuvettes and the like to aid the detection of protease activity utilizing the fluorogenic protease indicators of the present invention.

It will be appreciated that kits may additionally, or alternatively, include any of the other indicators described herein (e.g., nucleic acid based indicators, oligosaccharide indicators, lipid indicators, etc.).

In another embodiment, the kit contains a solid support of the invention and, optionally, directions for using the solid support for preparing a fluorogenic compound. The kit may also contain reagents, buffers, etc. useful in preparing a fluorogenic conjugate of the invention.

Methods

Protease Assay

The assays of the invention are illustrated by the following discussion focusing on protease assays. The focus of this discussion is for clarity of illustration and should not be interpreted as limiting the scope of the invention to assays of proteases. Those of skill in the art will appreciate that the broad range of compounds that can be produced using the solid support of the present invention can be assayed using methods known in the art or modifications on those methods that are well within the abilities of one of skill in the art.

Proteases represent a number of families of proteolytic enzymes that catalytically hydrolyze peptide bonds. Principal groups of proteases include metalloproteases, serine proteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and can be characterized by alterations in the activity of specific proteases and their inhibitors. For example emphysema, arthritis, thrombosis, cancer metastasis and some forms of hemophilia result from the lack of regulation of serine protease activities (see, for example, TEXTBOOK OF BIOCHEMISTRY WITH CLINICAL CORRELATIONS, John Wiley and Sons, Inc. N.Y. (1993)). In case of viral infection, the presence of viral proteases have been identified in infected cells. Such viral proteases include, for example, HIV protease associated with AIDS and NS3 protease associated with Hepatitis C. These viral proteases play a critical role in the virus life cycle.

Proteases have also been implicated in cancer metastasis. Increased synthesis of the protease urokinase has been correlated with an increased ability to metastasize in many cancers. Urokinase activates plasmin from plasminogen which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. *Adv. Cancer. Res.*, 44: 139 (1985)).

Human mast cells express at least four distinct tryptases, designated α βI, βII, and βIII. These enzymes are not controlled by blood plasma proteinase inhibitors and only cleave a few physiological substrates in vitro. The tryptase family of serine proteases has been implicated in a variety of allergic and inflammatory diseases involving mast cells because of elevated tryptase levels found in biological fluids from patients with these disorders. However, the exact role of tryptase in the pathophysiology of disease remains to be delineated. The scope of biological functions and corresponding physiological consequences of tryptase are substantially defined by their substrate specificity.

Tryptase is a potent activator of pro-urokinase plasminogen activator (uPA), the zymogen form of a protease associated with tumor metastasis and invasion. Activation of the plasminogen cascade, resulting in the destruction of extracellular matrix for cellular extravasation and migration, may be a function of tryptase activation of prourokinase plasminogen activator at the P4-P1 sequence of Pro-Arg-Phe-Lys (Stack, et al., *Journal of Biological Chemistry* 269(13): 9416–9419 (1994)). Vasoactive intestinal peptide, a neuropeptide that is implicated in the regulation of vascular permeability, is also cleaved by tryptase, primarily at the Thr-Arg-Leu-Arg sequence (Tam, et al., *Am. J. Respir. Cell Mol. Biol.* 3: 27–32 (1990)). The G-protein coupled receptor PAR-2 can be cleaved and activated by tryptase at the Ser-Lys-Gly-Arg sequence to drive fibroblast proliferation, whereas the thrombin activated receptor PAR-1 is inactivated by tryptase at the Pro-Asn-Asp-Lys sequence (Molino et al., *Journal of Biological Chemistry* 272(7): 4043–4049 (1997)). Taken together, this evidence suggests a central role for tryptase in tissue remodeling as a consequence of disease. This is consistent with the profound changes observed in several mast cell-mediated disorders. One hallmark of chronic asthma and other long-term respiratory diseases is fibrosis and thickening of the underlying tissues that could be the result of tryptase activation of its physiological targets. Similarly, a series of reports during the past year have shown angiogenesis to be associated with mast cell density, tryptase activity and poor prognosis in a variety of cancers (Coussens et al., *Genes and Development* 13(11): 1382–97 (1999)); Takanami et al., *Cancer* 88(12): 2686–92 (2000); Toth-Jakatics et al., *Human Pathology* 31(8): 955–960 (2000); Ribatti et al., *International Journal of Cancer* 85(2): 171–5 (2000)).

Tryptase has been recognized as a viable drug target, and therapeutically useful inhibitors have been under development by several pharmaceutical companies, some even taking advantage of the bifunctional active site (Burgess et al., *Proceedings of the National Academy of Sciences* 96(15): 8348–52 (1999); Rice et al., *Curr Pharm Des* 4(5): 381–96 (1998)). Insights gained from the modeling of the optimal sequence into the active site will support further development of novel selective substrates of β-tryptases that will enhance our understanding of the pathophysiology of these enzymes, as well as lead to the development of new and effective inhibitors.

Clearly, measurement of changes in the activity of specific proteases is clinically significant in the treatment and management of the underlying disease states. Proteases, however, are not easy to assay. Typical approaches include ELISA using antibodies that bind the protease or RIA using various labeled substrates; with their natural substrates assays are difficult to perform and expensive. With currently available synthetic substrates the assays are expensive, insensitive and nonselective. In addition, many "indicator" substrates require high quantities of protease which results, in part, in the self destruction of the protease.

Thus, in a preferred embodiment, the invention provides a method of assaying for the presence of an enzymatically active protease in a sample. The method includes: (a) contacting the sample with a material according to Formula II, in such a manner whereby the fluorogenic moiety is released from the peptide sequence upon action of the protease, thereby producing a fluorescent moiety; and (b) observing whether the sample undergoes a detectable change in fluorescence, the detectable change being an indication of the presence of the enzymatically active protease in the sample.

The method of the invention can be used to assay for substantially any known or later discovered enzyme and is of particular use in assaying for a protease. The sample containing the protease can be derived from substantially any source, or organism. In a preferred embodiment, the sample is a clinical sample from a subject. In a presently preferred embodiment, the protease is a member selected from the group consisting of aspartic protease, cysteine protease, metalloprotease and serine protease. The method of the invention is particularly preferred for the assay of proteases derived from a microorganism, including, but not limited to, bacteria, fingi, yeast, viruses, and protozoa.

In an illustrative application, the fluorogenic molecules of this invention are used to assay the activity of purified protease made up as a reagent (e.g. in a buffer solution) for experimental or industrial use. Like many other enzymes, proteases may loose activity over time, especially when they are stored as their active forms. In addition, many proteases exist naturally in an inactive precursor form (e.g. a zymogen), which itself must be activated by hydrolysis of a particular peptide bond to produce the active form of the enzyme prior to use. Because the degree of activation is variable and because proteases may loose activity over time, it is often desirable to verify that the protease is active and to often quantify the activity before using a particular protease in a particular application.

Assaying for protease activity of a stock solution simply requires adding a quantity of the stock solution to a fluorogenic protease indicator of the present invention and measuring the subsequent increase in fluorescence or decrease in excitation band in the absorption spectrum. The stock solution and the fluorogenic indicator may also be combined and assayed in a "digestion buffer" that optimizes activity of the protease. Buffers suitable for assaying protease activity are well known to those of skill in the art. In general, a buffer will be selected whose pH corresponds to the pH optimum of the particular protease. For example, a buffer particularly suitable for assaying elastase activity consists of 50 mM sodium phosphate, 1 mM EDTA at pH 8.9. The measurement is most easily made in a fluorometer, and instrument that provides an "excitation" light source for the fluorophore and then measures the light subsequently emitted at a particular wavelength. Comparison with a control indicator solution lacking the protease provides a measure of the protease activity. The activity level may be precisely quantified by generating a standard curve for the protease/indicator combination in which the rate of change in fluorescence produced by protease solutions of known activity is determined.

While detection of the fluorogenic compounds is preferably accomplished using a fluorometer, detection may by a variety of other methods well known to those of skill in the art. Thus, for example, since the fluorophores of the present invention emit in the visible wavelengths, detection may be simply by visual inspection of fluorescence in response to excitation by a light source. Detection may also be by means of an image analysis system utilizing a video camera interfaced to a digitizer or other image acquisition system. Detection may also be by visualization through a filter, as under a fluorescence microscope. The microscope may provide a signal that is simply visualized by the operator. Alternatively, the signal may be recorded on photographic film or using a video analysis system. The signal may also simply be quantified in realtime using either an image analysis system or a photometer.

Thus, for example, a basic assay for protease activity of a sample will involve suspending or dissolving the sample in a buffer (at the pH optima of the particular protease being assayed), adding to the buffer one of the fluorogenic protease indicators of the present invention, and monitoring the resulting change in fluorescence using a spectrofluorometer. The spectrofluorometer will be set to excite the fluorophore at the excitation wavelength of the fluorophore and to detect the resulting fluorescence at the emission wavelength of the fluorophore.

Previous approaches to verifying or quantifying protease activity involve combining an aliquot of the protease with its substrate, allowing a period of time for digestion to occur and then measuring the amount of digested protein, most typically by HPLC. This approach is time consuming, utilizes expensive reagents, requires a number of steps and entails a considerable amount of labor. In contrast, the fluorogenic reagents of the present invention allow rapid determination of protease activity in a matter of minutes in a single-step procedure. An aliquot of the protease to be tested is simply added to, or contacted with, the fluorogenic reagents of this invention and the subsequent change in fluorescence is monitored (e.g., using a fluorometer or a fluorescence microplate reader).

In addition to determining protease activity in "reagent" solutions, the fluorogenic compositions of the present invention may be utilized to detect protease activity in biological samples. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

In one embodiment, the present invention provides for methods of detecting protease activity in an isolated biological sample. This may be determined by simply contacting the sample with a fluorogenic protease "indicator" of the present invention and monitoring the change in fluorescence of the "indicator" over time. The sample may be suspended in a "digestion buffer" as described above. The sample may also be cleared of cellular debris, e.g. by centrifugation before analysis.

In another embodiment, this invention provides for a method of detecting in situ protease activity in histological sections. This method of detecting protease activity in tissues offers significant advantages over prior art methods (e.g. specific stains, antibody labels, etc.) because, unlike simple labeling approaches, in situ assays using the protease indicators indicate actual activity rather than simple presence or absence of the protease. Proteases are often present in tissues in their inactive precursor (zymogen) forms which are capable of binding protease labels. Thus, traditional labeling approaches provide no information regarding the physiological state, vis a vis protease activity, of the tissue.

The in situ assay method generally comprises providing a tissue section (preferably a frozen section, as fixation or embedding may destroy protease activity in the sample), contacting the section with one of the fluorogenic peptides of the present invention, and visualizing the resulting fluorescence. Visualization is preferably accomplished utilizing a fluorescence microscope. The fluorescence microscope provides an "excitation" light source to induce fluorescence of the fluorophore. The microscope is typically equipped with filters to optimize detection of the resulting fluorescence. As indicated above, the microscope may be equipped with a camera, photometer, or image acquisition system.

The fluorogenic peptide can be introduced to the sections in a number of ways. For example, the fluorogenic peptide may be provided in a buffer solution, as described above, which is applied to the tissue section. Alternatively, the fluorogenic peptide may be provided as a semi-solid medium such as a gel or agar which is spread over the tissue sample. The gel helps to hold moisture in the sample while providing a signal in response to protease activity. The fluorogenic peptide may also be provided conjugated to a polymer such as a plastic film which may be used in procedures similar to the development of Western Blots. The plastic film is placed over the tissue sample on the slide and the fluorescence resulting from cleaved indicator molecules is viewed in the sample tissue under a microscope.

Typically the tissue sample is incubated for a period of time sufficient to allow a protease to cleave the fluorogenic peptide. Incubation times will generally range from about 10 to 60 minutes at temperatures up to and including 37° C.

In yet another embodiment, this invention provides for a method of detecting in situ enzymatic activity of cells in culture or cell suspensions derived from tissues, biopsy samples, or biological fluids (e.g., saliva, blood, urine, lymph, plasma, etc.). In an illustrative embodiment, the cultured cells are grown either on chamber slides or in suspension and then transferred to histology slides by cytocentrifugation. Similarly, the cell suspensions are prepared according to standard methods and transferred to histology slides. The slide is washed with phosphate buffered saline and coated with a semi-solid polymer or a solution containing the fluorogenic protease indicator. The slide is incubated at 37° C. for a time sufficient for a protease to cleave the protease "indicator". The slide is then examined under a fluorescence microscope equipped with the appropriate filters, as described above.

Alternatively, the cells are incubated with the fluorogenic peptide at 37° C., then washed with buffer and transferred to a glass capillary tube and examined under a fluorescence microscope. When a flow cytometer is used to quantitate the intracellular enzyme activity, the cells with the fluorogenic "indicator" is simply diluted with buffer after 37° C. incubation and analyzed.

Previously described fluorogenic protease indicators typically absorb light in the ultraviolet range (e.g., Wang et al., *Tetrahedron Lett.* 31:6493 (1990)). They are thus unsuitable for sensitive detection of protease activity in biological samples which typically contain constituents (e.g., proteins) that absorb in the ultraviolet range. In contrast, the fluorescent indicators of the present invention both absorb and emit in the visible range (400 nm to about 750 nm). These signals are, therefore, not readily quenched by, or otherwise interfered with by background molecules; therefore, they are easily detected in biological samples.

In an illustrative embodiment, the invention provides a library useful for profiling of various serine and cysteine proteases. The library is able to distinguish proteases having specificity for P1-acidic amino acids (granzyme B), P1-large hydrophobic (chymotrypsin), P1-small hydrophobic (human neutrophil elastase), P1-basic amino acids (trypsin, thrombin, plasmin) and P1-multiple amino acids (papain and cruzain) (FIG. 2).

In another illustrative embodiment, the invention provides a library for probing the extended substrate specificity of several serine proteases involved in blood coagulation, in which the P1 position is held constant as either Lys or Arg, depending on the preferred P1-specificity of the protease. Thrombin, plasmin, uPA, tPA and factor Xa (FIGS. 3A–E) display profiles consistent with knowledge about their specificity.

The invention also provides a library for probing the extended substrate specificity of the cysteine proteases, papain and cruzain, having P1-positioned libraries including peptides having hydrophobic amino acids in the P2 position.

The PS-SCL strategy provided by the present invention allows for the rapid and facile determination of proteolytic substrate specificity. Those of skill in the art will appreciate that the present invention provides a wide variety of alternative library formats. For example, fixing the P2-position as a large hydrophobic amino acid may circumvent preferential internal cleavage by papain-fold proteases and lead to proper register of the substrate. Determination and consideration of particular limitations relevant to any particular enzyme or method of substrate specificity determination are within the ability of those of skill in the art.

In addition to its use in assaying for the presence of a selected enzyme, the method of the invention is also useful for detecting, identifying and quantifying an enzyme (e.g., protease). Thus, in another preferred embodiment, the method further includes, (c) quantifying the fluorescent moiety, thereby quantifying the protease.

In yet another preferred embodiment, the invention provides a method of assaying for the presence of an enzyme, for example, an enzymatically active protease in a sample using a peptide of the invention having a structure according to Formula VI. The method includes: (a) contacting the sample with a material according to Formula VI, in such a manner whereby the fluorogenic moiety is released from the peptide sequence upon action of the protease, thereby producing a fluorescent moiety; and (b) observing whether the sample undergoes a detectable change in fluorescence, the detectable change being an indication of the presence of the enzymatically active protease in the sample. Preferred embodiments of this method are substantially similar to those set forth for the method using the material according to Formula II.

In a preferred embodiment of the above-described method, the method further includes, (d) quantifying the fluorescent moiety, thereby quantifying the protease.

Protease Sequence Specificity Assay

In another preferred embodiment, the present invention provides a method of determining the sequence specificity of an enzyme, and preferably of an enzymatically active protease. The method includes: (a) contacting the protease with a library of peptides of the invention in such a manner whereby the fluorogenic moiety is released from the peptide sequence, thereby forming a fluorescent moiety; (b) detecting the fluorescent moiety; and (c) determining the sequence of the peptide sequence, thereby determining the peptide sequence specificity profile of the protease.

In a preferred embodiment of the above-described method, the method further includes, (d) quantifying the fluorescent moiety, thereby quantifying the protease.

Microorganism Assay

In a further preferred embodiment, the invention provides a method of assaying for the presence of a selected microorganism in a sample by probing the sequence specificity of an enzyme or other molecule produced or utilized by the microorganism. In an illustrative embodiment, the enzyme is a protease, which mediates peptide cleavage by the microorganism of one or more peptides of the invention. The method includes: (a) contacting a sample suspected of containing the selected microorganism with a material according to Formula VII, wherein the peptide comprises a sequence that is selectively cleaved by a protease of the selected microorganism, thereby releasing the fluorogenic moiety from the peptide sequence; and (b) detecting the cleavage by detecting fluorescence arising from a fluorescent moiety produced by cleavage of the fluorogenic moiety from the peptide sequence, thereby confirming the presence of the selected microorganism in the sample. The preferred embodiments of the present method are substantially similar to those described in conjunction with the protease assay, supra.

In yet another preferred embodiment, the invention provides a method of assaying for the presence of a selected microorganism in a sample by probing the sequence specificity of peptide cleavage by a protease of the microorganism using a peptide of the invention having a structure according to Formula VII. The method includes: (a) contacting a sample suspected of containing the selected microorganism with a peptide according to Formula VII. The peptide comprises a sequence that is selectively cleaved by a protease of a selected microorganism, thereby releasing the fluorogenic moiety from the peptide sequence; and (b) detecting the cleavage by detecting fluorescence arising from a fluorescent moiety produced by cleavage of the fluorogenic moiety from the peptide sequence, thereby confirming the presence of the selected microorganism in the sample.

In a preferred embodiment of the above-described method, the method further includes, (d) quantifying the fluorescent moiety, thereby quantifying the protease, the microorganism or both.

The above-described method is useful to determine whether an unknown microorganism contains an enzyme that acts on a peptide of the invention to liberate a fluorescent moiety, and it may be include within or utilized in conjunction with a device in which identification of an unknown microorganism is made on the basis of its enzyme content (see, for example, Mize, U.S. Pat. No. 5,055,594).

The methods of the invention are also useful for determining the effect of an agent, such as an antimicrobial agent on a microorganism. Thus, the invention can, for example, take the form of a process for determining the minimum inhibitory concentration (MIC) of an antimicrobial substance with respect to a microorganism under study (e.g., a clinical septic isolate). In an illustrative embodiment, a microorganism is treated with an antimicrobial agent that inhibits or destroys an enzyme or other molecule necessary for the growth and/or reproduction of the organism. The effect of the antimicrobial agent on the microorganism is probed by contacting the microorganism with one or more of the fluorogenic peptides of the invention. A change in the ability of the enzyme of the microorganism to produce a fluorescent material from the fluorogenic peptide is indicative of the activity of the antimicrobial agent. The magnitude of the effect, can be ascertained by quantitating the fluorescence and comparing it to a selected benchmark, such as the magnitude of fluorescence arising from contacting the microorganism with a peptide of the invention in the absence of an antimicrobial agent (see, for example, Carr et al, U.S. Pat. No. 5,064,756, and U.S. Pat. No. 5,079,144).

In the above-recited methods, the exposure to the fluorogenic peptide to the microorganisms lasts for a sufficient time to let the enzymatic reaction take place. The fluorescence of each sample is assessed (e.g., by a non-destructive instrumental fluorometric or fluoroscopic method).

Moreover, in each of the aspects and embodiments set forth hereinabove, the protease can be substantially any protease of interest, but is preferably a member selected from the group consisting of aspartic protease, cysteine protease, metalloprotease and serine protease. The protease assayed using a method of the invention can be derived from substantially any organism, including, but not limited to mammals, birds, reptiles, insects, plants, fungi and the like. In a preferred embodiment, the protease is derived from a microorganism, including, but not limited to, bacteria, fungi, yeast, viruses, and protozoa.

Fluorogenic Peptide Synthesis

Those of skill in the art will recognize that many methods can be used to prepare the peptides and the libraries of the invention. In an exemplary embodiment (see, FIG. 1), the fluorogenic leaving group of the invention is synthesized by condensing an N-Fmoc coumarin derivative 2, to acid-labile Rink linker to provide ACC resin 3. After Fmoc-removal to produce free amine 4, natural, unnatural and modified amino acids can be coupled to the aniline efficiently to produce 5, which can be elaborated by the coupling of additional amino acids to form 6, for example. After the synthesis of the peptide is complete, the peptide-fluorogenic moiety conjugate can be cleaved from the solid support to form 7 or, alternatively, the conjugate can remain tethered to the solid support.

Thus, in a further preferred embodiment, the present invention provides a method of preparing a fluorogenic peptide or a material including a fluorogenic peptide. The method includes: (a) providing a first conjugate comprising a fluorogenic moiety covalently bonded to a solid support, the conjugate having a structure according to Formula I wherein, at least one of $R^1$, $R^2$, $R^3$, $R^4$, $R^5$ and $R^6$ is —$NH_2$; (b) contacting the first conjugate with a first protected amino acid moiety ($pAA^1$) and an activating agent, thereby forming a peptide bond between a carboxyl group of $pAA^1$ and the aniline nitrogen of the first conjugate; (c) deprotecting the $pAA^1$, thereby forming a second conjugate having a reactive $AA^1$ amine moiety; (d) contacting the second conjugate with a second protected amino acid ($pAA^2$) and an activating agent, thereby forming a peptide bond between a carboxyl group of pAA2 and the reactive $AA^1$ amine moiety; and (e) deprotecting the $pAA^2$, thereby forming a third conjugate having a reactive $AA^2$ amine moiety.

In a preferred embodiment, the method further includes: (f) contacting the third conjugate with a third protected amino acid ($pAA^3$) and an activating agent, thereby forming a peptide bond between a carboxyl group of $pAA^3$ and the reactive $AA^2$ amine moiety; and (e) deprotecting the $pAA^3$, thereby forming a fourth conjugate having a reactive $AA^3$ amine moiety.

For amino acids that are difficult to couple (Ile, Val, etc), free, unreacted aniline may remain on the support and complicate subsequent synthesis and assay operations. A specialized capping step employing the 3-nitrotriazole active ester of acetic acid in DMF efficiently acylates the remaining aniline. The resulting acetic acid-capped coumarin that may be present in unpurified substrate solutions is generally not a protease substrate. P1-substituted resins that are provided by these methods can be used to prepare any ACC-fluorogenic substrate.

Thus, in yet another preferred embodiment, the method further includes, between steps (b) and (c), capping substantially all of the aniline amine groups that have not reacted with $pAA^1$. The capping step can use any reagent system that includes an amine-reactive component. In a preferred embodiment, the capping step utilizes a mixture comprising an active ester of a carboxylic acid, such as, for example, the nitrotriazole ester of acetic acid.

In a further preferred embodiment, diversity at any particular position or combination of positions is introduced by utilizing a mixture of at least two, preferably at least 6, more preferably at least 12 and more preferably still, at least 20, amino acids to grow the peptide chain. Thus, a member selected from the group consisting of $pAA^1$, $pAA^2$, $pAA^3$ and combinations thereof includes a mixture of protected amino acids differing in the identity of the amino acid portion of the protected amino acids. The mixtures of amino acids can include of any useful amount of a particular amino acid in combination with any useful amount of one or more different amino acids. In a presently preferred embodiment, the mixture is an isokinetic mixture of amino acids.

Solid phase peptide synthesis in which the C-terminal amino acid of the sequence is attached to an insoluble support followed by sequential addition of the remaining amino acids in the sequence is the preferred method for preparing the peptide backbone of the compounds of the present invention. Techniques for solid phase synthesis are described by Barany and Merrifield, Solid-Phase Peptide Synthesis; pp. 3–284 in The Peptides: Analysis, Synthesis, Biology. Vol. 2; SPECIAL METHODS IN PEPTIDE SYNTHESIS, Part A., Gross and Meienhofer, eds. Academic press, N.Y., 1980; and Stewart et al., SOLID PHASE PEPTIDE SYNTHESIS, 2nd ed. Pierce Chem. Co., Rockford, Ill. (1984) which are incorporated herein by reference. Solid phase synthesis is most easily accomplished with commercially available peptide synthesizers utilizing Fmoc or t-BOC chemistry. The chemical synthesis of the peptide component of a fluorogenic protease indicator is described in detail in Examples 3, 4 and 5.

In a particularly preferred embodiment, peptide synthesis is performed using Fmoc synthesis chemistry. The side chains of Asp, Ser, Thr and Tyr are preferably protected using t-butyl and the side chain of Cys residue using S-trityl and S-t-butylthio, and Lys residues are preferably protected using t-Boc, Fmoc and 4-methyltrityl for lysine residues. Appropriately protected amino acid reagents are commercially available or can be prepared using art-recognized methods. The use of multiple protecting groups allows selective deblocking and coupling of a fluorophore to any particular desired side chain. Thus, for example, t-Boc deprotection is accomplished using TFA in dichloromethane. Fmoc deprotection is accomplished using, for example, 20% (v/v) piperidine in DMF or N-methylpyrolidone, and 4-methyltrityl deprotection is accomplished using, for example, 1 to 5% (v/v) TFA in water or 1% TFA and 5% triisopropylsilane in DCM. S-t-butylthio deprotection is accomplished using, for example, aqueous mercaptoethanol (10%). Removal of t-butyl, t-boc and S-trityl groups is accomplished using, for example, TFA:phenol:water:thioanisol:ethanedithiol (85:5:5:2.5:2.5), or TFA:phenol:water (95:5:5). Detailed synthesis, deprotection and fluorophore coupling protocols are provided in the Examples herein.

The materials and methods of the present invention are further illustrated by the examples which follow. These examples are offered to illustrate, but not to limit the claimed invention.

EXAMPLES

Materials and Methods

Reagents and General Methods

Rink Amide AM resin and Fmoc-amino acids were purchased from Novabiochem (San Diego, Calif.). The amine substitution level of the Rink resin (0.80 meq/gram) determined by a spectrophotometric Fmoc-quantitation assay (Bunin, B. A., (1998) The Combinatorial Index (Academic Press, San Diego). Anhydrous DMF, EM Science (Hawthorne, N.Y.). HATU was purchased from Perseptive Biosystems (Foster City, Calif.). DICI, HOBt, AcOH, Fmoc-Cl, TFA, collidine, and TIS were purchased from Aldrich (Milwaukee, Wis.). Argonaut Quest 210 Organic Synthesizer was used to prepare Fmoc-P1-substituted ACC resins. Library synthesis was performed in 96-well plates using the Multi-Chem synthesis apparatus of Robbins Scientific (Sunnyvale, Calif.). Human thrombin, plasmin, and factor Xa were used as received, and were purchased from Haematologic Technologies Inc. (Essex Jct., Vt.). Human light chain uPA, and neutrophil elastase were used as received, and were purchased from Calbiochem (San Diego, Calif.). Rat granzyme B was expressed and purified as described (Harris, J. L., et al., (1998) Journal of Biological Chemistry 273:27364–73). Cruzain was expressed and purified as described (Eakin, A. E., et al., (1992) Journal of Biological Chemistry 267:7411–20). Rat trypsin was expressed and purified as described (Halfon, S., et al., (1996) Journal of the American Chemical Society 118:1227–1228). DNA-modifying enzymes were obtained from Promega (Madison, Wis.). The Pichia pastoris expression system was purchased from Invitrogen (San Diego, Calif.). Native human lung tryptase was purchased from ICN (Aurora, Ohio). Factor Xa was purchased from New England Biolabs (Beverly, Mass.). tPA and uPA were purchased from American Diagnostica (Greenwich, Conn.). Heparin and other biochemicals were purchased from Sigma. Substrates in the positional scanning synthetic combinatorial libraries as well as the single substrates Ac-PRNK-ACC, Ac-PANK-ACC, PRTK-ACC, Ac-PRNR-ACC, Ac-GTAR-ACC, Ac-QFAR-ACC, Ac-KQWK-ACC, and Ac-nTPR-ACC were prepared as previously described (9). Ac-PRNK-cmk was synthesized by Enzyme Systems Products (Livermore, Calif.).

Example 1

This Example sets forth the synthesis of 7-Fmoc-aminocoumarin-4-acetic acid, a precursor to the solid support of the invention.

1.1 ACC-resin Synthesis 1.1a Synthesis of 7-Fmoc-aminocoumarin-4-acetic acid

7-Fmoc-aminocoumarin-4-acetic acid was prepared by treating 7-aminocoumarin-4-acetic acid (14, 15) with Fmoc-Cl. 7-aminocoumarin-4-acetic acid (10.0 g, 45.6 mmol) and $H_2O$ (228 mL) were mixed. $NaHCO_3$ (3.92 g, 45.6 mmol) was added in small portions followed by the addition of acetone (228 mL). The solution was cooled with an ice bath, and Fmoc-Cl (10.7 g, 41.5 mmol) was added with vigorous stirring over the course of an hour. The ice bath was removed and the solution stirred overnight. The acetone was removed with rotary evaporation and the resulting gummy solid was collected via filtration and washed with several portions of hexane. The material was dried over $P_2O_5$ to give 14.6 g (80%) of cream-colored solid: $^1$H NMR (400 MHz) δ 3.86 (s, 2), 4.33 (t, 1, J=6.2), 4.55 (d, 2, J=6.2), 6.34 (s, 1), 7.33–7.44 (m, 5), 7.56 (s, 1), 7.61 (d, 1, J=8.6), 7.76 (d, 2, J=7.3), 7.91 (d, 2, J=7.4), 10.23 (s, 1), 12.84 (s, 1); $^{13}$C (101 MHz) δ 37.9, 47.4, 66.8, 67.2, 105.5, 114.6, 115.3, 121.1, 125.9, 126.9, 128.0, 128.6, 141.6, 143.6, 144.5, 150.7, 154.1, 154.8, 160.8, 171.4.

Example 2

Example 2 sets forth an illustrative synthesis of a solid support of the invention and the functionalization of the solid support with a single amino acid residue.

2.1 Synthesis of ACC Resin

ACC-resin was prepared by condensation of Rink Amide AM resin with 7-Fmoc-aminocoumarin-4-acetic acid. Rink Amide AM resin (21 g, 17 mmol) was solvated with DMF (200 mL). The mixture was agitated for 30 min and filtered with a filter cannula (Pharmacia, Uppsala, Sweden) whereupon 20% piperidine in DMF (200 mL) was added. After agitating 25 min, the resin was filtered and washed with DMF (3×200 mL). 7-Fmoc-aminocoumarin-4-acetic acid (15 g, 34 mmol), HOBt (4.6 g, 34 mmol), and DMF (150 mL) were added, followed by the addition of DICI (5.3 mL, 34 mmol). The mixture was agitated overnight, filtered, washed (DMF: 3×200 mL, THF: 3×200 mL, MeOH: 3×200 mL), and dried over $P_2O_5$. The substitution level of the resin was 0.58 mmol/g (>95%) as determined by Fmoc-analysis (Bunin, B. A., (1998) *The Combinatorial Index* (Academic Press, San Diego).

2.2 Synthesis of P1-substituted ACC-resin Synthesis

Fmoc-ACC-Resin (100 mg, 0.058 mmol) was added to 20 reaction vessels of an Argonaut Quest 210 Organic Synthesizer and solvated with DMF (2 mL). The resin was filtered and 20% piperidine in DMF (2 mL) was added to each vessel. After agitating for 25 min, the resin was filtered and washed with DMF (3×2 mL). An Fmoc-amino acid (0.29 mmol), DMF (0.7 mmol), collidine (76 µL, 0.58 mmol) and HATU (110 mg, 0.29 mmol) were added to the designated reaction vessel followed by agitation for 20 h. The resins were then filtered, washed with DMF (3×2 mL), and subjected a second time to the coupling conditions. A solution of AcOH (40 µL, 0.70 mmol), DICI (110 µL, 0.70 mmol), nitrotriazole (80 mg, 0.70 mmol) in DMF (0.7 mL) was added to each of the reaction vessels followed by agitation over a 24 h period. The resins were filtered, washed (DMF: 3×2 mL; THF: 3×2 mL; MeOH: 3×2 mL), and dried over $P_2O_5$. The substitution level of each resin[‡] was determined by Fmoc-analysis (Bunin, B. A., (1998) *The Combinatorial Index* (Academic Press, San Diego).

[‡] Fmoc-amino acid, coupling efficiency, (double coupling). Fmoc-Ala-OH, >95%; Fmoc-Arg(Pbf)-OH, 73%, (80%); Fmoc-Asn(Trt)-OH, >95%; Fmoc-Asp(O-t-Bu)-OH, >95%; Fmoc-Glu(O-t-Bu)-OH, 77%, (>95%); Fmoc-Gln-(Trt)-OH, 73%, (>95%); Fmoc-Gly-OH, >95%; Fmoc-His(Trt)-OH, 72%, (>95%); Fmoc-Ile-OH, 57%, (60%); Fmoc-Leu-OH, 86%, (>95%); Fmoc-Lys(Boc)-OH, 75%, (>95%); Fmoc-Met-OH, 94%, (>95%); Fmoc-Nle-OH, 83%, (>95%); Fmoc-Phe-OH, >95%; Fmoc-Pro-OH, 63%, (70%); Fmoc-Ser(O-t-Bu)-OH, 85%, (>95%); Fmoc-Thr(O-t-Bu)-OH, 73%, (84%); Fmoc-Trp(Boc)-OH, 77%, (>95%); Fmoc-Tyr(O-t-Bu)-OH, 86%, (>95%); Fmoc-Val-OH, 69%, (80%).

Example 3

Example 3 sets forth the synthesis and screening of libraries of the invention.

3.1 P1-diverse Library 3.1a Synthesis

Individual P1-substituted Fmoc-amino acid ACC-resin (ca. 25 mg, 0.013 mmol) was added to wells of a Multi-Chem 96-well reaction apparatus. The resin-containing wells were solvated with DMF (0.5 mL). A 20% piperidine in DMF solution (0.5 mL) was added followed by agitation for 30 min. The wells of the reaction block were filtered and washed with DMF (3×0.5 mL). In order to introduce the randomized P2 position, an isokinetic mixture (Ostresh, J. M., et al., (1994) *Biopolymers* 34:1681–9) of Fmoc-amino acids (4.8 mmol, 10 equiv/well; Fmoc-amino acid, mol %: Fmoc-Ala-OH, 3.4; Fmoc-Arg(Pbf)-OH, 6.5; Fmoc-Asn (Trt)-OH, 5.3; Fmoc-Asp(O-t-Bu)-OH, 3.5; Fmoc-Glu(O-t-Bu)-OH, 3.6; Fmoc-Gln(Trt)-OH, 5.3; Fmoc-Gly-OH, 2.9; Fmoc-His(Trt)-OH, 3.5; Fmoc-Ile-OH, 17.4; Fmoc-Leu-OH, 4.9; Fmoc-Lys(Boc)-OH, 6.2; Fmoc-Nle-OH, 3.8; Fmoc-Phe-OH, 2.5; Fmoc-Pro-OH, 4.3; Fmoc-Ser(O-t-Bu)-OH, 2.8; Fmoc-Thr(O-t-Bu)-OH, 4.8; Fmoc-Trp(Boc)-OH, 3.8; Fmoc-Tyr(O-t-Bu)-OH, 4.1; Fmoc-Val-OH, 11.3) was pre-activated with DICI (390 µL, 2.5 mmol), and HOBt (340 mg, 2.5 mmol) in DMF (10 mL). The solution (0.5 mL) was added to each of the wells. The reaction block was agitated for 3 h, filtered, and washed with DMF (3×0.5 mL). The randomized P3 and P4 positions were incorporated in the same manner. The Fmoc of the P4 amino acid was removed and the resin was washed with DMF (3×0.5 mL), and treated with 0.5 mL of a capping solution of AcOH (150 µL, 2.5 mmol), HOBt (340 mg, 2.5 mmol) and DICI (390 µL, 2.5 mmol) in DMF (10 mL). After 4 h of agitation, the resin was washed with DMF (3×0.5 mL), $CH_2Cl_2$ (3×0.5 mL), and treated with a solution of 95:2.5:2.5 TFA/TIS/$H_2O$. After incubating for 1 h the reaction block was opened and placed on a 96 deep-well titer plate and the wells were washed with additional cleavage solution (2×0.5 mL). The collection plate was concentrated, and the substrate-containing wells were diluted with EtOH (0.5 mL) and concentrated twice. The contents of the individual wells were lyophilized from $CH_3CN:H_2O$ mixtures. The total amount of substrate in each well was conservatively estimated to be 0.0063 mmol (50%) based upon yields of single substrates.

3.1b Enzymatic Assay of Library

The concentration of proteolytic enzymes was determined by absorbance measured at 280 nm (Gill, S. C., et al., (1989) *Anal Biochem* 182:319–26). The proportion of catalytically active thrombin, plasmin, tryp sin, uPA, tPA, and chymotryp sin was quantitated by active-site titration with MUGB or MUTMAC (Jameson, G. W., et al., (1973) *Biochemical Journal* 131:107–117).

Substrates from the PS-SCLs were dissolved in DMSO. Approximately $1.0 \times 10^{-9}$ mol of each P1-Lys, P1-Arg, or P1-Leu sub-library (361 compounds) was added to 57 wells of a 96-well microfluor plate (Dynex Technologies, Chantilly, Va.) for a final concentration of 0.1 µM. Approximately $1.0 \times 10^{-10}$ mol of each P1-diverse sub-library (6859 compounds) was added to 20 wells of a 96-well plate for a final concentration of 0.01 µM in each compound. Hydrolysis reactions were initiated by the addition of enzyme (0.02 nM-100 nM) and monitored fluorometrically with a Perkin Elmer LS50B Luminescence Spectrometer, with excitation at 380 nm and emission at 450 nm or 460 nm. Assays of the serine proteases were performed at 25° C. in a buffer containing 50 mM Tris, pH 8.0, 100 mM NaCl, 0-5mM $CaCl_2$, 0.01% Tween-20, and 1% DMSO (from substrates). Assay of the cysteine proteases, papain and cruzain, was performed at 25° C. in a buffer containing 100 mM sodium acetate, pH 5.5, 100 mM NaCl, 5 mM DTT, 1 mM EDTA, 0.01% Brij-35, and 1% DMSO (from substrates).

3.2 Results

3.2a Profilin Proteases with a P1-diverse Library of 137.180 Substrates

Figure 2A:
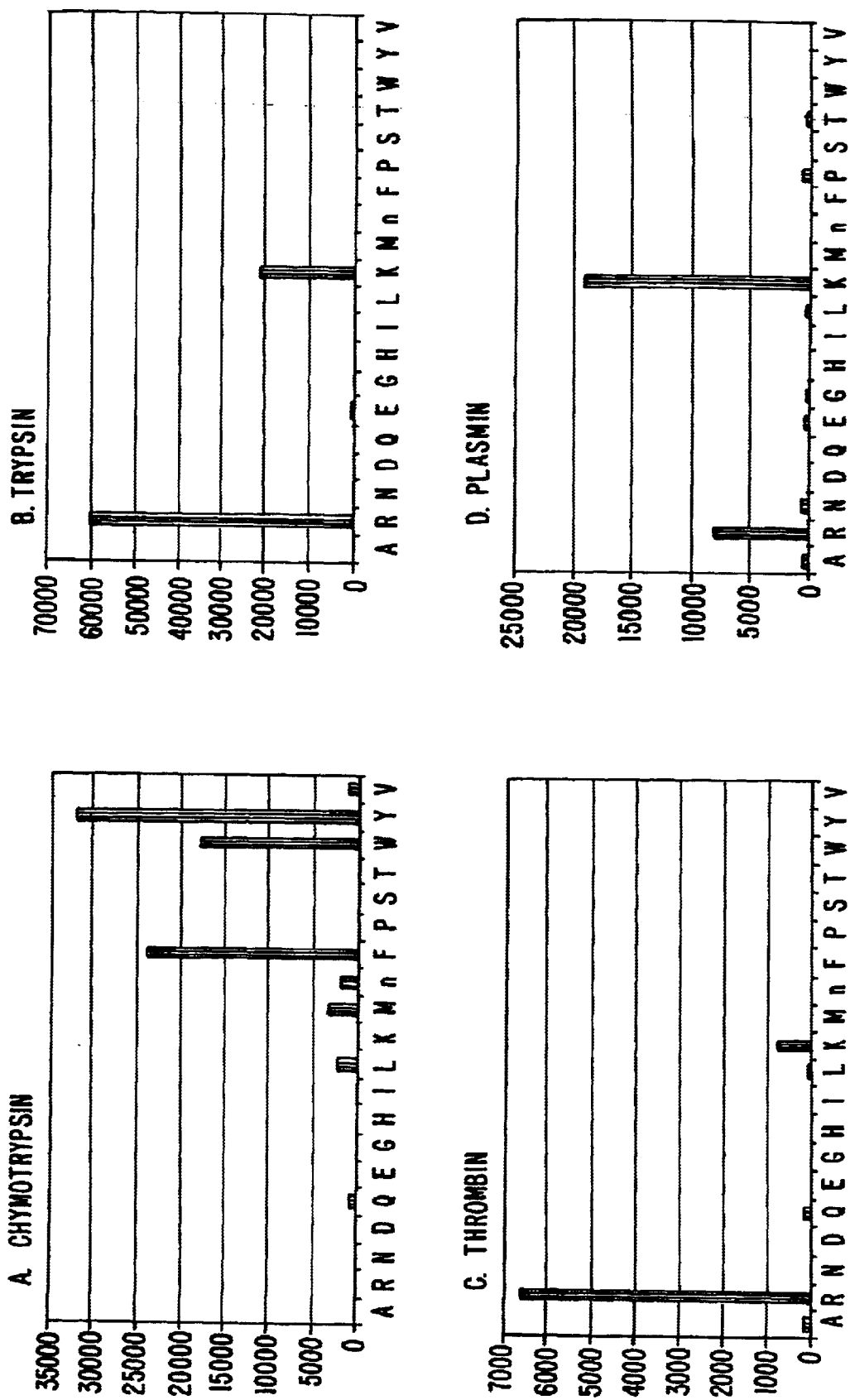
FIG. 2 ACC P1-Diverse Library. The library consists of 20 wells with 6, 859 compounds per well (137,180 compounds total). The Y-axis is the pM of fluorophore released per second. The X-axis provides the spatial address of the amino acid as represented by the one letter code (with "n" representing norleucine). P1-profiles of several serine and cysteine proteases.
Figure 2B:
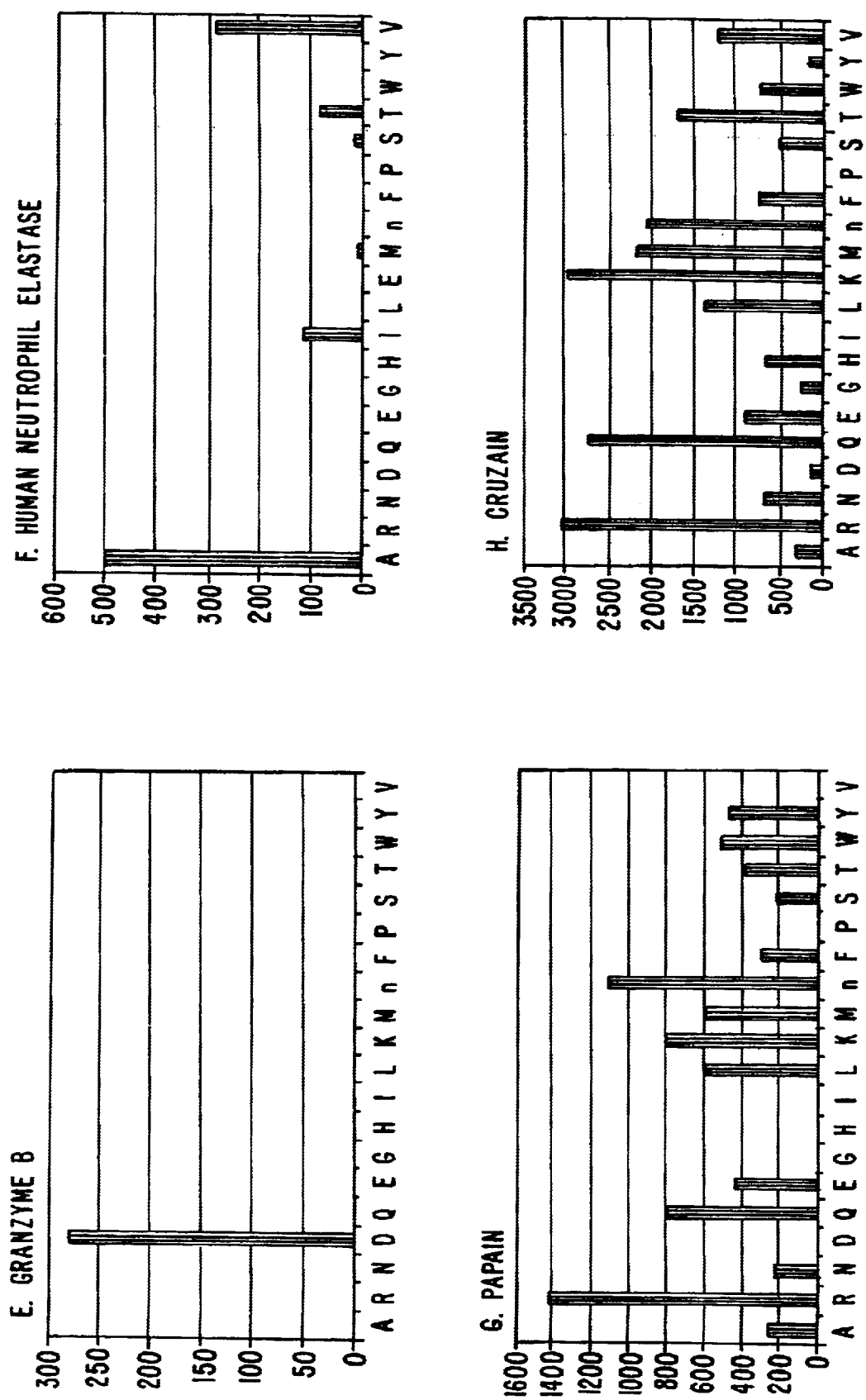

To test the possibility of attaching all amino acids to the P1-site in the substrate a P1-diverse tetrapeptide library was created. The P1-diverse library consists of 20 wells in which only the P1-position is systematically held constant as all amino acids, excluding cysteine and including norleucine. The P2, P3, and P4 positions consist of an equimolar mixture of all amino acids for a total of 6,859 substrate sequences per well. Several serine and cysteine proteases were profiled to test the applicability of this library for the identification of the optimal P1 amino acid. Chymotrypsin showed the expected specificity for large hydrophobic amino acids (FIG. 2A). Trypsin and thrombin showed preference for P1-basic amino acids (Arg>Lys) (FIGS. 2B and 2C). Plasmin also showed a preference for basic amino acids (Lys>Arg) (FIG. 2D). Granzyme B, the only known mammalian serine protease to have P1-Asp specificity, showed a distinct preference for aspartic acid over all other amino acids, including the other acidic amino acid, Glu (FIG. 2E). The P1-profile for human neutrophil elastase has the canonical preference for alanine and valine (FIG. 2F). The cysteine proteases, papain (FIG. 2G) and cruzain (FIG. 2H) showed the broad P1-substrate specificity that is known for these enzymes, although there is a modest preference for arginine.

Example 4

4.1 P1-Fixed Library

4.1a Synthesis

Multi-gram quantities of P1-substituted ACC-resin were synthesized using the methods described herein. Three libraries with the P1-position fixed as Lys, Arg, or Leu were prepared. Fmoc-amino acid-substituted ACC resin (ca. 25 mg, 0.013 mmol, of Lys, Arg, or Leu) was placed in 57 wells of a 96-well reaction block: 3 sublibraries denoted by the second fixed position (P4,P3,P2) of 19 amino acids (cysteine was omitted and norleucine was substituted for methionine). Synthesis, capping and cleavage of the substrates were identical to that described in the previous section, with the exception that for P2, P3 and P4 sublibraries, individual amino acids, rather than isokinetic mixtures, were added to the spatially-addressed P2, P3 or P4 positions.

4.2 Results

4.2a Profiling of Serine Proteases with P1-fixed Positional Libraries

The extended P4-P2 substrate specificity of several serine proteases was profiled with tetrapeptide libraries in which the P1-position was held constant. Three sub-libraries denoting the second fixed position (P4, P3, P2) and consisting of 19 wells addressing a fixed amino acid (Cys was omitted and Nle was substituted for Met) were screened (361 compounds/well and 6,859 compounds/library). Because of the enhanced fluorescence properties of the ACC fluorophore, the concentration of each substrate could be reduced to 0.1 $\mu$M, versus 0.25 $\mu$M for the AMC substrates (Backes, B. J., et al., (2000) *Nature Biotechnology* 18:187–193).

Figure 3A:
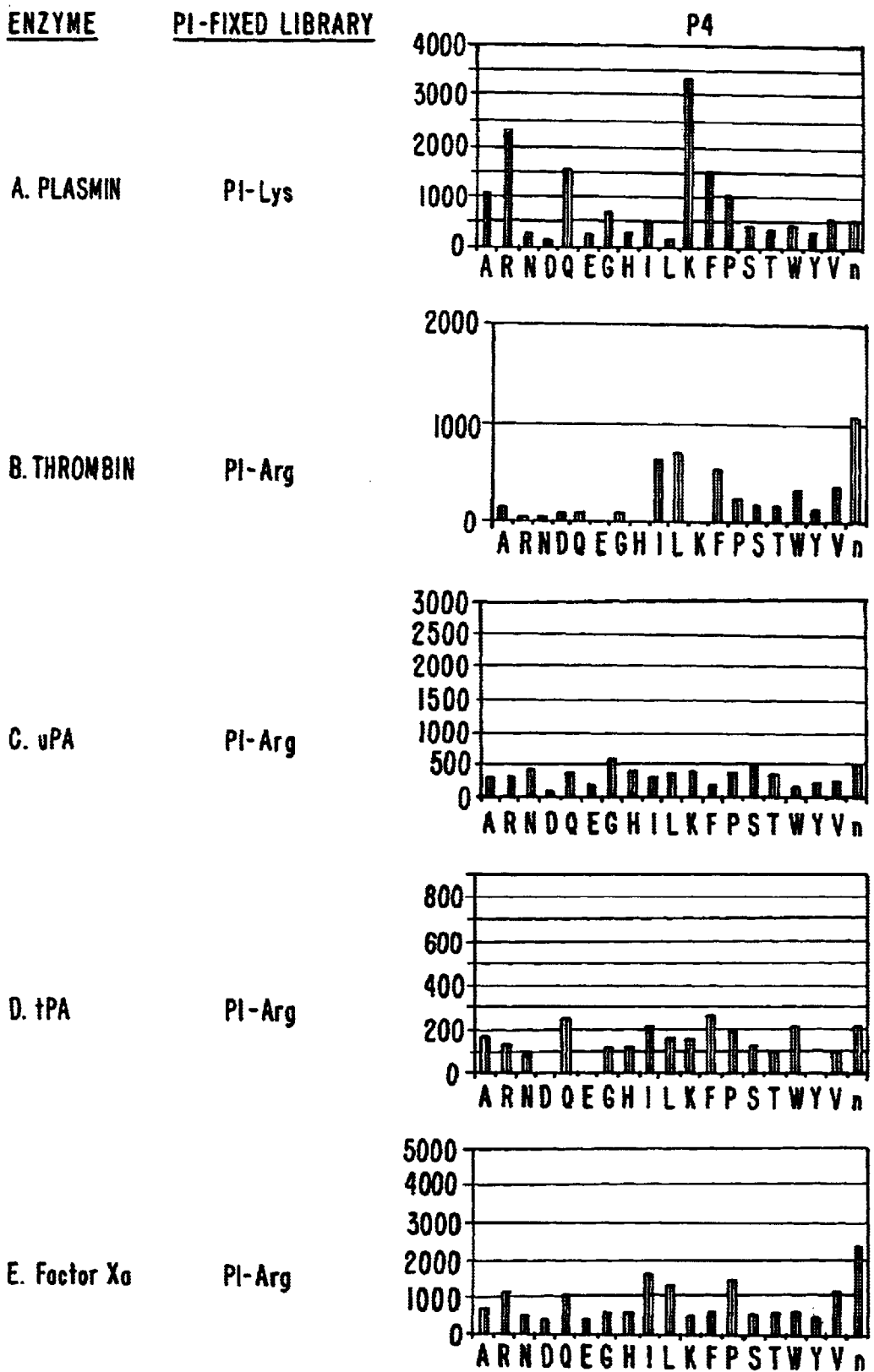
Figure 3B:
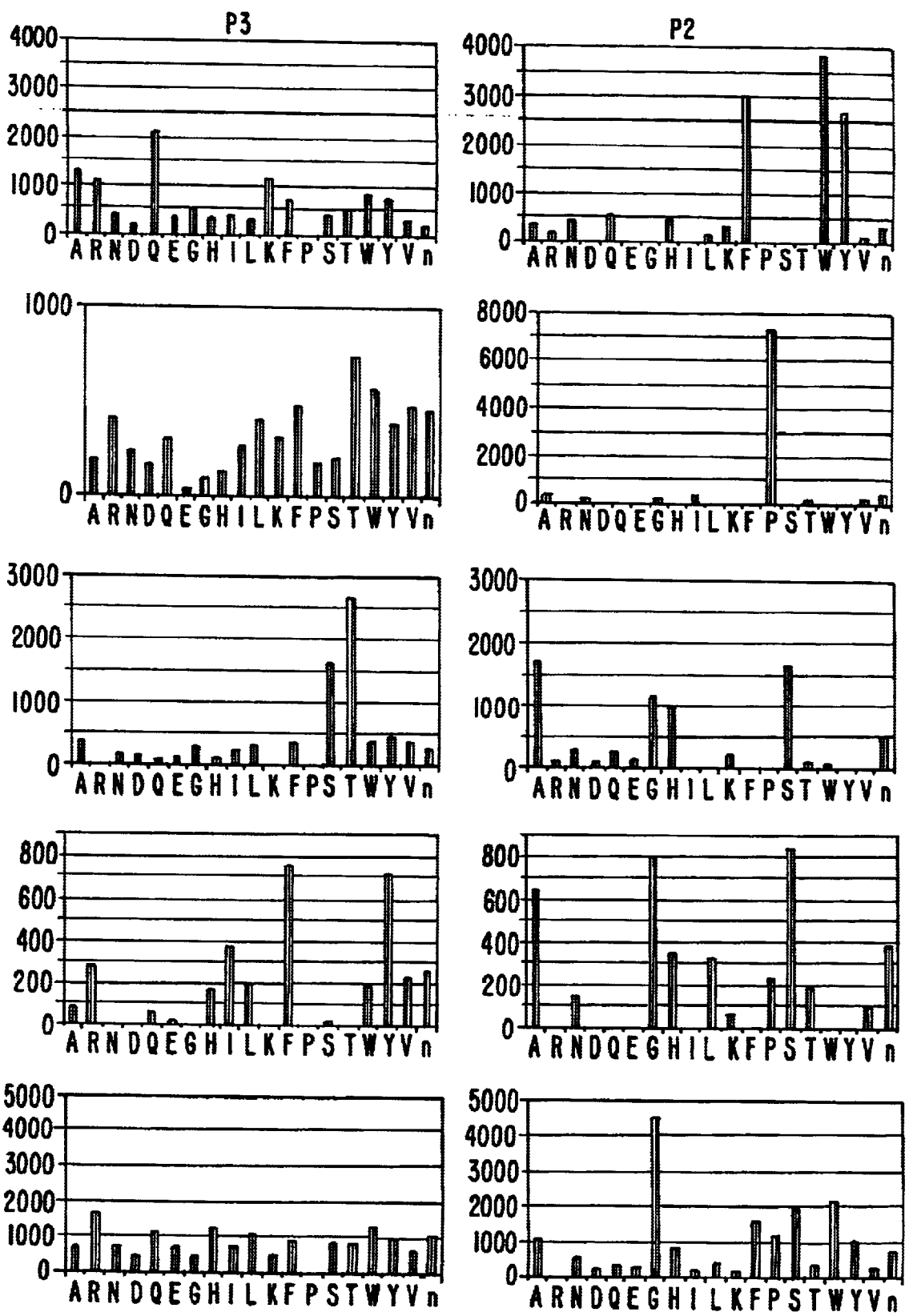

Plasmin, a protease involved in fibrinolysis, has a P1-preference for lysine. Recently, we have shown plasmin to have a distinct preference for aromatic amino acids at the P2 position and lysine at P4 (Backes, B. J., et al., (2000) *Nature Biotechnology* 18:187–193). As is consistent with that data, the substrate specificity profile of plasmin in the ACC P1-fixed lysine library is for P4-lysine, broad P3-specificity, and P2-aromatic amino acids (FIG. 3A).

Thrombin prefers cleavage after P1-arginine to cleavage after P1-lysine. However, the specificity preference of thrombin, when profiled with both the P1-Arg and P1-Lys libraries, shows little difference in the extended subsites (FIG. 3B and Backes, B. J., et al., (2000) *Nature Biotechnology* 18:187–193). Thrombin has a preference for aliphatic amino acids at the P4 position, little preference at P3, and strict preference for proline at the P2-position. Correlation of thrombin's optimal substrate sequence with that found in its physiological substrates has been noted in previous work from this lab (Backes, B. J., et al., (2000) *Nature Biotechnology* 18:187–193).

Figure 3C:
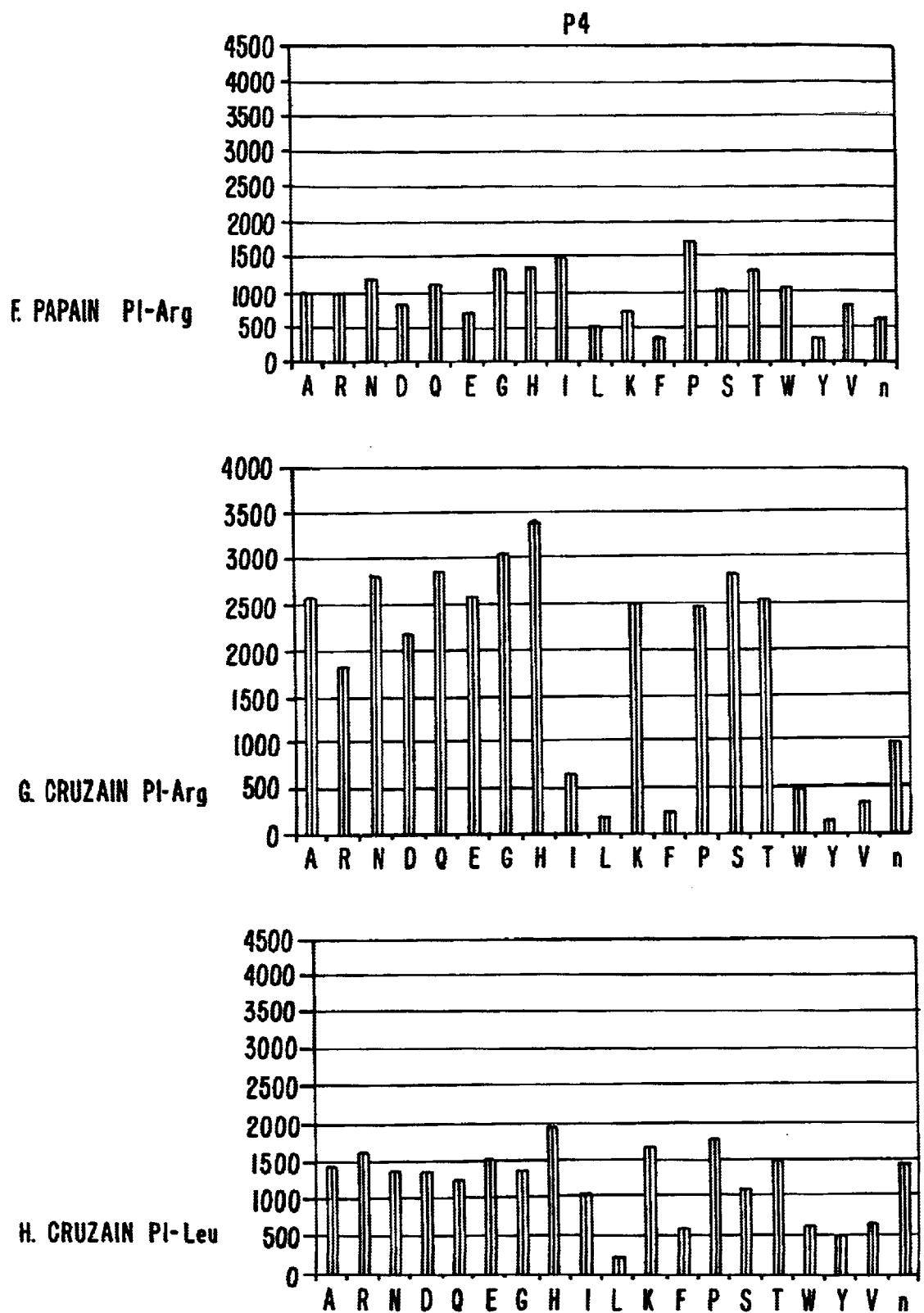

Two enzymes that have been extensively characterized for their extended specificity are tissue-type plasminogen activator (t-PA) (Ding, L., et al., (1995) *Proceedings of the National Academy of Sciences of the United States of America* 92:7627–31; Coombs, G. S., et al., (1996) *Journal of Biological Chemistry* 271:4461–7) and urokinase plasminogen activator (u-PA) (Ke, S. H., et al., (1997) *Journal of Biological Chemistry* 272:16603–9; Ke, S. H., et al., (1997) *Journal of Biological Chemistry* 272:20456–62). Both t-PA and u-PA are responsible for converting plasminogen into active plasmin, and both show high specificity for cleavage after P1-Arg. We observe that both enzymes also show similar preference for small amino acids at P2 (Gly/Ala/Ser) and no significant preference at P4, except for the low activity of acidic amino acids (FIGS. 3C and 3D). In contrast, their P3 preferences are quite disparate with t-PA showing preference for aromatic amino acids (Phe and Tyr) and u-PA for small polar amino acids (Thr and Ser). This difference in P3-specificity was also noted by Ke et al. to be a major distinction between the two-plasminogen activators (Ke, S. H., et al., (1997) *Journal of Biological Chemistry* 272:16603–9).

Factor Xa is an enzyme that plays the critical physiological functions of activating prothrombin and factor VII in the blood coagulation cascade (Davie, E. W., et al., (1991) *Biochemistry* 30:10363–70). Through profiling with the P1-Arg library, we find factor Xa to show a minor preference for P4-aliphatic amino acids, broad substrate specificity in P3, with the absence of P3-proline activity, and a P2-preference for glycine (FIG. 3E). This quantitative information agrees with the qualitative sequences that are efficiently hydrolyzed by factor Xa in a substrate-phage system (2) as well as kinetic studies on tripeptide para-nitroanilide (Cho, K., et al., (1984) *Biochemistry* 23:644–50) and AMC substrates (Cho, K., et al., (1984) *Biochemistry* 23:644–50; Lottenberg, R., et al., (1981) *Methods in Enzymology* 80 Pt C:341–61). Furthermore, the factor Xa P4-P1 cleavage sequence determined here is found in physiologically relevant substrates: the cleavage sequences in prothrombin are Ile-Glu-Gly-Arg and Ile-Asp-Gly-Arg; cleavage sequence in factor VII is Pro-Gln-Gly-Arg; and the cleavage sequence in the autolysis loop of factor Xa is Glu-Lys-Gly-Arg (Brandstetter, H., et al., (1996) *Journal of Biological Chemistry* 271:29988–92).

4.2b Profiling of Cysteine Proteases with P1-fixed Positional Libraries

The positional substrate libraries with the ACC fluorogenic-leaving group are also conducive for defining cysteine protease specificity. The P4-P2 extended substrate specificity for papain and cruzain were defined using the ACC P1-fixed arginine or leucine library. Cysteine proteases of the papain-like class have been shown to have primary substrate specificity at the P2-position (Rawlings, N. D., et al., (1994) *Methods in Enzymology* 244:461–86) rather than the P1-position as is seen in the chymotrypsin-like class of serine proteases. The P2-position usually shows a preference for hydrophobic amino acids. Indeed, we observe papain to have a preference for P2–Val>Phe>Tyr>Nle (FIG. 3F) and cruzain to have a P2-preference for Leu>Tyr>Phe>Val (FIG. 3G). While the P3 specificity is rather broad, papain does show a preference for Pro, whereas cruzain has a preference for the basic amino acids, arginine and lysine. The P4 position is very broad for both enzymes, but interesting observations arise from testing all possible substrates. There is a lack of activity for large aliphatic and aromatic amino acids, the exact amino acids that are preferred in the P2 library. This absence is also seen in a P4 library in which the P1-position is held constant as leucine (FIG. 3H). One possible reason for the observations in the P4 library is that the tetrapeptide substrates are out of register. Cleavage is not occurring at the P1-amido-carbamoylmethyl-coumarin bond, but rather, at the P3-P2 amide bond because the large hydrophobic P4-amino acid binds to the S2-pocket of the enzyme. Incubation of the single substrate Ac-Leu-Thr-Phe-Lys-ACC with cruzain and analysis of the cleavage products confirmed this observation. Product fragments corresponding to cleavage between Thr-Phe were observed (data not shown).

Example 5

Example 5 sets forth the synthesis of single peptide substrates and the kinetic assay of these substrates.
5.1 Single Substrates.
  5.1a Synthesis
  Single substrates for kinetic analysis were prepared employing the methods described in the Examples above. The unpurified products were subjected to reversed-phase HPLC preparatory chromatography followed by lyophilization.
  5.1b Single Substrate Kinetic Assays
  Thrombin concentration ranged from 5–20 nM. The final concentration of substrate ranged from 0.005–2 mM, the concentration of DMSO in the assay was less than 5%. Hydrolysis of AMC and ACC substrates was monitored fluorometrically with an excitation wavelength of 380 nm and emission wavelength of 460 nm on a Fluoromax-2 spectrofluorometer. Cruzain (10 nM) was incubated with 600 $\mu$M of the Ac-Leu-Thr-Phe-Lys-ACC substrate. Aliquots were removed at various time points and applied to a C-18 reverse-phase HPLC column with a 10–40% gradient of 95:4.9:0.1 Acetonitrile:$H_2O$:TFA. MALDI (PE Biosystems Voyager) mass spectrometry data was collected on the HPLC fractions.

Example 6

Example 6 sets forth an experiment designed to investigate the properties of ACC and the overlap of these properties with those of AMC.
6.1 Fluorescence Properties of 7-Amino-4-Carbamoylmethyl-coumarin
  The fluorescence of free ACC and peptidyl-derivatized ACC was detected on a Spex fluorometer thermostated to 25° C. Excitation wavelengths of 300–410 nm, 5 nm intervals, were used with emission wavelengths of 410–500 nm, 5 nm intervals, to determine optimal excitation and emission parameters.
6.2 Results
  6.2a Fluorescence properties of 7-amino-4-carbamoylmethyl-coumarin
  The excitation and emission maxima of the amino-conjugated 7-amino-4-carbamoylmethyl-coumarin (ACC) substrates are 325 nm and 390 nm, respectively (Table I). Cleavage of the substrate by a protease to release the free 7-amino-4-carbamoylmethyl-coumarin results in a shift of the excitation and emission maxima to 350 nm and 450 mn, respectively (Table I). The ACC fluorophore has an approximately 2.8-fold higher fluorescence yield than the AMC coumarin at the excitation and emission wavelengths of 380 nm and 460 nm (Table I). The enhanced fluorescence of the ACC group allows for the more sensitive detection of proteolytic activity.

TABLE I

| Compound | $\lambda_{max, ex}$ (nm) | $\lambda_{max, em}$ (nm) | RFU/nM$_1$ | RFU/nM$_2$ |
|---|---|---|---|---|
| 7-Amino-4-Carbamoylmethyl-coumarin (ACC) | 350 | 450 | 5750 | 4390 |
| 7-Nle-Thr-Pro-Lys-ACC | 325 | 400 | 6.4 | 4.6 |
| 7-Amino-4-Methylcoumarin (AMC) | 340 | 440 | 2600 | 1550 |
| 7-Nle-Thr-Pro-Lys-AMC | 330 | 390 | 3.3 | 2.2 |

1. $\lambda_{ex}$ = 380 nm, $\lambda_{em}$ = 450 nm
2. $\lambda_{ex}$ = 380 nm, $\lambda_{em}$ = 460 nm 6.2b Proteolytic Comparison of ACC and AMC
  To evaluate ACC as a proteolytic leaving group, matched tetrapeptide substrates were made that differed only in the leaving group, ACC or the traditionally used AMC. The two thrombin-susceptible sequences with ACC or AMC, P4-Nle-P3-Thr-P2-Pro-P1-Lys and P4-Leu-P3-Gly-P2-Pro-P1-Lys, showed comparable kinetic constants against thrombin (Table II). A significant advantage of ACC substrates over AMC substrates is the ease of synthesizing ACC substrates over AMC substrates. By employing the synthesis methods described, any amino acid ACC substrate can be prepared rapidly with Fmoc-based synthesis protocols.
  The major difference between the ACC and AMC libraries was the amount of enzyme and substrate required for sufficient fluorescence signal. The substrate concentration for the ACC library was reduced to 0.1 $\mu$M per substrate per well, compared to 0.25 $\mu$M for the AMC library. The enzyme concentration was also reduced. The increased fluorescence sensitivity of the ACC group will be very important for assaying proteases that are available only in limited amounts. For additional validation, specific substrates that differed only in fluorogenic leaving groups, ACC or AMC, were synthesized. Steady state kinetic constants of thrombin were measured for these substrates and shown to be similar for both the ACC and AMC containing substrates (Table II).

TABLE II

| Substrate | $k_{cat}$ (s$^{-1}$) | $K_m$ ($\mu$M) | $k_{cat}/K_m$ ($\mu$M$^{-1}$ s$^{-1}$) |
|---|---|---|---|
| Ac-Nle-Thr-Pro-Lys-AMC | 31.0 ± 0.9 | 115 ± 10 | 0.26 ± 0.03 |
| Ac-Nle-Thr-Pro-Lys--ACC | 33.7 ± 2.7 | 125 ± 13 | 0.28 ± 0.05 |
| Ac-Leu-Gly-Pro-Lys-AMC | 2.3 ± 0.2 | 160 ± 25 | 0.015 ± 0.002 |
| Ac-Leu-Gly-Pro-Lys--ACC | 3.2 ± 0.4 | 195 ± 30 | 0.018 ± 0.003 |

Example 7

7.1 βII Tryptase Gene Construction
  The pPIC9-Hu Try (human βI tryptase plasmid) (Niles et al., *Biotechnology and Applied Biochemistry* 28 (Pt 2): 125–31 (1998)) was subjected to site-directed mutagenesis using the GeneEditor™ in vitro Site-Directed Mutagenesis System (Promega, Madison Wis.). The mutant oligonucleotide 5'-GAGGAGCCGGTGAAGGTCTCCAGCCAC-3' was used to introduce a substitution mutation in the DNA coding for amino acid residue 113 (N113K). Full-length nucleic acid sequencing of both strands confirmed the sequence conversion to the βII tryptase isoform.

7.2 Expression and Purification

Recombinant human βI and βII tryptases were expressed and purified as previously described (Niles (1998)). Briefly, pPIC9-Hu Try/Ni 13K was linearized by Sac I digestion and transformed into the GS115 strain of *Pichia pastoris*. A tryptase expressing clone was isolated and used for large scale expression by fermentation in buffered minimal methanol complex media with 0.5 mg/ml heparin. Secreted mature βI and βII tryptases were purified to homogeneity using a two-column affinity chromatography procedure described previously. The enzymes were suspended in a final storage buffer containing 2M NaCl and 10 mM MES, pH 6.1 and 10% glycerol.

The proportion of catalytically active βI and βII tryptase was quantitated by active-site titration with MUGB (Jameson et al., *Biochemical Journal* 131(1): 107–17 (1973)). Briefly, fluorescence was monitored, with excitation at 360 nm and emission at 450 nm, upon addition of enzyme to MUGB. The concentration of enzyme was determined from the increase in fluorescence based on a standard concentration curve.

The recombinant human βI and βII tryptases (1 μg) and native human lung tryptase were subjected to reducing SDS/PAGE on a 4–20% TG gel (Novex). Following electrophoresis, the gel was stained by GelCode™ (Pierce, Rockford, Ill.) (FIG. 4) to verify size and purity.

7.3 Results

Recombinant tryptase βI and βII were produced and secreted in *Pichia pastoris* as mature enzymes. The ability to produce active mature enzyme rather than the zymogen is important for substrate specificity studies because it obviates the need to remove the pro-peptide through the addition of an activating protease, whose activity may complicate subsequent specificity studies. There is a single amino acid difference between tryptase βI and tryptase βII at position 113, an asparagine and a lysine respectively. Replacement of asparagine for lysine removes an N-linked glycosylation site in tryptase βII, making it singly glycosylated. The relative degree of glycosylation can be seen in the recombinant expression of both enzymes (FIG. 4) with tryptase βI migrating as mutiple glycosylated bands and tryptase βII migrating as a single glycosylated band. The only difference seen in expression and purification of the two enzymes is the final yield of active enzyme with tryptase βI expressing ten-fold more than tryptase βII. The phenomenon of reduced expression upon removal of a glycosylation site has been observed with other proteases and has been postulated to involve decreased stability or solubility of the enzyme lacking post-translational glycosylation (Harris et al., *Journal of Biological Chemistry* 273(42): 27364–73 (1998)).

Example 8

8.1 Positional Scanning Synthetic Combinatorial Library Screening

Preparation and screening of the positional scanning synthetic combinatorial library (PS—SCL) was carried out as previously described (Harris et al., *Proceedings of the National Academy of Sciences* 97(14): 7754–7759 (2000); Backes et al., *Nature Biotechnology* 18(2): 187–193 (2000)). The concentration of each of the 361 substrates per well in the P1-Lysine and P1-Arginine libraries was 0.25 μM. The concentration of the 6859 compounds per well in the P1-Diverse library was 0.013 μM. Enzyme activity of the PS—SCL was assayed in 100 mM HEPES pH 7.5, 10% glycerol and 0 or 0.1 mg/ml heparin at excitation and emission wavelengths of 380 nm and 450 nm respectively.

8.2 Results

To explore whether this single difference in glycosylation affects the substrate specificity of tryptase βI and βII, three combinatorial peptide libraries with fluorogenic leaving groups were used. The P1-specificity was first defined using a library in which each of the P1-amino acids in a tetrapeptide was held constant while the other three positions contain an equimolar mixture of 19 amino acids (cysteine was omitted and norleucine replaced methionine). Both tryptase βI and βII prefer cleaving after lysine over arginine with no other amino acids being accepted at this position (FIG. 5).

Figure 6A:
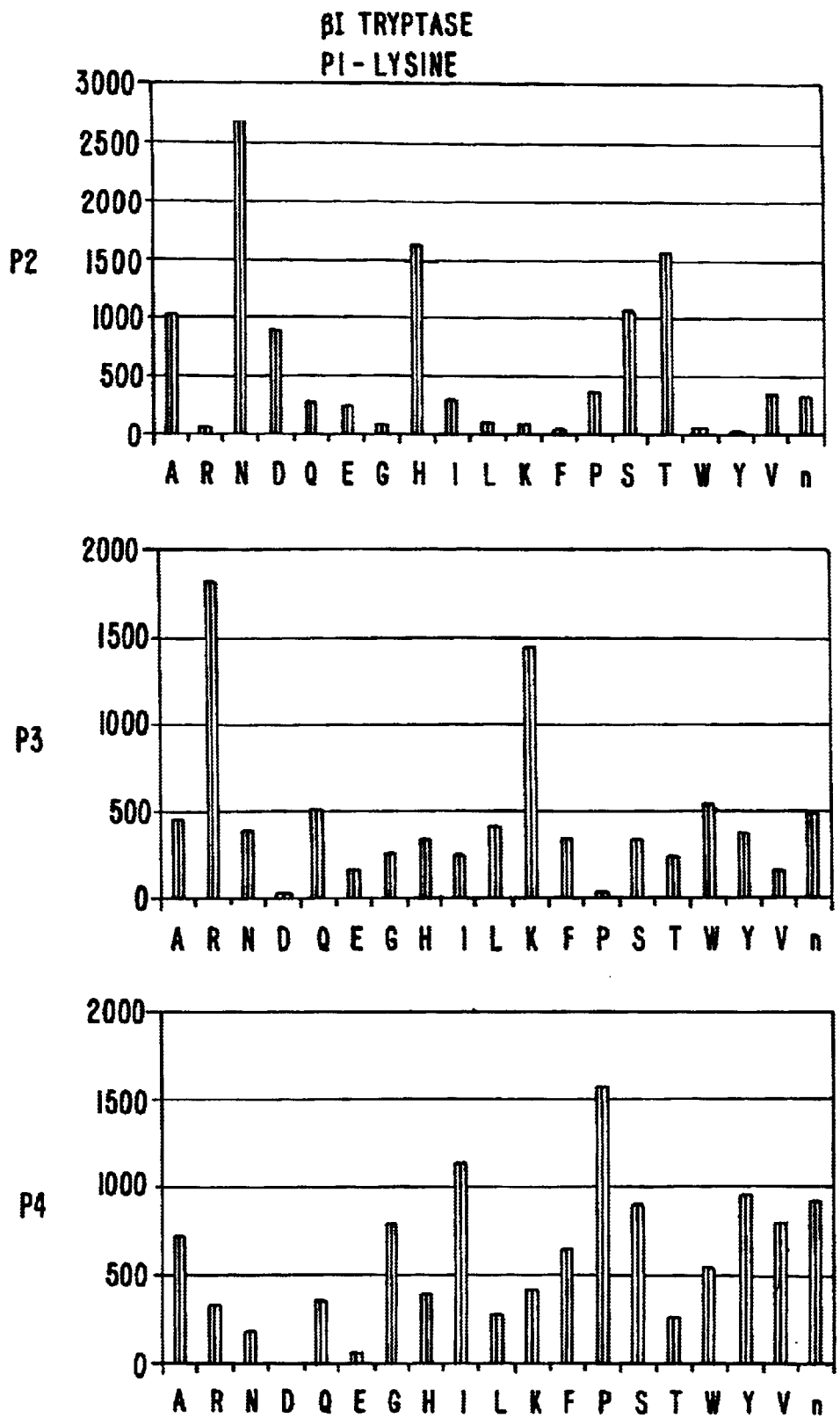
Figure 6B:
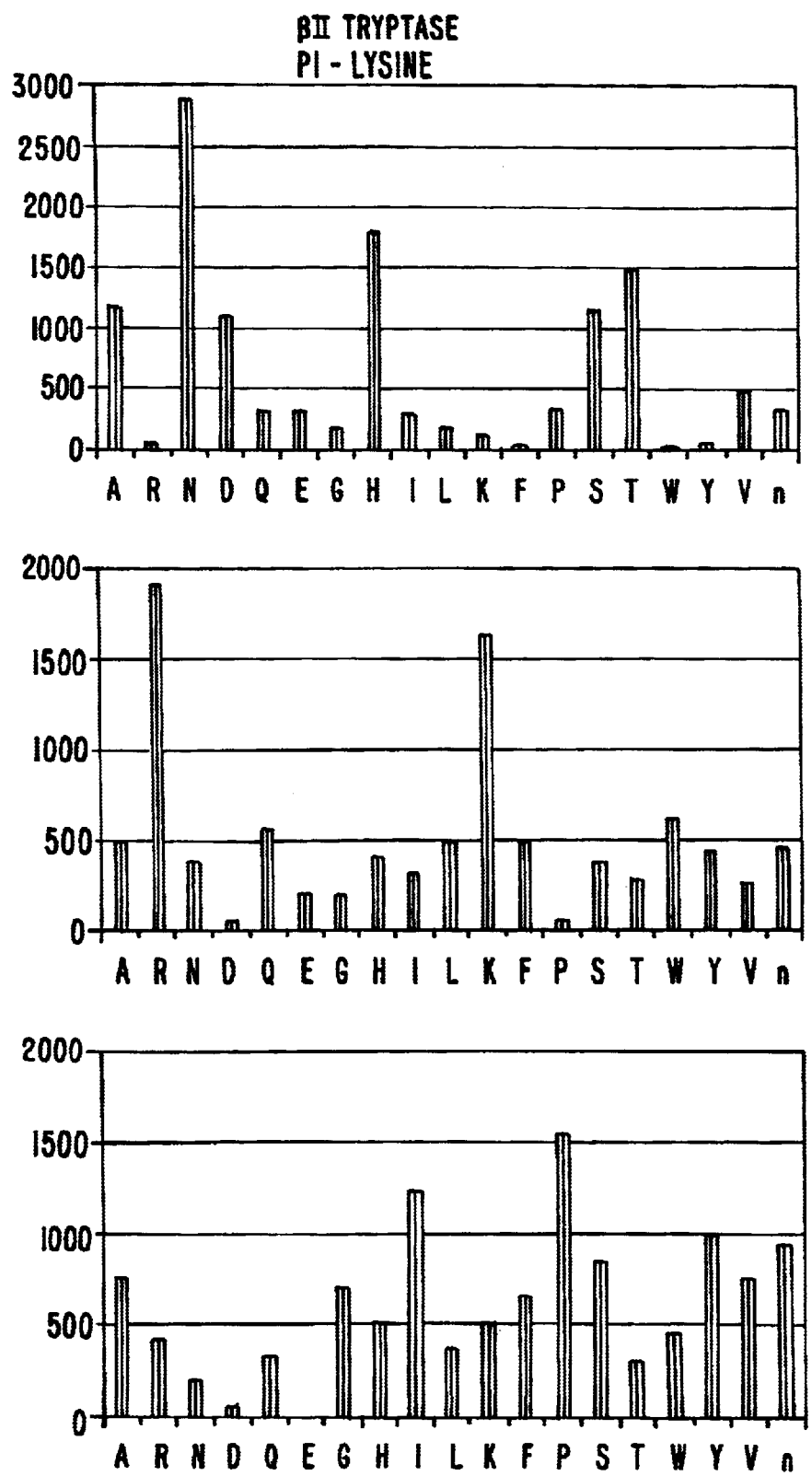
Figure 6C:
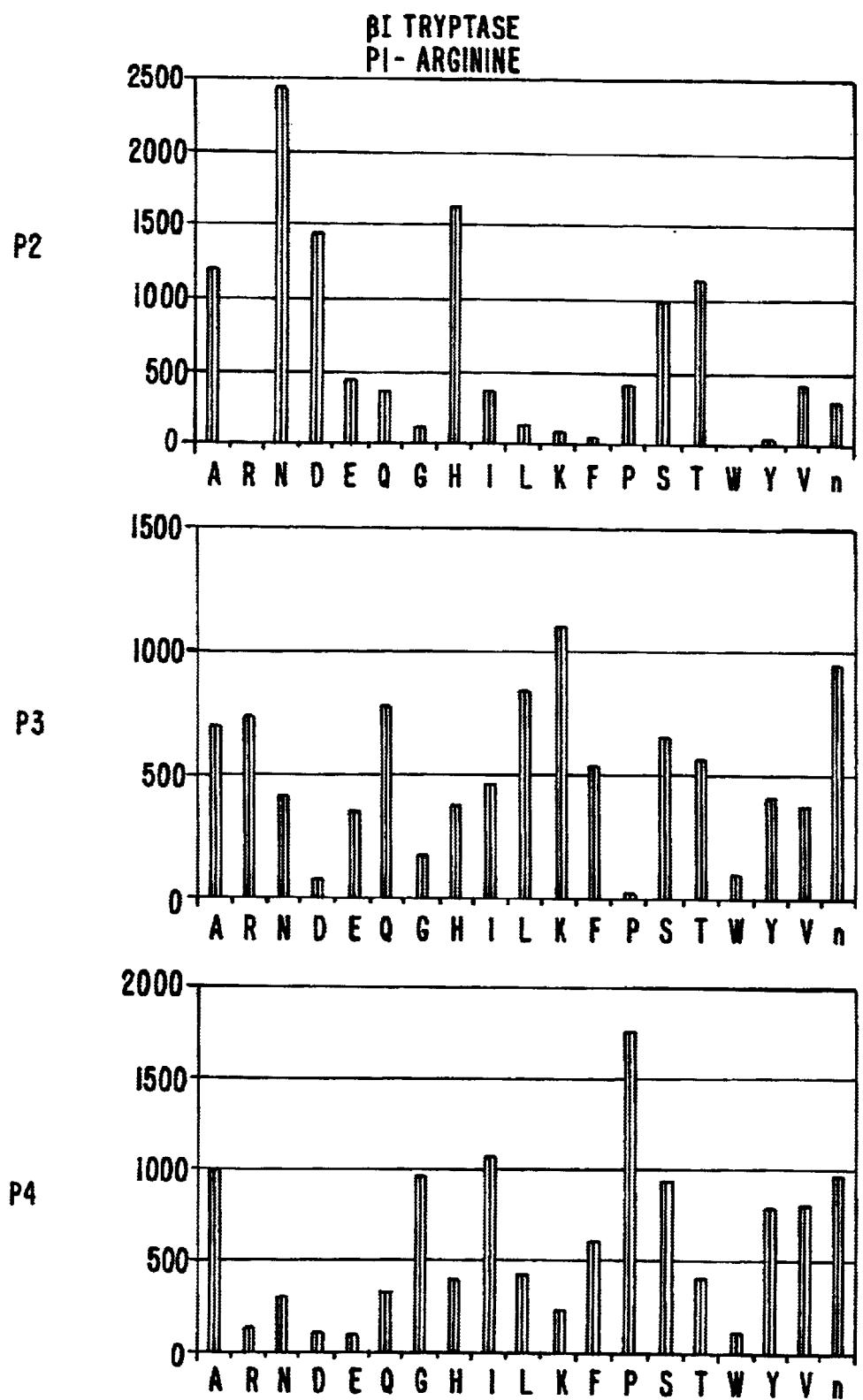
Figure 6D:
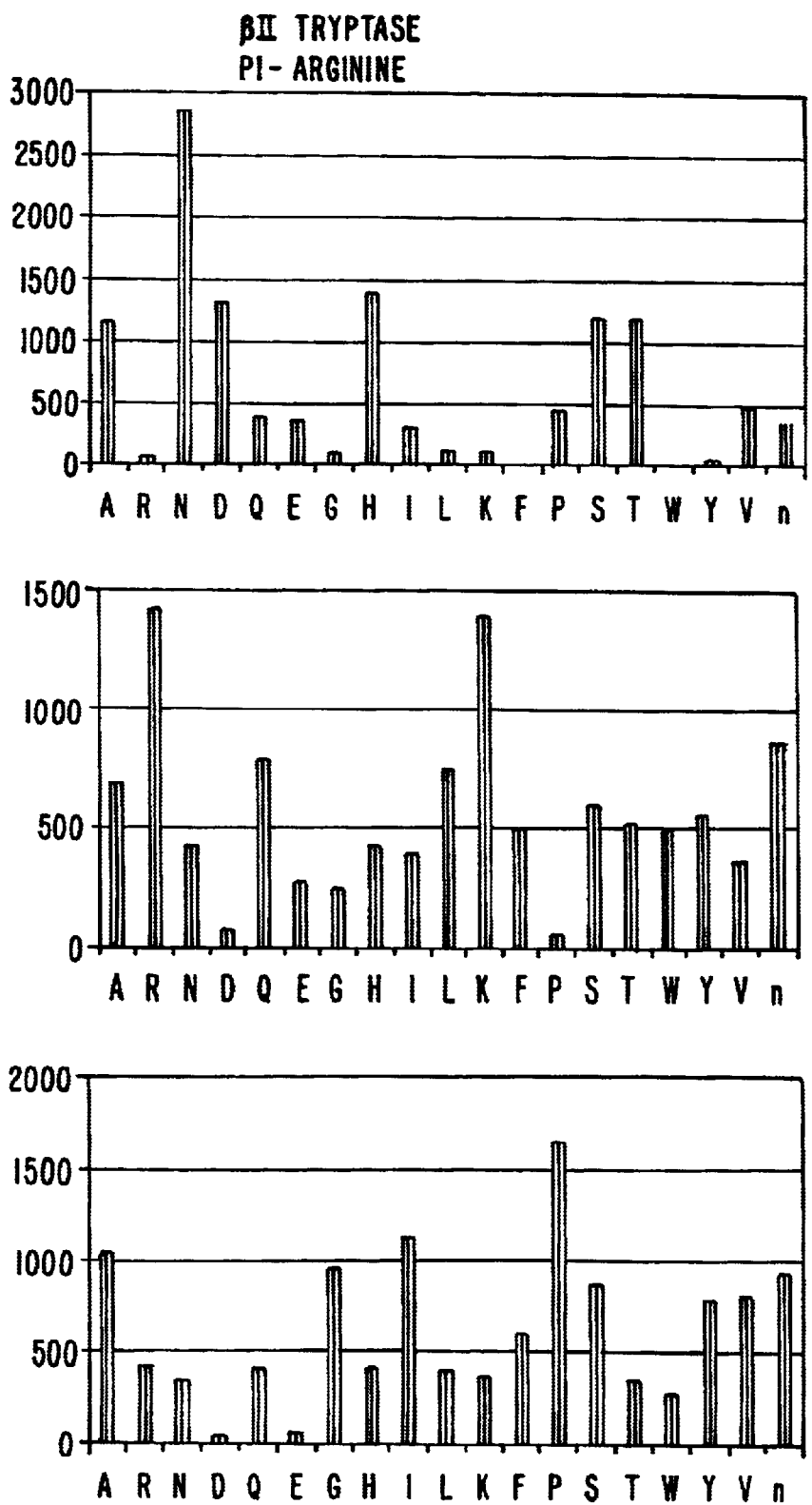

To define the extended substrate specificities of the β-tryptases as well as to determine if extended specificity is dependent on the context of the P1 amino acid, tryptase βI and βII were screened against two libraries that differed only in the P1 amino acid that was held constant, lysine and arginine. The P4 to P2 extended substrate specificities of both β-tryptases reveal that the isoforms have a similar substrate preference that is not dependent on the P1 amino acid (FIG. 6A and FIG. 6B). Also apparent from the specificity screen is that many sub-optimal amino acids can be accommodated in the substrate suggesting that additional mechanisms of substrate discrimination may also be in place. Both tryptases show an unusual preference for proline in the P4 position; no other serine protease has been shown to have preference to date. The P3 position shows a preference for positively charged amino acids. Finally, the P2-position shows a modest preference for asparagine (FIG. 6A and FIG. 6B).

Example 9

9.1 Single Substrate Kinetic Analysis

Tryptase activity was monitored at 30° C. in assay buffer containing 100 mM HEPES pH 7.5 and 10% glycerol. Substrate stock solutions were prepared in DMSO. The final concentration of substrate ranged from 0.005–2 mM. The concentration of DMSO in the assay was less than 5%. The tryptase concentration was 5 nM. Hydrolysis of ACC substrates was monitored fluorometrically with an excitation wavelength of 380 nm and emission wavelength of 450 nm on a Fluoromax-2 spectrofluorimeter (JY Horiba).

9.2 Irreversible inhibitor, Ac-PRNK-cmk, Kinetic Analysis

Progress curves were obtained for tryptase (1 nM) inactivation by multiple concentrations of Ac-PRNK-cmk (50 nM to 10 μM). Activity was monitored at 30° C. in activity buffer with 100 μM Ac-PRNK-ACC substrate. The rate constant for loss of enzyme activity, $k_{obs}$, was determined from a non-linear regression of the progress curve data. $k_{obs}$ varied linearly with inhibitor concentration. Therefore, $k_{ass}$, the rate constant for the inactivation of enzyme with inhibitor, was determined by linear regression analysis (Bieth, J. G. *Methods in Enzymology* 248: 59–84 (1995)). Several P1-basic-preferring proteases were monitored for inhibition by Ac-PRNK-cmk as follows: tryptase bI (50 nM), tryptase bII (50 nM), factor Xa (50 nM), tPA (50 nM), uPA (50 nM), thrombin (1 nM), and plasmin (5 nM) were incubated for 5 minutes with 0 μM, 10 μM, 100 μM Ac-PRNK-cmk. After incubation, residual activity was monitored as follows: Ac-PRNK-ACC was added to a final concentration of 5 μM to the samples containing tryptase βI and βII; Ac-GTAR-ACC (5 μM) was added to the factor Xa and tPA samples; Ac-QFAR-ACC (5 μM) was added to the uPA samples; Ac-nTPR-ACC (5 μM) was added to the thrombin samples; and Ac-KQWK-ACC (5 μM) was added to plasmin samples.

9.3 Results

To quantitate tryptase βI and βII dependence on extended substrate specificity, several peptide substrates were synthesized and the kinetic constants determined for each of the enzymes. The slight preference for lysine over arginine as seen in the P1-Diverse peptide library (FIG. 4) was validated with the substrates Ac-PRNK-ACC and Ac-PRNR-ACC. The Ac-PRNR-ACC substrate displays about 70–90% of the activity of Ac-PRNK-ACC substrate; compare $k_{cat}/K_m$ of $(1.12\pm0.14)\times10^6$ $M^{-1}s^{-1}$ to $(1.23\pm0.15)\times10^6$ $M^{-1}s^{-1}$ for tryptase βI and $(1.31\pm0.19)\times10^6$ $M^{-1}s^{-1}$ to $(1.89\pm0.17)\times10^6$ $M^{-1}s^{-1}$ for tryptase βII (Table III). A minimal preference, approximately two-fold, for P2-asparagine over P2-threonine was seen for both enzymes when Ac-PRNK-ACC is compared to Ac-PRTK-ACC, $k_{cat}/K_m$ of $(0.78\pm0.07)\times10^6$ $M^{-1}s^{-1}$ to $(1.23\pm0.15)\times10^6$ $M^{-1}s^{-1}$ for tryptase βI and $(1.27\pm0.12)\times10^6$ $M^{-1}s^{-1}$ to $(1.89\pm0.17)\times10^6$ $M^{-1}s^{-1}$ for tryptase βII. A major difference is seen in the P3-position with an approximately ten-fold preference for Ac-PRNK-ACC over Ac-PANK-ACC, compare $k_{cat}/K_m$ of $(1.23\pm0.15)$ $10^6$ $M^{-1}S^{-1}$ to $(0.14\pm0.01)\times10^6$ $M^{-1}s^{-1}$ for tryptase βI and $(1.89\pm0.17)\times10^6$ $M^{-1}S^{-1}$ to $(0.18\pm0.01)\times10^6$ $M^{-1}s^{-1}$ for tryptase βII. All of these effects are manifested in the $K_m$ term, not the $k_{cat}$ term. This indicates that ground state binding and recognition are important factors in tryptase catalysis. These results are consistent with previous finding of Tanaka et al who showed that Z-Lys-Gly-Arg-pNA was the most optimal of the fourteen tripepidyl para-nitroanalide substrates tested (Tanaka et al., *Journal of Biological Chemistry* 258(22): 13552–13557 (1983)).

TABLE III

| Substrate | $k_{cat}$ (s$^{-1}$) | $K_m$ (μM) | $k_{cat}/K_m$ (s$^{-1}$ M$^{-1}$) |
|---|---|---|---|
| βI Tryptase | | | |
| Ac-PRNK-AAC | 16.84 ± 0.27 | 8.9 ± 0.9 | (1.89 ± 0.17) × 10$^6$ |
| Ac-PANK-AAC | 20.27 ± 0.48 | 110.5 ± 9.8 | (0.18 ± 0.01) × 10$^6$ |
| Ac-PRTK-AAC | 18.67 ± 0.30 | 14.7 ± 1.4 | (1.27 ± 0.12) × 10$^6$ |
| Ac-PRNR-AAC | 21.75 ± 0.67 | 16.5 ± 2.7 | (1.31 ± 0.19) × 10$^6$ |
| βII Tryptase | | | |
| Ac-PRNK-AAC | 17.84 ± 0.40 | 14.5 ± 1.9 | (1.23 ± 0.15) × 10$^6$ |
| Ac-PANK-AAC | 19.06 ± 0.64 | 133.3 ± 15.6 | (0.14 ± 0.01) × 10$^6$ |
| Ac-PRTK-AAC | 18.34 ± 0.33 | 23.4 ± 2.3 | (0.78 ± 0.07) × 10$^6$ |
| Ac-PRNR-AAC | 20.94 ± 0.57 | 18.6 ± 2.6 | (1.12 ± 0.14) × 10$^6$ |

Example 10
10.1 Irreversible Inhibitor, Ac-PRNK-cmk, Kinetic Analysis

Progress curves were obtained for tryptase (1 nM) inactivation by multiple concentrations of Ac-PRNK-cmk (50 nM to 10 μM). Activity was monitored at 30° C. in activity buffer with 100 μM Ac-PRNK-ACC substrate. The rate constant for loss of enzyme activity, $k_{obs}$, was determined from a non-linear regression of the progress curve data. $k_{obs}$ varied linearly with inhibitor concentration. Therefore, $k_{ass}$, the rate constant for the inactivation of enzyme with inhibitor, was determined by linear regression analysis (Bieth (1995)). Several P1-basic-preferring proteases were monitored for inhibition by Ac-PRNK-cmk as follows: tryptase bI (50 nM), tryptase bII (50 nM), factor Xa (50 nM), tPA (50 nM), uPA (50 nM), thrombin (1 nM), and plasmin (5 nM) were incubated for 5 minutes with 0 μM, 10 μM, 100 μM Ac-PRNK-cmk. After incubation, residual activity was monitored as follows: Ac-PRNK-ACC was added to a final concentration of 5 μM to the samples containing tryptase βI and βII; Ac-GTAR-ACC (5 μM) was added to the factor Xa and tPA samples; Ac-QFAR-ACC (5 μM) was added to the uPA samples; Ac-nTPR-ACC (5 μM) was added to the thrombin samples; and Ac-KQWK-ACC (5 μM) was added to plasmin samples.
10.2 Results To demonstrate that information obtained from the substrate screen could be translated into a potent tryptase inhibitor, the irreversible inhibitor Ac-PRNK-cmk was tested for inhibition of tryptase. The measured association rate constant, $k_{ass}$, of 5000±200 M$^{-1}$ sec$^{-1}$ for both βI and βII tryptase indicates that Ac-PRNK-cmk is a potent inhibitor of tryptase. Selectivity of the designed tryptase inhibitor, Ac-PRNK-cmk, was demonstrated through the measurement of inhibition of several tryptic plasma proteases, factor Xa, tPA, uPA, thrombin, and plasmin. At an inhibitor concentration of 10 μM, where tryptase is 95% inhibited, none of the proteases tested showed inhibition (Table IV). At a 10-fold higher inhibitor concentration of inhibitor (100 μM), where tryptase is completely inhibited, only uPA and plasmin showed inhibition, 34% and 63% inhibition respectively (Table IV).

TABLE IV

| Enzyme | Percent Inhibition 100 μM Ac-PRNK-cmk | Percent Inhibition 10 μM Ac-PRNK-cmk |
|---|---|---|
| Tryptase βI | 100 | 95 |
| Tryptase βII | 100 | 95 |
| Factor Xa | 0 | 0 |
| tPA | 0 | 0 |
| uPA | 34 | 0 |
| Thrombin | 0 | 0 |
| Plasmin | 63 | 0 |

Example 11
11.1 Structural Modeling of Optimized Substrate into Tryptase Active Site The tryptase structure (PDB code 1a01) was prepared for modeling by removing inhibitor and water molecules, adding hydrogens using Sybyl6.5 (Tripos Inc. 1699 South Hanley Road, S. L., Missouri, 63144, USA.), and assigning AMBER partial atomic charges (Cornell et al., *Journal of the American Chemical Society* 117(19): 5179–5197 (1995)). Because the structure was solved with a covalent inhibitor, the catalytic Ser-195 was modeled to a geometry consistent with a non-covalent inhibitor by restoring the hydrogen bond with His-57. This was accomplished with a two-step torsional minimization in Sybyl (Tripos force field, ε=1r). In the first step the position of the Ser-195 hydroxyl hydrogen was minimized via torsion around the X2 bond, and in the second step both the oxygen and hydrogen were minimized via torsion around the $\chi_2$ bond and $\psi_1$ (CCCO) bonds. The structure of the enzyme was held rigid for the remainder of the modeling.

The capped peptide backbone of Ac-PRNK-Nme was modelled into the active site of the tryptase structure as follows. The structure of the P1-P3 portion of ovomucoid (complexed to chymotrypsin, PDB code 1 cho) was used as a template for the backbone configuration. This portion of the inhibitor was translated into the tryptase active site using least squares superposition of the protease active site residues His-57, Asp-102, Ser-195, and 214–216 onto the corresponding residues of the tryptase "A" protomer. The peptide sidechains were then truncated at C-β, hydrogens and AMBER charges were added (as above) and the configuration of the resultant (Ace-AAA-Nme) peptide was optimized with successive minimizations in the tryptase active site. Using DOCK4.0.1 (Ewing, T. J. A., Makino, S., Skillman, A. G., and Kuntz, I. D. (In Press), the atoms of the scissile amide bond were minimized first, then successive rigid segments of the peptide were added (with torsional angles taken from the ovomucoid inhibitor) alternating with minimization. The minimizations included rigid and flexible degrees of freedom and were performed using the simplex algorithm with up to 500 iterations for each minimization. The DOCK energy scoring, applied to both intermolecular and intramolecular atom pairs, includes the coulombic and van der Waals terms from the AMBER force field (Ewing, supra; Weiner et al., *Journal of Computational Chemistry* 7(2): 230–252 (1986)). An interatomic cutoff of 25 Å and ε=4r. The peptide side chains (PRNK) were then added, and the conformation of the P1-P3 side chains and the P4 proline were modelled with DOCK4.0. Finally, 10 independent minimizations were carried out, and the lowest-energy configuration was retained.

11.2 Results

The source of the preference for basic residues at the P1 position is well known for this class of proteolytic enzyme: Asp-189 is present in all trypsin-like serine proteases and resides at the bottom of the SI pocket. The source of extended specificity is less apparent. The structure of tryptase is unique among serine proteases in that it is a ring-like tetramer with the four active sites in close proximity within the interior pore (Pereira et al., *Nature* 392: 306–311 (1998)). Using the program DOCK with energy scoring (Meng et al., *Journal of Computational Chemistry* 13(4): 505–524 (1992)), the capped tripeptide Ac-PRNK-Nme was docked into the active site of BII tryptase. The docked molecule had a score of −86.34 DOCK units, consisting of an electrostatic contribution of −56.88 and a van der Waals contribution of −29.46. The unusually large electrostatic component is a result of the large negative charge concentrated within the pore of the tetramer.

The model of substrate binding reveals a paired binding site, with contributions from two tryptase protomers. Specifically, docking of the optimal peptide into the active site of tryptase predicts that the P4 and P3 side chains interact with the adjacent protomer. The P4-Pro side chain interacts with the γ-carbon of Thr-96' of the adjacent protomer (FIG. 7). A recognition site for the P3-Arg is formed by acidic residues from both protomers, Glu-217 from the cognate protomer and Asp-60B' from the adjacent protomer (FIG. 7). Formation of the P4 and P3 side chain interactions requires a somewhat non-canonical backbone configuration resulting in the loss of a backbone hydrogen bond. By contrast, the P2 and P1 sites make the canonical interactions seen with other members of this protease class. For example, the deep S1-pocket contains Asp-189 from the cognate protomer that interacts with P1-Lys (FIG. 7). Another consequence of the structure is that each active site has an adjacent active site in close proximity leading to potential substrate—substrate interactions (FIG. 7).

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A material having a fluorogenic moiety linked to a solid support, said material having the structure:

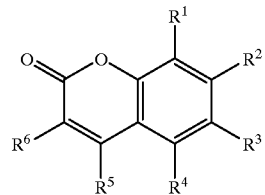

wherein:

$R^1$, $R^2$, $R^3$, $R^4$, $R^5$ and $R^6$ are members independently selected from the group consisting of H, halogen, —$NO_2$, —CN, —$C(O)_mR^7$, —$C(O)NR^8R^9$, —$S(O)_tR^{10}$, —$SO_2NR^{11}R^{12}$, —$OR^{13}$, substituted or unsubstituted alkyl, —$R^{14}$—SS, and —$NHR^{15}$ with the proviso that at least one of $R^1$, $R^2$, $R^3$, $R^4$, $R^5$ and $R^6$ is —$R^{14}$—SS and at least one of $R^1$, $R^2$, $R^3$, $R^4$, $R^5$ and $R^6$ is —$NHR^{15}$, wherein:

$R^7$, $R^8$, $R^9$, $R^{10}$, $R^{11}$, $R^{12}$, $R^{13}$, $R^{18}$ and $R^{19}$ are members independently selected from the group consisting of H, substituted or unsubstituted alkyl and substituted or unsubstituted aryl;

$R^{14}$ is a linking group adjoining said fluorogenic moiety and said solid support;

$R^{15}$ is a member selected from the group consisting of amine protecting groups, —C(O)-AA and —C(O)—P:

wherein:

P is a peptide sequence;

AA is an amino acid residue;

m is a member selected from the group consisting of the integers 1 and 2;

t is a member selected from the group consisting of the integers from 0 to 2; and SS is a solid support.

2. The material according to claim 1, wherein said linking group is a member selected from the group consisting of substituted or unsubstituted alkyl, substituted or unsubstituted heteroalkyl and substituted or unsubstituted aryl.

3. The material according to claim 1, wherein P is a peptide sequence comprising the structure:

wherein, $AA^1$-$AA^2$-$(AA^i)_{J-2}$ is a peptide sequence, wherein each of $AA^1$ through $AA^i$ is an amino acid residue which is a member independently selected from the group of natural amino acid residues, unnatural amino acid residues and modified amino acid residues;

J denotes the number of amino acid residues forming said peptide sequence and is a member selected from the group consisting of the numbers from 2 to 10, such that J-2 is the number of amino acid residues in the peptide sequence exclusive of $AA^1$-$AA^2$; and i denotes the position of said amino acid residue relevant to $AA^1$ and when J is greater than 2, i is a member selected from the group consisting of the numbers from 3 to 10.

4. The material according to claim 1, wherein $R^{15}$ has the structure:

—C(O)-AA; and

AA is an amino acid residue selected from the group consisting of natural amino acids, unnatural amino acids and modified amino acids.

5. The material according to claim 1, having the structure:

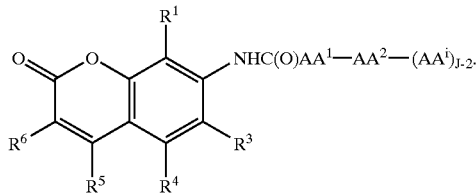

6. The material according to claim 5, having the structure:

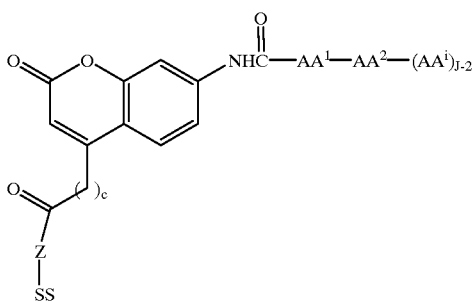

wherein, Z is a member selected from the group consisting of —O—, and —NR$^{16}$—; and c is a member selected from the integers from 0 to 6.

7. A material according to claim 6, having the structure:

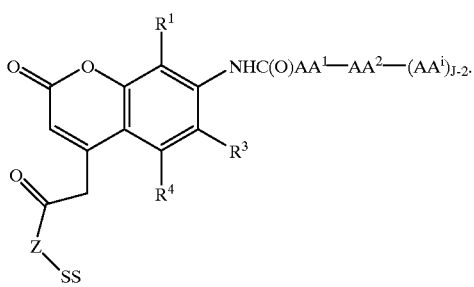

8. A method of assaying for the presence of an enzymatically active protease in a sample, said method comprising:
  (a) contacting said sample with a material according to claim 3 in such a manner whereby said fluorogenic moiety is released from said peptide sequence upon action of said protease, thereby producing a fluorescent moiety; and
  (b) observing whether said sample undergoes a detectable change in fluorescence, said detectable change being an indication of the presence of said enzymatically active protease in said sample.

9. The method according to claim 8, wherein said protease is a member selected from the group consisting of aspartic protease, cysteine protease, metalloprotease and serine protease.

10. The method according to claim 8, wherein said protease is a protease of a microorganism.

11. The method according to claim 10, wherein said microorganism is a member selected from the group consisting of bacteria, fungi, yeast, viruses, and protozoa.

12. The method according to claim 8, wherein said sample is a clinical sample from a subject.

13. The method according to claim 8, further comprising (c) quantifying said fluorescent moiety, thereby quantifying said protease.

14. A method of assaying for the presence of a selected microorganism in a sample by probing the sequence specificity of peptide cleavage by a protease of said microorganism, said method comprising:
  (a) contacting a sample suspected of containing said selected microorganism with a material according to claim 3, wherein said peptide comprises a sequence that is selectively cleaved by said protease of said selected microorganism, thereby releasing the fluorogenic moiety from the peptide sequence;
  (b) detecting the cleavage by detecting fluorescence arising from a fluorescent moiety produced by cleavage of said fluorogenic moiety from said peptide sequence, thereby confirming said presence of said selected microorganism in said sample.

15. The method according to claim 14, further comprising (c) quantifying said fluorescence, thereby quantifying said protease of said microorganism.

16. A fluorogenic peptide comprising a fluorogenic moiety covalently bound to a peptide sequence, said peptide having the structure:

R—P wherein:
  P is a peptide sequence having the structure:

—C(O)-AA$^1$-AA$^2$-(AA$^i$)$_{J-2}$ wherein:
  each of AA$^1$ through AA$^i$ is an amino acid residue which is a member independently selected from the group of natural amino acid residues, unnatural amino acid residues and modified amino acid residues;
  J denotes the number of amino acid residues forming said peptide sequence and is a member selected from the group consisting of the numbers from 2 to 10, such that J-2 is the number of amino acid residues in the peptide sequence exclusive of AA$^1$-AA$^2$;
  i denotes the position of said amino acid residue in sequence relative to AA$^1$ and when J is greater than 2, i is a member selected from the group consisting of the numbers from 3 to 10; and
  R is a fluorogenic moiety having the structure:

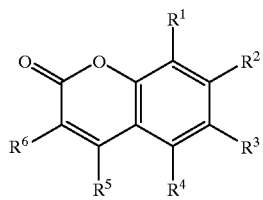

wherein:
  $R^1$, $R^2$, $R^3$, $R^4$, $R^5$ and $R^6$ are members independently selected from the group consisting of H, halogen, —$NO_2$, —CN, —$C(O)_mR^7$, —$C(O)NR^8R^9$, —$S(O)_tR^{10}$, —$SO_2NR^{11}R^{12}$, —$OR^{13}$, $NR^{18}R^{19}$, substituted or unsubstituted alkyl, —$R^{14}$—SS, and —$NHR^{15}$ with the proviso that at least one of $R^1$, $R^2$, $R^3$, $R^4$, $R^5$ and $R^6$ is —$R^{14}$—SS and at least one of $R^1$, $R^2$, $R^3$, $R^4$, $R^5$ and $R^6$ is —$NHR^{15}$, wherein:

$R^7$, $R^8$, $R^9$, $R^{10}$, $R^{11}$, $R^{12}$, $R^{13}$, $R^{18}$ and $R^{19}$ are members independently selected from the group consisting of H, substituted or unsubstituted alkyl and substituted or unsubstituted aryl;

$R^{20}$ is either present or absent and is a member selected from the group consisting of substituted or unsubstituted alkyl and substituted or unsubstituted heteroalkyl;

Y is an organic functional group;

m is a member selected from the group consisting of the integers 1 and 2; and t is a member selected from the group consisting of the integers from 0 to 2.

17. The fluorogenic peptide according to claim 16, wherein said organic functional group is a member selected from the group consisting of —$COOR^{17}$, $CONR^{17}R^{21}$, —$C(O)R^{17}R^{21}$, —$OR^{17}$, —$SR^{17}$, —$C(O)SR^{17}$ and —$NR^{17}R^{21}$ wherein, $R^{17}$ and $R^{21}$ are members independently selected from H, substituted or unsubstituted alkyl and substituted or unsubstituted aryl.

18. The fluorogenic peptide according to claim 16, having the structure:

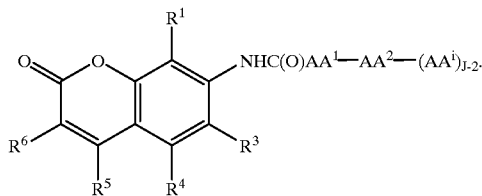

19. The fluorogenic peptide according to claim 18, having the structure:

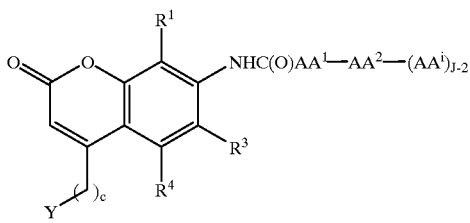

wherein:

c is a member selected from the group consisting of the integers from 0 to 6.

20. The fluorogenic peptide according to claim 19, having the structure:

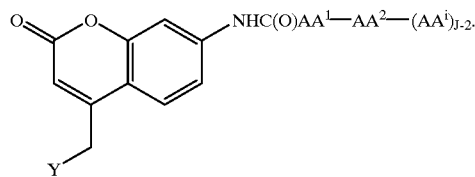

21. The fluorogenic peptide according to claim 16, wherein said peptide sequence comprises a peptide bond that is cleaved by a protease releasing said fluorogenic moiety from said peptide sequence, thereby producing a fluorescent moiety and a peptide moiety.

22. The fluorogenic peptide according to claim 21, wherein said peptide bond is formed between a carboxyl of the carboxy-terminus amino acid residue and an amine group of said fluorogenic moiety.

23. A method of assaying for the presence of an enzymatically active protease in a sample, said method comprising:

(a) contacting a sample suspected of containing said protease with a peptide according to claim 16 in such a manner whereby said fluorogenic moiety is released from said peptide sequence upon action of said protease, thereby producing a fluorescent moiety; and (b) observing whether said sample undergoes a detectable change in fluorescence, said detectable change being an indication of the presence of said enzymatically active protease in said sample.

24. The method according to claim 23, wherein said protease is a member selected from the group consisting of aspartic protease, cysteine protease, metalloprotease and serine protease.

25. The method according to claim 23, wherein said protease is a protease of a microorganism.

26. The method according to claim 25, wherein said microorganism is a member selected from the group consisting of bacteria, fungi, yeast, viruses, and protozoa.

27. The method according to claim 23, wherein said sample is a clinical sample from a subject.

28. The method according to claim 27, wherein said subject is a human.

29. The method according to claim 23, further comprising (c) quantifying said fluorescent moiety, thereby quantifying said protease.

30. A method of assaying for the presence of a selected microorganism in a sample by probing the sequence specificity of peptide cleavage by a protease of said microorganism, said method comprising:

(a) contacting a sample suspected of containing said selected microorganism with a material according to claim 16, wherein said peptide comprises a sequence that is selectively cleaved by a protease of a selected microorganism, thereby releasing said fluorogenic moiety from said peptide sequence;

(b) detecting said cleavage by detecting fluorescence arising from a fluorescent moiety produced by cleavage of said fluorogenic moiety from said peptide sequence, thereby confirming said presence of said selected microorganism in said sample.

31. The method according to claim 30, further comprising (c) quantifying said fluorescence, thereby quantifying said protease of said microorganism.

32. A library of fluorogenic peptides comprising at least a first peptide having a first peptide sequence covalently attached to a first fluorogenic moiety and a second peptide having a second peptide sequence covalently attached to a second fluorogenic moiety, said first peptide and said second peptide having the structure:

R—P wherein:
for each of said first peptide and said second peptide, P is independently selected from peptide sequences having the structure:

—C(O)-AA$^1$-AA$^2$-(AA$^i$)$_{J-2}$ wherein:
each of AA$^1$ through AA$^i$ is an amino acid residue which is a member independently selected from the group consisting of natural amino acid residues, unnatural amino acid residues and modified amino acid residues;
each J is independently selected and denotes the number of amino acid residues forming said first peptide sequence and said second peptide sequence and is a member selected from the group consisting of the numbers from 2 to 10;
each i is independently selected and denotes the position of said amino acid residue relative to AA$^1$ and when J is greater than 2, i is a member selected from the group consisting of the numbers from 3 to 10; and
for each of said first peptide and said second peptide R is independently selected from fluorogenic moieties having the structure:

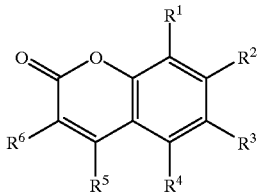

wherein:
R$^1$, R$^2$, R$^3$, R$^4$, R$^5$ and R$^6$ are members independently selected from the group consisting of H, halogen, —NO$_2$, —CN, —C(O)$_m$R$^7$, —C(O)NR$^8$R$^9$, —S(O)$_t$R$^{10}$, —SO$_2$NR$^{11}$R$^{12}$, —OR$^{13}$, NR$^{18}$R$^{19}$, substituted or unsubstituted alkyl, —R$^{14}$—SS, and —NHR$^{15}$
with the proviso that at least one of R$^1$, R$^2$, R$^3$, R$^4$, R$^5$ and R$^6$ is R$^{14}$—SS and at least one of R$^1$, R$^2$, R$^3$, R$^4$, R$^5$ and R$^6$ is —NHR$^{15}$,
wherein:
R$^7$, R$^8$, R$^9$, R$^{10}$, R$^{11}$, R$^{12}$, R$^{13}$, R$^{18}$ and R$^{19}$ are members independently selected from the group consisting of H, substituted or unsubstituted alkyl and substituted or unsubstituted aryl;
R$^{14}$ is a linking group adjoining said fluorogenic moiety and the solid support;
R$^{20}$ is either present or absent and is a member selected from the group consisting of substituted or unsubstituted alkyl and substituted or unsubstituted heteroalkyl;
Y is a member selected from the group consisting of organic functional groups and methyl;
m is a member selected from the group consisting of the integers from 1 to 2;

t is a member selected from the group consisting of the integers from 0 to 2;
R$^{17}$ is a member selected from the group consisting of H, substituted or unsubstituted alkyl and substituted or unsubstituted aryl; and
SS is a solid support.

33. The library according to claim 32, wherein said linking group is a member selected from the group consisting of substituted or unsubstituted alkyl and substituted or unsubstituted heteroalkyl.

34. The library according to claim 32, wherein said organic functional group is a member selected from the group consisting of —COOR$^{17}$, CONR$^{17}$R$^{21}$, —C(O)R$^{17}$R$^{21}$, —OR$^{17}$, —SR$^{17}$, —C(O)SR$^{17}$, and —NR$^{17}$R$^{21}$
wherein, R$^{17}$ and R$^{21}$ are members independently selected from H, substituted or unsubstituted alkyl and substituted or unsubstituted aryl.

35. The library of fluorogenic peptides according to claim 32, wherein R—P has the structure:

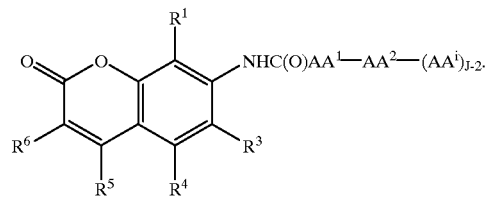

36. The library of fluorogenic peptides according to claim 35, wherein R—P has the structure:

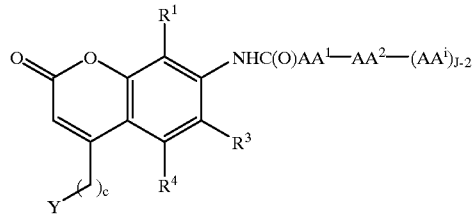

wherein,
c is a member selected from the group consisting of the numbers from 0 to 6.

37. The library of fluorogenic peptides according to claim 36, wherein R—P has the structure:

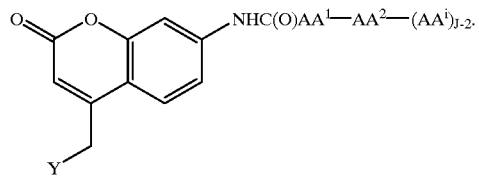

38. The library according to claim 32, wherein said fluorogenic moiety of said first peptide and said fluorogenic moiety of said second peptide are different fluorogenic moieties.

39. The library according to claim 32, wherein said first peptide sequence and said second peptide sequence are identical.

40. The library according to claim 32, wherein said first peptide sequence and said second peptide sequence are different.

41. The library according to claim 40, wherein an amino acid residue selected from the group consisting of $AA^1$, $AA^2$, $AA^i$ and combinations thereof of said first peptide is a different amino acid residue than an amino acid residue at a corresponding position relative to $AA^1$ of said second peptide.

42. The library according to claim 32, wherein $AA^1$ of said first peptide sequence and $AA^1$ of said second peptide sequence are identical amino acid residues.

43. The library according to claim 32, wherein $AA^1$ of said first peptide sequence and $AA^1$ of said second peptide sequence are different amino acid residues.

44. The library according to claim 32, wherein $AA^2$ of said first peptide sequence and $AA^2$ of said second peptide sequence are identical amino acid residues.

45. The library according to claim 32, wherein $AA^2$ of said first peptide sequence and $AA^2$ of said second peptide sequence are different amino acid residues.

46. The library according to claim 32, wherein $AA^i$ of said first peptide sequence and $AA^i$ of said second peptide sequence are identical amino acid residues.

47. The library according to claim 32, wherein $AA^i$ of said first peptide sequence and $AA^i$ of said second peptide sequence are different amino acid residues.

48. The library according to claim 42, comprising at least six peptides having different peptide sequences, wherein $AA^1$ is a different amino acid residue in each of said different peptide sequences.

49. The library according to claim 48, comprising at least twelve peptides having different peptide sequences wherein $AA^1$ is a different amino acid residue in each of said different peptide sequences.

50. The library according to claim 49, comprising at least twenty peptides having different peptide sequences wherein $AA^1$ is a different amino acid residue in each of said different peptide sequences.

51. The library according to claim 32, wherein $AA^1$ is a member selected from the group consisting of Lys, Arg, Leu and combinations thereof.

52. The library according to claim 32, wherein J is a member selected from the numbers from 4 to 8.

53. The library of peptides according to claim 32, wherein at least one of said first peptide and said second peptide is cleavable by a protease into a fluorescent moiety and the peptide sequence.

54. The library according to claim 32, comprising at least 10 peptides, wherein each of the peptide sequences is a different peptide sequence.

55. The library according to claim 54, comprising at least 100 peptides, wherein each of the peptide sequences is a different peptide sequence.

56. The library according to claim 55, comprising at least 1,000 peptides, wherein each of the peptide sequences is a different peptide sequence.

57. The library according to claim 56, comprising at least 10,000 peptides, wherein each of the peptide sequences is a different peptide sequence.

58. The library according to claim 57, comprising at least 100,000 peptides, wherein each of the peptide sequences is a different peptide sequence.

59. The library according to claim 58 comprising at least 1,000,000 peptides, wherein each of the peptide sequences is a different peptide sequence.

60. The library according to claim 32, wherein said first peptide is located at a first region of a substrate and said second peptide is located at a second region of a substrate.

61. A method of determining a peptide sequence specificity profile of an enzymatically active protease, said method comprising:

(a) contacting said protease with a library of peptides according to claim 32 in such a manner whereby the fluorogenic moiety is released from the peptide sequence, thereby forming a fluorescent moiety;
(b) detecting said fluorescent moiety;
(c) determining the sequence of said peptide sequence, thereby determining said peptide sequence specificity profile of said protease.

62. The method according to claim 61, further comprising (d) quantifying said fluorescent moiety, thereby quantifying said protease.

63. A database comprising at least one set of peptide sequence specificity data for a protease determined using a library according to claim 32.

64. The database according to claim 63, wherein said database is an electronic database.

65. The database according to claim 64, wherein said database is distributed on a wide area network.

66. A database comprising at least one set of peptide sequence specificity data for a protease determined using a method according to claim 61.

67. The database according to claim 63, wherein said database is an electronic database.

68. The database according to claim 64, wherein said database is distributed on a wide area network.

69. The method according to claim 61, wherein said protease is a member selected from the group consisting of aspartic protease, cysteine protease, and serine protease.

70. The method according to claim 61, wherein said protease is a protease of a microorganism.

71. The method according to claim 70, wherein said microorganism is a member selected from the group consisting of bacteria, fungi, yeast, viruses, and protozoa.

72. The method according to claim 61, further comprising (d) quantifying the fluorescent moiety, thereby quantifying said protease.

73. A method of preparing a fluorogenic peptide, said method comprising:

(a) providing a first conjugate comprising a fluorogenic moiety covalently bonded to a solid support, said conjugate having the structure:

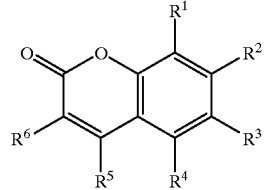

wherein,
$R^1$, $R^2$, $R^3$, $R^4$, $R^5$ and $R^6$ are members independently selected from the group consisting of H, halogen, $-NO_2$, $-CN$, $-C(O)_m R^7$, $-C(O)NR^8 R^9$, $-S(O)_t R^{10}$, $-SO_2 NR^{11} R^{12}$, $-OR^{13}$, $-NR^{18} R^{19}$, and substituted or unsubstituted alkyl, with the proviso that at least one of $R^1$, $R^2$, $R^3$, $R^4$, $R^5$ and $R^6$ is $-NH_2$; $R^7$, $R^8$, $R^9$, $R^{10}$, $R^{11}$, $R^{12}$, $R^{13}$, $R^{18}$ and $R^{19}$ are members independently selected from the group consisting of H, substituted or unsubstituted alkyl and substituted or unsubstituted aryl;
m is a member selected from the group consisting of the numbers from 1 to 2;
t is a member selected from the group consisting of the numbers from 0 to 2;
$R^5$ and $R^6$ are members independently selected from the group consisting of H and $-R^{14}-C(O)NH-SS$, wherein at least one of $R^5$ and $R^6$ is $-R^{14}-C(O)NH-SS$;

R[14] is a member selected from the group consisting of substituted or unsubstituted alkyl and substituted or unsubstituted heteroalkyl;

SS is a solid support;

(b) contacting said first conjugate with a first protected amino acid moiety (pAA[1]) and an activating agent, thereby forming a peptide bond between a carboxyl group of pAA[1] and the aniline nitrogen of said first conjugate;

(c) deprotecting said pAA[1], thereby forming a second conjugate having a reactive AA[1] amine moiety;

(d) contacting said second conjugate with a second protected amino acid (pAA[2]) and an activating agent, thereby forming a peptide bond between a carboxyl group of pAA2 and said reactive AA[1] amine moiety; and (e) deprotecting said pAA[2], thereby forming a third conjugate having a reactive AA[2] amine moiety.

74. The method according to claim 73, further comprising:

(f) contacting said third conjugate with a third protected amino acid (pAA[3]) and an activating agent, thereby forming a peptide bond between a carboxyl group of pAA[3] and said reactive AA[2] amine moiety; and (e) deprotecting said pAA[3], thereby forming a fourth conjugate having a reactive AA[3] amine moiety.

75. The method according to claim 73, further comprising between steps (b) and (c) capping aniline amine groups that have not reacted with pAA[1].

76. The method according to claim 75, wherein said capping utilizes a mixture comprising an active ester of a carboxylic acid.

77. The method according to claim 76, wherein said active ester is the nitrotriazole ester of acetic acid.

78. The method according to claim 74, wherein a member selected from the group consisting of pAA[1], pAA[2], pAA[3] and combinations thereof comprises a mixture of protected amino acids differing in the identity of the amino acid portion of the protected amino acids.

79. The method according to claim 78, wherein said mixture comprises at least 2 unique amino acids.

80. The method according to claim 79, wherein said mixture comprises at least 6 unique amino acids.

81. The method according to claim 80, wherein said mixture comprises at least 12 unique amino acids.

82. The method according to claim 81, wherein said mixture comprises at least 20 unique amino acids.

83. The method according to claim 78, wherein said mixture is an isokinetic mixture.

84. A fluorogenic peptide comprising a fluorogenic moiety covalently bound to a peptide sequence, said peptide having the structure:

R—P wherein:

P is a peptide sequence having the structure:

—C(O)-AA[1]-AA[2]-(AA[i])$_{J-2}$ wherein:

each of AA[1] through AA[i] is an amino acid residue which is a member independently selected from the group of natural amino acid residues, unnatural amino acid residues and modified amino acid residues;

J denotes the number of amino acid residues forming said peptide sequence and is a member selected from the group consisting of the numbers from 2 to 10, such that J-2 is the number of amino acid residues in the peptide sequence exclusive of AA[1]-AA[2];

i denotes the position of said amino acid residue in sequence relative to AA[1] and when J is greater than 2, i is a member selected from the group consisting of the numbers from 3 to 10; and R is a fluorogenic moiety having the structure:

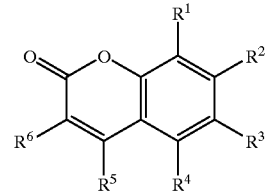

wherein:

$R^1$, $R^2$, $R^3$, $R^4$, $R^5$ and $R^6$ are members independently selected from the group consisting of H, halogen, —NO$_2$, —CN, —C(O)$_m$R$^6$, —C(O)NR$^7$R$^8$, —S(O)$_t$R$^9$, —SO$_2$NR$^{10}$R$^{11}$, —OR$^{12}$, —NR$^{18}$R$^{19}$, substituted or unsubstituted alkyl, —NHC(O)—P, and —R$^{20}$—Y, with the proviso that at least one of $R^1$, $R^2$, $R^3$, $R^4$, $R^5$ and $R^6$ is —R$^{20}$—Y and at least one of $R^1$, $R^2$, $R^3$, $R^4$, $R^5$ and $R^6$ is —NHC(O)—P, wherein:

$R^6$, $R^7$, $R^8$, $R^9$, $R^{10}$, $R^{11}$, $R^{12}$, $R^{18}$ and $R^{19}$ are members independently selected from the group consisting of H, substituted or unsubstituted alkyl and substituted or unsubstituted aryl;

$R^{20}$ is either present or absent and is a member selected from the group consisting of substituted or unsubstituted alkyl and substituted or unsubstituted heteroalkyl;

Y is a member selected from the group consisting of —COOR$^{17}$, CONR$^{17}$R$^{21}$, —C(O)R$^{17}$R$^{21}$, —OR$^{17}$, SR$^{17}$, —C(O)SR$^{17}$ and —NR$^{17}$R$^{21}$ wherein, $R^{17}$ and $R^{21}$ are members independently selected from H, substituted or unsubstituted alkyl and substituted or unsubstituted aryl;

m is a member selected from the group consisting of the integers 1 and 2; and t is a member selected from the group consisting of the integers from 0 to 2.

85. A fluorogenic peptide having the structure:

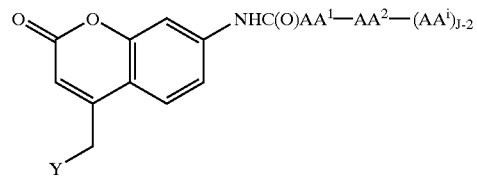

wherein:

each of AA[1] through AA[i] is an amino acid residue which is a member independently selected from the group of natural amino acid residues, unnatural amino acid residues and modified amino acid residues;

J denotes the number of amino acid residues forming said peptide sequence and is a member selected from the group consisting of the numbers from 2 to 10, such that J-2 is the number of amino acid residues in the peptide sequence exclusive of AA[1]-AA[2];

i denotes the position of said amino acid residue in sequence relative to AA$^1$ and when J is greater than 2, i is a member selected from the group consisting of the numbers from 3 to 10; and Y is a member selected from the group consisting of —COOR$^{17}$, CONR$^{17}$R$^{21}$, —C(O)R$^{17}$R$^{21}$, —OR$^{17}$, —SR$^{17}$, —C(O)SR$^{17}$ and —NR$^{17}$R$^{21}$ wherein, R$^{17}$ and R$^{21}$ are members independently selected from H, substituted or unsubstituted alkyl and substituted or unsubstituted aryl.

86. A library of fluorogenic peptides comprising at least a first peptide having a first peptide sequence covalently attached to a first fluorogenic moiety and a second peptide having a second peptide sequence covalently attached to a second fluorogenic moiety, said first peptide and said second peptide having the structure:

R—P wherein:
for each of said first peptide and said second peptide, P is independently selected from peptide sequences having the structure:

—C(O)-AA$^1$-AA$^2$-(AA$^i$)$_{J-2}$ wherein:
each of AA$^1$ through AA$^i$ is an amino acid residue which is a member independently selected from the group consisting of natural amino acid residues, unnatural amino acid residues and modified amino acid residues;

each J is independently selected and denotes the number of amino acid residues forming said first peptide sequence and said second peptide sequence and is a member selected from the group consisting of the numbers from 2 to 10;

each i is independently selected and denotes the position of said amino acid residue relative to AA$^1$ and when J is greater than 2, i is a member selected from the group consisting of the numbers from 3 to 10; and for each of said first peptide and said second peptide R is independently selected from fluorogenic moieties having the structure:

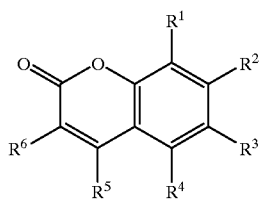

wherein:
R$^1$, R$^2$, R$^3$, and R$^4$ are members independently selected from the group consisting of H, halogen, —NO$_2$, —CN, —C(O)$_m$R$^7$, —C(O)NR$^8$R$^9$, S(O)$_t$R$^{10}$, —SO$_2$NR$^{11}$R$^{12}$, —OR$^{13}$, NR$^{18}$R$^{19}$, substituted or unsubstituted alkyl, —R$^{14}$—SS, and —NHR$^{15}$;

R$^5$ and R$^6$ are members independently selected from the group consisting of H, halogen, —NO$^2$, —CN, —C(O)$_m$R$^7$, —C(O)NR$^8$R$^9$, —S(O)$_t$R$^{10}$, —SO$_2$NR$^{11}$R$^{12}$, —OR$^{13}$, substituted or unsubstituted alkyl, —R$^{14}$—SS, and —NHR$^{15}$, with the proviso that at least one of R$^1$, R$^2$, R$^3$, R$^4$, R$^5$ and R$^6$ is —R$^{14}$—SS and at least one of R$^1$, R$^2$, R$^3$, R$^4$, R$^5$ and R$^6$ is —NHR$^{15}$ wherein:
R$^7$, R$^8$, R$^9$, R$^{10}$, R$^{11}$, R$^{12}$, R$^{13}$, R$^{18}$ and R$^{19}$ are members independently selected from the group consisting of H, substituted or unsubstituted alkyl and substituted or unsubstituted aryl;

R$^{14}$ is a linking group adjoining said fluorogenic moiety and the solid support wherein said linking group is a member selected from the group consisting of substituted or unsubstituted alkyl and substituted or unsubstituted heteroalkyl;

R$^{20}$ is either present or absent and is a member selected from the group consisting of substituted or unsubstituted alkyl and substituted or unsubstituted heteroalkyl;

Y is a member selected from the group consisting of organic functional groups and methyl;

m is a member selected from the group consisting of the integers from 1 to 2;

t is a member selected from the group consisting of the integers from 0 to 2;

R$^{17}$ is a member selected from the group consisting of H, substituted or unsubstituted alkyl and substituted or unsubstituted aryl; and SS is a solid support.

87. The library according to claim 86, wherein said organic functional group is a member selected from the group consisting of —COOR$^{17}$, CONR$^{17}$R$^{21}$, —C(O)R$^{17}$R$^{21}$, —OR$^{17}$, —SR$^{17}$, —C(O)SR$^{17}$, and —NR$^{17}$R$^{21}$ wherein, R$^{17}$ and R$^{21}$ are members independently selected from H, substituted or unsubstituted alkyl and substituted or unsubstituted aryl.

88. The library of fluorogenic peptides according to claim 86, wherein R—P has the structure:

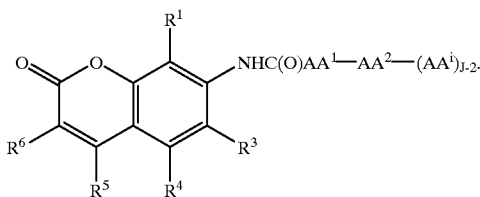

89. The library of fluorogenic peptides according to claim 88, wherein R—P has the structure:

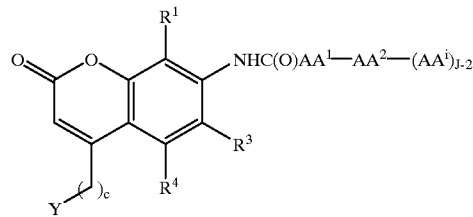

wherein, c is a member selected from the group consisting of the numbers from 0 to 6.

90. The library of fluorogenic peptides according to claim 89, wherein R—P has the structure:

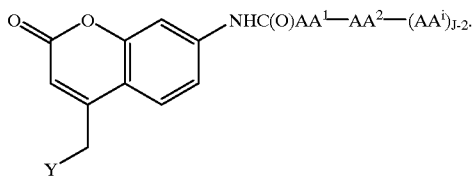

91. The library according to claim 86, wherein said fluorogenic moiety of said first peptide and said fluorogenic moiety of said second peptide are different fluorogenic moieties.

92. The library according to claim 86, wherein said first peptide sequence and said second peptide sequence are identical.

93. The library according to claim 86, wherein said first peptide sequence and said second peptide sequence are different.

94. The library according to claim 93, wherein an amino acid residue selected from the group consisting of $AA^1$, $AA^2$, $AA^i$ and combinations thereof of said first peptide is a different amino acid residue than an amino acid residue at a corresponding position relative to $AA^1$ of said second peptide.

95. The library according to claim 86, wherein $AA^1$ of said first peptide sequence and $AA^1$ of said second peptide sequence are identical amino acid residues.

96. The library according to claim 86, wherein $AA^1$ of said first peptide sequence and $AA^1$ of said second peptide sequence are different amino acid residues.

97. The library according to claim 86, wherein $AA^2$ of said first peptide sequence and $AA^2$ of said second peptide sequence are identical amino acid residues.

98. The library according to claim 86, wherein $AA^2$ of said first peptide sequence and $AA^2$ of said second peptide sequence are different amino acid residues.

99. The library according to claim 86, wherein $AA^i$ of said first peptide sequence and $AA^i$ of said second peptide sequence are identical amino acid residues.

100. The library according to claim 86, wherein $AA^i$ of said first peptide sequence and $AA^i$ of said second peptide sequence are different amino acid residues.

101. The library according to claim 99, comprising at least six peptides having different peptide sequences, wherein $AA^1$ is a different amino acid residue in each of said different peptide sequences.

102. The library according to claim 101, comprising at least twelve peptides having different peptide sequences wherein $AA^1$ is a different amino acid residue in each of said different peptide sequences.

103. The library according to claim 102, comprising at least twenty peptides having different peptide sequences wherein $AA^1$ is a different amino acid residue in each of said different peptide sequences.

104. The library according to claim 86, wherein $AA^1$ is a member selected from the group consisting of Lys, Arg, Leu and combinations thereof.

105. The library according to claim 86, wherein J is a member selected from the numbers from 4 to 8.

106. The library of peptides according to claim 86, wherein at least one of said first peptide and said second peptide is cleavable by a protease into a fluorescent moiety and the peptide sequence.

107. The library according to claim 86, comprising at least 10 peptides, wherein each of the peptide sequences is a different peptide sequence.

108. The library according to claim 107, comprising at least 100 peptides, wherein each of the peptide sequences is a different peptide sequence.

109. The library according to claim 108, comprising at least 1,000 peptides, wherein each of the peptide sequences is a different peptide sequence.

110. The library according to claim 109, comprising at least 10,000 peptides, wherein each of the peptide sequences is a different peptide sequence.

111. The library according to claim 110, comprising at least 100,000 peptides, wherein each of the peptide sequences is a different peptide sequence.

112. The library according to claim 111 comprising at least 1,000,000 peptides, wherein each of the peptide sequences is a different peptide sequence.

* * * * *

UNITED STATES PATENT AND TRADEMARK OFFICE
CERTIFICATE OF CORRECTION

PATENT NO. : 6,680,178 B2
DATED : January 20, 2004
INVENTOR(S) : Harris et al.

It is certified that error appears in the above-identified patent and that said Letters Patent is hereby corrected as shown below:

Column 44,
Line 19, kindly delete "-$SO_2NR^{11}R^{12}$, -$OR^{13}$," and insert -- $SO_2NR^{11}R^{12}$, -$OR^{13}$, $NR^{18}R^{19}$, --

Column 45,
Line 37, kindly delete "A material" and insert -- The material --

Signed and Sealed this

Twenty-fifth Day of May, 2004

JON W. DUDAS
*Acting Director of the United States Patent and Trademark Office*